US008465491B2

(12) United States Patent
Yedlicka et al.

(10) Patent No.: US 8,465,491 B2
(45) Date of Patent: Jun. 18, 2013

(54) BONE DRILL

(75) Inventors: Joseph W. Yedlicka, Indianapolis, IN (US); Robert A. Till, Jr., Avon, IN (US); Nancy S. Yedlicka, Indianapolis, IN (US); Patricia M. Till, Avon, IN (US)

(73) Assignee: Osteo Innovations LLC, Indianapolis, IN (US)

( * ) Notice: Subject to any disclaimer, the term of this patent is extended or adjusted under 35 U.S.C. 154(b) by 1576 days.

(21) Appl. No.: 11/788,413

(22) Filed: Apr. 20, 2007

(65) Prior Publication Data

US 2007/0282344 A1    Dec. 6, 2007

Related U.S. Application Data

(60) Provisional application No. 60/809,945, filed on Jun. 1, 2006.

(51) Int. Cl.
*A61B 17/00* (2006.01)
(52) U.S. Cl.
USPC .......................................................... 606/80
(58) Field of Classification Search
USPC . 606/79–81; 433/165–166, 124, 133; 408/36, 408/141
See application file for complete search history.

(56) References Cited

U.S. PATENT DOCUMENTS

| | | | | |
|---|---|---|---|---|
| 170,129 A * | 11/1875 | Strohm | ............................. | 433/124 |
| 175,626 A * | 4/1876 | Starr | ............................. | 433/133 |
| 186,504 A * | 1/1877 | Starr | ............................. | 433/133 |
| 192,793 A * | 7/1877 | Shoots | ............................. | 408/36 |
| 274,008 A * | 3/1883 | Lincoln | ............................. | 433/133 |
| 372,372 A * | 11/1887 | Hovey et al. | ............................. | 408/36 |
| 420,532 A * | 2/1890 | Cragie | ............................. | 433/124 |
| 651,921 A * | 6/1900 | Vilsiss | ............................. | 606/172 |
| 651,922 A * | 6/1900 | Harper | ............................. | 433/133 |
| 745,722 A * | 12/1903 | Preeman | ............................. | 433/128 |
| 847,133 A * | 3/1907 | Velasco | ............................. | 606/172 |
| 2,177,924 A * | 11/1939 | Conto | ............................. | 378/191 |
| 2,243,718 A * | 5/1941 | Moreira | ............................. | 606/80 |
| 2,250,670 A * | 7/1941 | Joy | ............................. | 175/173 |
| 2,573,462 A * | 10/1951 | Lindsey | ............................. | 408/86 |
| 2,813,280 A * | 11/1957 | Huffman | ............................. | 408/10 |
| 3,848,601 A * | 11/1974 | Ma et al. | ............................. | 606/86 A |
| 4,059,115 A * | 11/1977 | Jumashev et al. | ............................. | 606/82 |
| 4,284,080 A * | 8/1981 | Rehder | ............................. | 606/80 |
| 4,687,385 A * | 8/1987 | Palm | ............................. | 408/76 |
| 4,803,976 A * | 2/1989 | Frigg et al. | ............................. | 606/97 |
| 4,961,740 A * | 10/1990 | Ray et al. | ............................. | 606/247 |
| 5,013,317 A * | 5/1991 | Cole et al. | ............................. | 606/96 |
| 5,236,289 A * | 8/1993 | Salyer | ............................. | 408/127 |

(Continued)

*Primary Examiner* — Mary Hoffman
(74) *Attorney, Agent, or Firm* — Mark S. Leonardo; Brown Rudnick LLP

(57) ABSTRACT

A radiolucent bone drill and/or impact drill is provided, which includes a first portion connected to a second portion. The first portion defines a first axis and the second portion defines a second axis. The second axis is disposed at an angle relative to the first axis. A third portion is connected to the second portion. The third portion has a shaft extending therefrom. The shaft includes a distal end configured to engage bone. The bone drill may include a radiation protection guard mounted to the first portion. Specific drill bits, access sheaths/conduits/tube, curettes, and screwdriver bits designed to be used with the devices are provided. The bone drill may be used to place an access sheath/conduit/tube/needle into a bone in a single step. Methods of use are also disclosed.

19 Claims, 45 Drawing Sheets

U.S. PATENT DOCUMENTS

| | | | | |
|---|---|---|---|---|
| 5,269,787 A | * | 12/1993 | Cozean et al. | 606/107 |
| 5,478,343 A | * | 12/1995 | Ritter | 606/97 |
| 5,607,266 A | * | 3/1997 | Anderson | 408/124 |
| 5,676,545 A | * | 10/1997 | Jones | 433/165 |
| 5,741,253 A | * | 4/1998 | Michelson | 606/86 A |
| 5,772,661 A | * | 6/1998 | Michelson | 606/86 A |
| 5,797,909 A | * | 8/1998 | Michelson | 606/914 |
| 5,927,976 A | * | 7/1999 | Wu | 433/82 |
| 6,520,969 B2 | * | 2/2003 | Lambrecht et al. | 606/130 |
| 6,610,067 B2 | * | 8/2003 | Tallarida et al. | 606/102 |
| 6,887,245 B2 | * | 5/2005 | Kienzle et al. | 606/80 |
| 7,074,225 B2 | * | 7/2006 | Kimura | 606/80 |
| 2002/0133148 A1 | | 9/2002 | Daniel et al. | |
| 2004/0138667 A1 | * | 7/2004 | Kimura | 606/80 |

* cited by examiner

BONE DRILL

CROSS REFERENCE TO RELATED APPLICATION

This patent application claims the benefit of U.S. Provisional Patent Application Ser. No. 60/809,945, filed on Jun. 1, 2006, the contents of which being incorporated herein by reference in its entirety.

I. BACKGROUND OF THE INVENTION

A. Field of the Invention

The present invention relates to medical devices, components, and methods for use thereof, such as bone drills, bone drill assemblies, bone impact drills, bone cavity creation/enlargement devices, guide forceps, and fluid transfer device, especially those for treating vertebral body and sacral fractures, as well as lytic (destructive) tumor deposits in bone, for use in bone biopsies/bone infusions, for procedures requiring bone access and for use in medical procedures requiring a drill driven screwdriver or similar tools especially when there is a need for an off-angle, largely radiolucent bone access device having radiation protection for the operator designed to be used with X-ray (fluoroscopic) guidance.

B. Background Information

Throughout the years and most recently in particular, various instruments have been developed for use in and for particular medical procedures and/or techniques requiring bone access. In some bone access procedures, it is necessary to create one or more holes in a bone or bone sections or to bore through the bone. Medical instruments known as bone drills have been developed for creating such holes and bores. Other instruments such as catheters, needles, guide needles, curettes and the like may then be introduced into the hole. On occasion, a cavity needs to be created or enlarged to facilitate treatment of a bone lesion.

Examples of medical procedures or techniques that require drilling into bone (and thus the use of a bone drill) often require creating a cavity or enlarging a cavity in the bone including vertebroplasty and/or vertebral augmentation procedures, sacroplasty, osteoplasty and bone biopsies/infusions. Other medical procedures require the use of drill-driven screwdrivers or similar tools which may need to be used with X-ray (fluoroscopic) guidance.

Vertebroplasty is a procedure for treating vertebral body (spinal) compression fractures. Sacroplasty is a procedure for treating sacral fractures. Osteoplasty is a procedure for treating painful lytic (destructive) tumor deposits in bone. Osteoporosis is the most common cause for vertebral compression fractures and sacral fractures but tumors involving the spine such as multiple myeloma and metastatic disease can also cause these fractures. A vertebral body compression fracture (VCF) is a fracture involving the vertebral body which causes the vertebral body to be compressed or to collapse. This can lead to shortening and tilting of the spinal column with a forward curvature. This forward curvature can lead to pulmonary and gastrointestinal complications. These fractures are extremely painful and debilitating with many of these patients needing wheelchairs for less painful ambulation; many of these patients are bed-ridden. Vertebroplasty is designed to stabilize VCFs and relieve pain. Vertebral height restoration and deformity reduction are also desired.

In vertebral augmentation and vertebroplasty, access needles are manually pushed or hammered into the fractured vertebral body using fluoroscopic (X-ray) guidance. Various instruments such as a curette may then be inserted through the access needles or tubes. At that point in vertebroplasty, an orthopedic bone filler/cement (e.g. PMMA) is instilled into the fractured bone. However, in vertebral augmentation, before the bone cement is instilled, balloon catheters are inserted through the access needles or tubes into the fractured vertebral body and inflated in an attempt to restore the compressed/collapsed vertebral body to its original height and also to create a cavity in the fractured bone. Following the balloon dilation, the balloons are removed and thicker bone cement is instilled into the fractured vertebral body through the access needles or tubes. The cement hardens quickly for both procedures, providing strength and stability to the vertebra. The progress of both procedures is continually monitored in real time with fluoroscopic (X-ray) guidance.

In sacroplasty, access needles are manually pushed or hammered into the fractured sacrum using fluoroscopic (X-ray) or computed tomographic (CT) guidance. Various instruments such as curettes or balloons may then be inserted through the access needles. An orthopedic bone filler/cement (e.g. PMMA) is then instilled through the access needles/tubes into the fractured sacrum. This has been found to provide pain relief and stability. Procedural progress is continually monitored with CT and/or fluoroscopic guidance.

In osteoplasty, access needles are manually pushed or hammered into the lytic (destructive) bone tumor deposit using fluoroscopic (X-ray) or computed tomographic (CT) guidance. Various instruments such as curettes, balloons, or radiofrequency (RF) probes may be inserted through the access needles. An orthopedic bone filler/cement (e.g.) PMMA is then instilled through the access needles/tubes into the lytic deposit. This has been found to provide pain relief and stability. Procedural progress is continually monitored with CT and/or fluoroscopic guidance.

In bone biopsies, needles are manually pushed or hammered into the bone in order to obtain a specimen. In bone infusions, needles are manually pushed or hammered into the bone in order to achieve bone access.

It has been recognized that it is desirable for a bone drill/impact drill to place the access needles in the targeted bone in a single step using fluoroscopic (X-ray) or CT guidance. It has also been recognized that it is desirable for this bone drill/impact drill to have a guide tube or access needle/conduit in conjunction with a drill bit, the guide tube surrounding the drill bit. The guide tube/access needle may then be used as a conduit into the targeted bone. Placing the access sheath/conduit/tube/needle in a single step increases speed and accuracy of access placement thus improving safety and decreasing radiation exposure to the operator. This drill/impact drill can also be used with various bits (such as a screwdriver) for various medical procedures. However, existing drills suffer from various design defects that make them unsuitable to be used with fluoroscopic (X-ray) or computed tomographic (CT) guidance for these procedures. It is often difficult to place needles or access devices into bone by manually pushing or hammering; also the currently used devices result in excessive radiation exposure to the operator (particularly the hands). Also, currently available bone curettes do not reliably create a cavity in the accessed bone and also result in excessive radiation exposure to the operator (particularly the hands).

It is thus evident from the above that there is a need for an improved bone drill and/or impact drill and related methods of use. It is evident that there is a need for improved drill bits to be used for these applications. It is evident from the above that there is a need for improved cavity creation/enlargement in the targeted bone. It is also evident that there is a need for operator radiation protection when using these devices. It is further evident that there is a need for a guide forceps to be used with these devices. It is also evident that there is a need for a fluid-transfer device to be used with these devices.

II. SUMMARY OF THE INVENTION

An off-angle, largely radiolucent bone access drill and/or impact drill for placing in one step an access needle/tube/conduit into the targeted bone has been invented by applicant. The drill also has radio opaque markers allowing more accurate alignment of the bone drill during use under fluoroscopic guidance. These attributes allow more accurate, rapid, and safe placement of the access needle/tube/conduit into the targeted bone. The present invention also reduces radiation exposure to the physician by allowing his/her hands to be further from the radiation source and patient. Radiation protection to the operator's hand is also provided by a radiation protection guard on the drill handle. The drill/impact drill is also designed to be used with various bits (e.g. screwdriver) for various medical procedures.

In one form, there is provided a bone drill/impact drill for performing the various medical procedures (e.g., vertebroplasty and/or vertebral augmentation procedures, sacroplasty, osteoplasty, bone biopsies/infusions, and other procedures requiring the use of such a drill/impact drill). Portions of the bone drill are radiolucent, while radio opaque markers allow alignment of the bone drill during use (e.g. under fluoroscopy). At least a head portion of the bone drill is formed of the radiolucent material while a drill bit and access needle/sheath/conduit are formed of a radio opaque material. The drill is off-angle reducing radiation exposure by allowing for the operator's hands to be kept out of and further away from the path of the primary X-rays. A radiation protection hand guard on the drill handle provides additional radiation protection to the operator's hand.

In one form, there is provided a bone drill/impact drill assembly especially for performing the above described bone procedures. The bone drill assembly includes a drilling assembly including a drill bit and sheath assembly extending over/outside the drill bit. The sheath assembly is rotated independent of the drill bit and subsequent to drilling of a hole to a partial depth by the drill bit. An oversized hole is created that retains the sheath assembly for use as an instrument tube/conduit.

In one form, there is provided a method of use of the above bone drill/impact drill and bone drill assembly.

In one form, there is provided various embodiments of drilling assemblies for an off-angle bone drill including rotating and non-rotating (cutting and non-cutting) sheaths and two-part drill bits.

The present invention thus provides an off-angle bone drill/impact drill that reduces radiation exposure to the operator by allowing his/her hands and body to be further from the primary radiation source and the patient (scatter radiation). A radiation protection hand guard on the drill handle also provides radiation protection to the operator's hand(s). The bone drill/impact drill is also largely radiolucent with radio opaque markers for aligning the bone drill. Moreover, the drill and sheath assembly provide bone drilling and conduit insertion in one step. The present invention also provides a cavity creation/enlargement tool or device (curette). The curette may be used in conjunction with the present bone drill assembly. The present invention also includes a guide forceps to be used with the devices. The present invention also includes a fluid transfer device. A kit containing some or all of the devices (bone drill, sheath, drill bit, curette, forceps, fluid transfer device and other components all in one or more sizes) may be provided.

In one particular embodiment, in accordance with the principle of the present disclosure, a bone drill/impact drill is provided, which includes a first portion connected to a second portion. The first portion defines a first axis and the second portion defines a second axis. The second axis is disposed at an angle relative to the first axis. A third portion is connected to the second portion. The third portion has a shaft extending therefrom. The shaft includes a distal end configured to engage bone. The bone drill may include a radiation protection guard mounted to the first portion.

At least a portion of the bone drill/impact drill can be radiolucent. The bone drill may include radio opaque markers configured for alignment of the bone drill during a fluoroscopy procedure. The third portion may be formed of the radiolucent material and the shaft formed of a radio opaque material. The third portion may include a drilling assembly having a drill bit and a sheath of the shaft extending about the drill bit. The sheath can be configured to rotate independent of the drill bit and subsequent to drilling of a hole to a partial depth by the drill bit. The shaft may be configured to rotate relative to the third portion. The third portion can define a third axis, the third axis being disposed at an angular orientation relative to the second axis.

The sheath can be configured to rotate in either direction such that the distal end rotates in a clockwise direction or a counterclockwise direction. The shaft may be configured for axial movement relative to the third portion. The axial movement can be spring driven to facilitate an impact engagement of the distal end and the bone. This impact engagement helps to facilitate starting the hole in the desired location. When starting holes with rotary bits, especially on uneven surfaces as would be found on bone, the drill bit tends to walk along the surface instead of biting in. The impact energy directed along the axis of the drill bit helps to imbed the bit in the bone allowing it to bite and start the hole without wandering out of position.

In an alternate embodiment, a method for treating a vertebral body is provided, the method including the steps of: providing a bone drill, similar to those described; exposing an area including the bone drill and the bone to radiation to facilitate alignment, via the radiolucent markers, of the sheath with the bone while protecting a user by maintaining the second axis at the angular orientation relative to the first axis; engaging the distal end of the shaft with the bone; rotating the drill bit and engaging the drill bit with the bone to create a cavity in the bone; driving the sheath into engagement with the bone to further define the cavity in the bone; and treating the bone.

The step of treating may include treating vertebral compression fractures. The step of treating may include treating includes treating sacral fractures. The step of treating may include treating lytic tumor deposits in the bone. The step of treating may include providing access for bone biopsies and/or infusions. The step of treating may include using the drill/impact drill device for use with different bits (such as screwdrivers) for performing various medical procedures. The step of treating may include driving an access needle into the bone using fluoroscopic guidance. The step of treating may include inserting a curette through the access needle in order to create a cavity in the bone. The step of treating may include inserting balloon catheters through the access needle into the bone and inflating the balloon catheter to restore the bone to a desired height and create a cavity in the bone. The step of treating may include instilling filler/cement into the targeted bone. The method for treating a vertebral body may include the step of inserting an access needle into a sacrum using guidance. The method for treating a vertebral body may include the step of inserting an access needle into the lytic bone tumor deposit using guidance.

The method for treating a vertebral body may include the step of irrigating the cavity. The method for treating a vertebral body may include the step of suctioning the cavity. The method for treating a vertebral body may include the step of inflating the cavity.

In another alternate embodiment, the bone drill is configured for treating bone of a vertebral body. The bone drill includes a handle connected to a drive housing. The drive housing is connected to a head portion. The head portion includes a shaft extending therefrom. The shaft includes a drill bit and a sheath disposed about the drill bit. The shaft is coupled to a motor disposed with the drive housing via gearing such that the motor rotates the drill bit and the sheath.

Specific drill bits designed for use with this off-angle drill/impact drill are also described.

The various aspects of the present inventions will be more apparent upon reading the following detailed description in conjunction with the accompanying drawings.

III. BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein.

IV. DETAILED DESCRIPTION OF EMBODIMENTS OF THE INVENTION

The exemplary embodiments of the bone drill and/or impact drill and methods of use disclosed are discussed in terms of medical apparatus and more particularly, in terms of bone drills, bone drill assemblies and bone cavity drills that can be employed for treating vertebral body and sacral fractures. The bone drill may also be employed to treat lytic tumor deposits in bone. It is envisioned that the present disclosure may be employed with a range of applications including vertebroplasty and/or vertebral augmentation procedures, sacroplasty and osteoplasty. It is envisioned that the present disclosure may be used to provide access for bone biopsies and bone infusions. It is also envisioned that these devices may be used with different drill bits (such as screwdrivers) for various medical procedures. It is further envisioned that the present disclosure may be used with other medical applications such as diagnosis, treatment and surgery.

Figure 1:
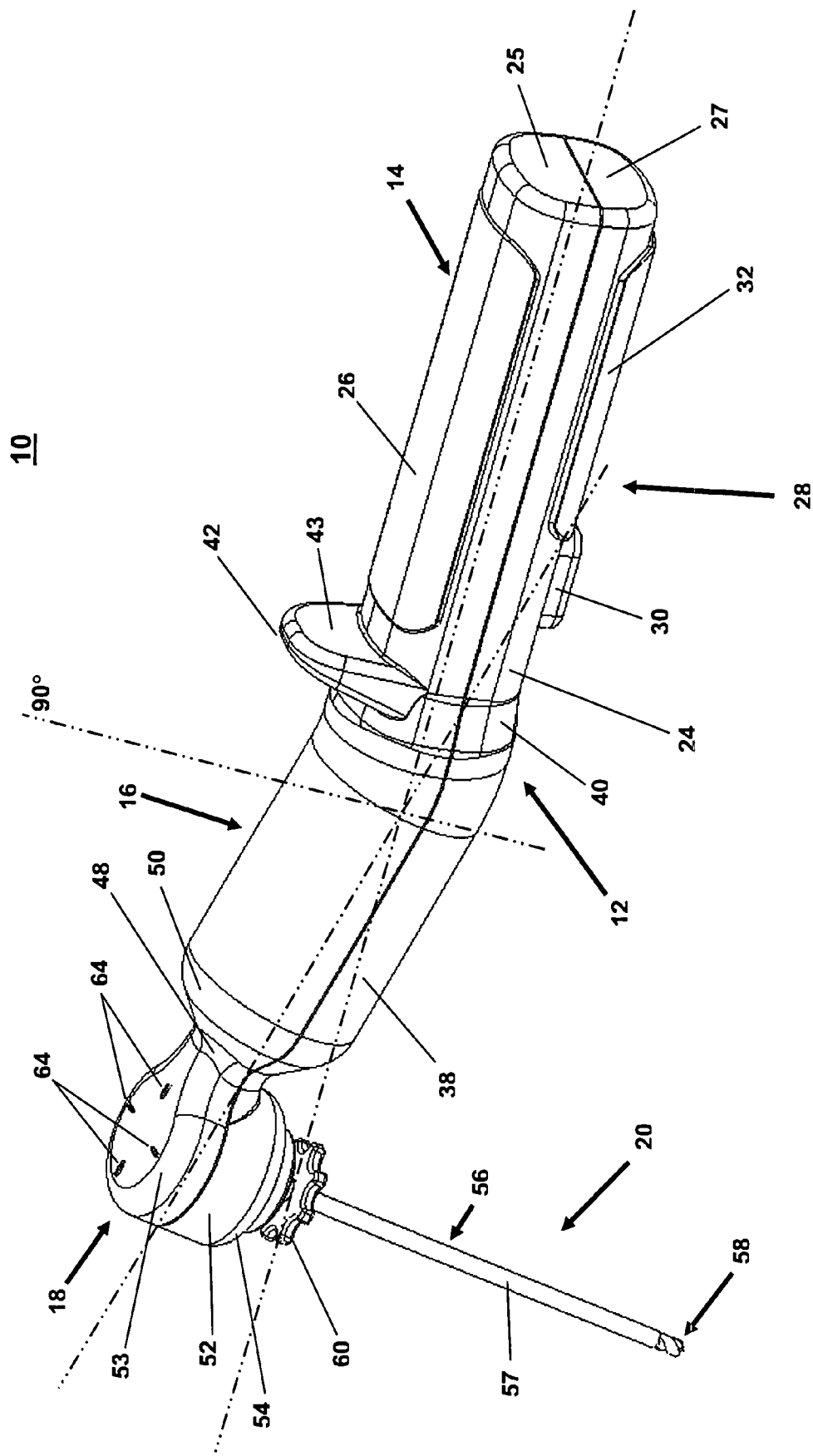
FIG. 1 is a perspective view of one particular embodiment of a bone drill constructed in accordance with the principles of the present invention.

The following discussion includes a description of the bone drill, related components and exemplary methods of operating the bone drill in accordance with the principles of the present disclosure. Alternate embodiments are also disclosed. Reference will now be made in detail to the exemplary embodiments of the present disclosure, which are illustrated in the accompanying figures. Turning now to FIG. 1, there is illustrated a bone drill 10, in accordance with the principles of the present disclosure.

The components of bone drill 10 are fabricated from materials suitable for medical applications, such as, for example, polymerics and/or metals, depending on the particular application and/or preference. Semi-rigid and rigid polymerics are contemplated for fabrication, as well as resilient materials, such as molded medical grade polyurethane, etc. The motors, gearing, electronics and power components of bone drill 10 may be fabricated from those suitable for a medical application. Bone drill 10 may also include circuit boards, circuitry, processor components, etc. for computerized control. One skilled in the art, however, will realize that other materials and fabrication methods suitable for assembly and manufacture, in accordance with the present disclosure, also would be appropriate.

Detailed embodiments of the present disclosure are disclosed herein, however, it is to be understood that the described embodiments are merely exemplary of the disclosure, which may be embodied in various forms. Therefore, specific functional details disclosed herein are not to be interpreted as limiting, but merely as a basis for the claims and as a representative basis for teaching one skilled in the art to variously employ the present disclosure in virtually any appropriately detailed embodiment.

Referring to FIGS. 1-13, bone drill 10 includes a drill body 12 and a drilling assembly 20. Bone drill 10 is adapted to bore a hole into bone such as, for example, into a vertebra or vertebral body during a vertebroplasty procedure and under fluoroscopy. As such, various components, as desired, of bone drill 10, are formed of a radio translucent (radiolucent) material. Thus, only those components that are not radiolucent will show up under x-ray and/or during real time fluoroscopy. It should be appreciated that bone drill 10 is adapted to perform various surgical drilling procedures other than for a vertebroplasty procedure.

In one form, bone drill 10 is adapted to create or drill a bore in bone of a vertebral or sacral body, and to introduce and temporarily leave a tube, tubular sheath or the like of bone drill 10 in the bore. A tubular sheath of bone drill 10 is configured to allow an instrument, component, tool or the like to pass therethrough and provide access to an area at or adjacent to the distal end of the tubular sheath.

Drilling assembly 20 includes a sheath assembly 56 having a tubular sheath 57 and a proximal end terminating in a drive head 60. Drive head 60 includes multiple projections on an outer periphery thereof. Sheath assembly 56 (and thus sheath 57) has a proximal end (see, e.g. FIG. 6) that is preferably serrated or includes drilling teeth 84. Drilling assembly 20 further includes a drill bit 58 having a tipped body 86 and two spiral cutting edges 88, 90. Drill bit 58 is fashioned of a suitable metal. Sheath 57 is also fabricated from metal and thus drilling assembly 20 is not radiolucent.

Body 12 is formed of two (a first and second) portions, sections or halves 25 and 27. The two halves 25, 27 may be considered as upper and lower halves 25, 27. The two halves 25 and 27, when joined, define a first portion, such as, for example, a handle portion 14, a second portion, such as, for example, a drive portion 16 and third portion, such as, for example, a head portion 18. A connecting portion 40 is defined between handle portion 14 and drive portion 16 while a neck 48 is defined between drive portion 16 and head portion 18. Upper and lower halves 25, 27 are formed of a surgically-acceptable material such as a plastic, composite or the like.

Upper and lower halves 25, 27 forming handle portion 14 define a generally tubular body 24. Upper half 25 of the body has a palm area 26. Body 24 also includes an opening 31 (see FIG. 13) on another side thereof (in lower half 27) through which a trigger switch or on/off button 30 extends. In a preferred form, bone drill 10 has a trigger style switch for variably controlling rotational speed of the shaft. Bone drill 10 may also include a reversing (rotation direction) switch.

Figure 2:
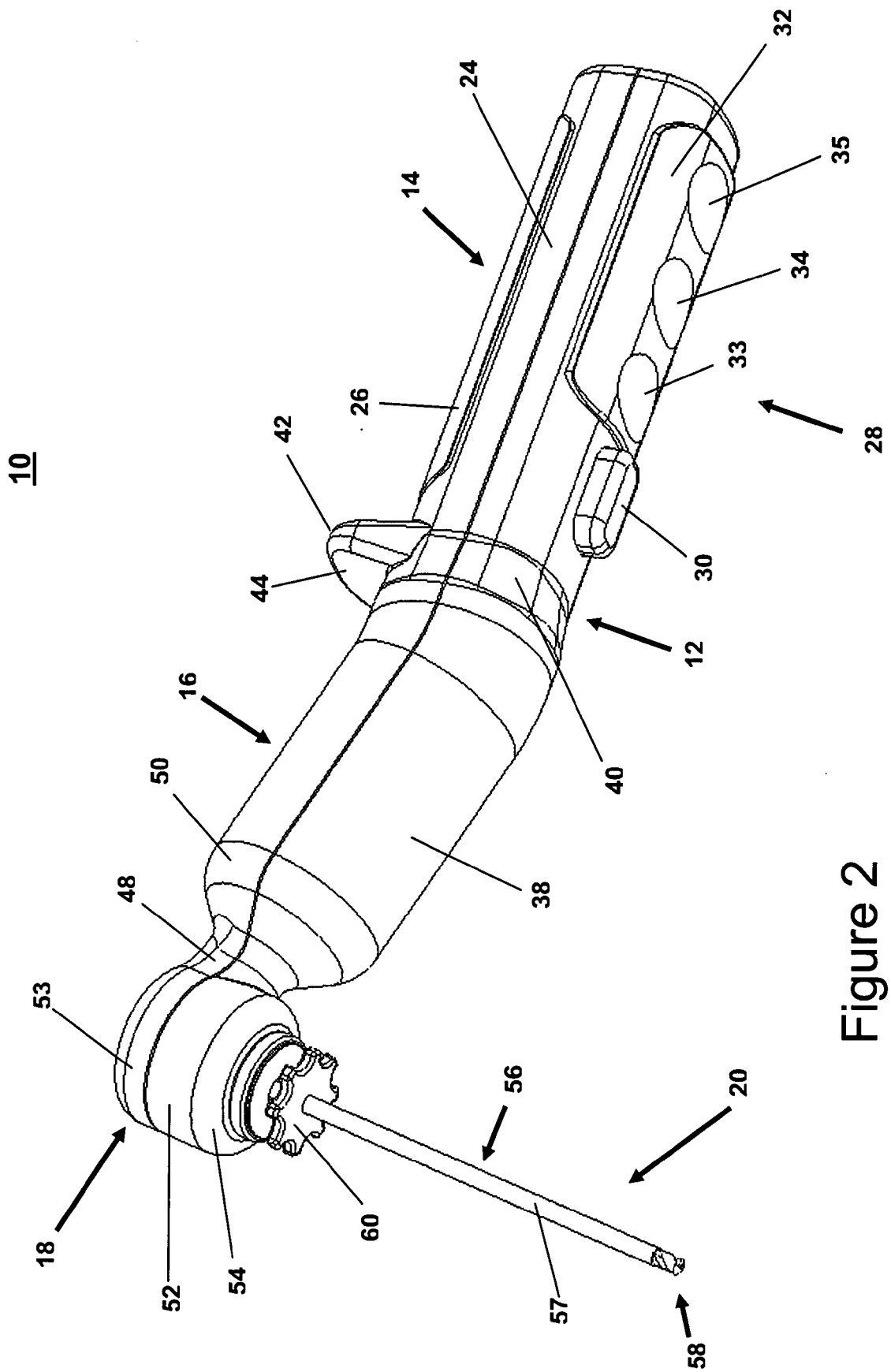
FIG. 2 is a bottom, side perspective view of the bone drill shown in FIG. 1.
Figure 7:
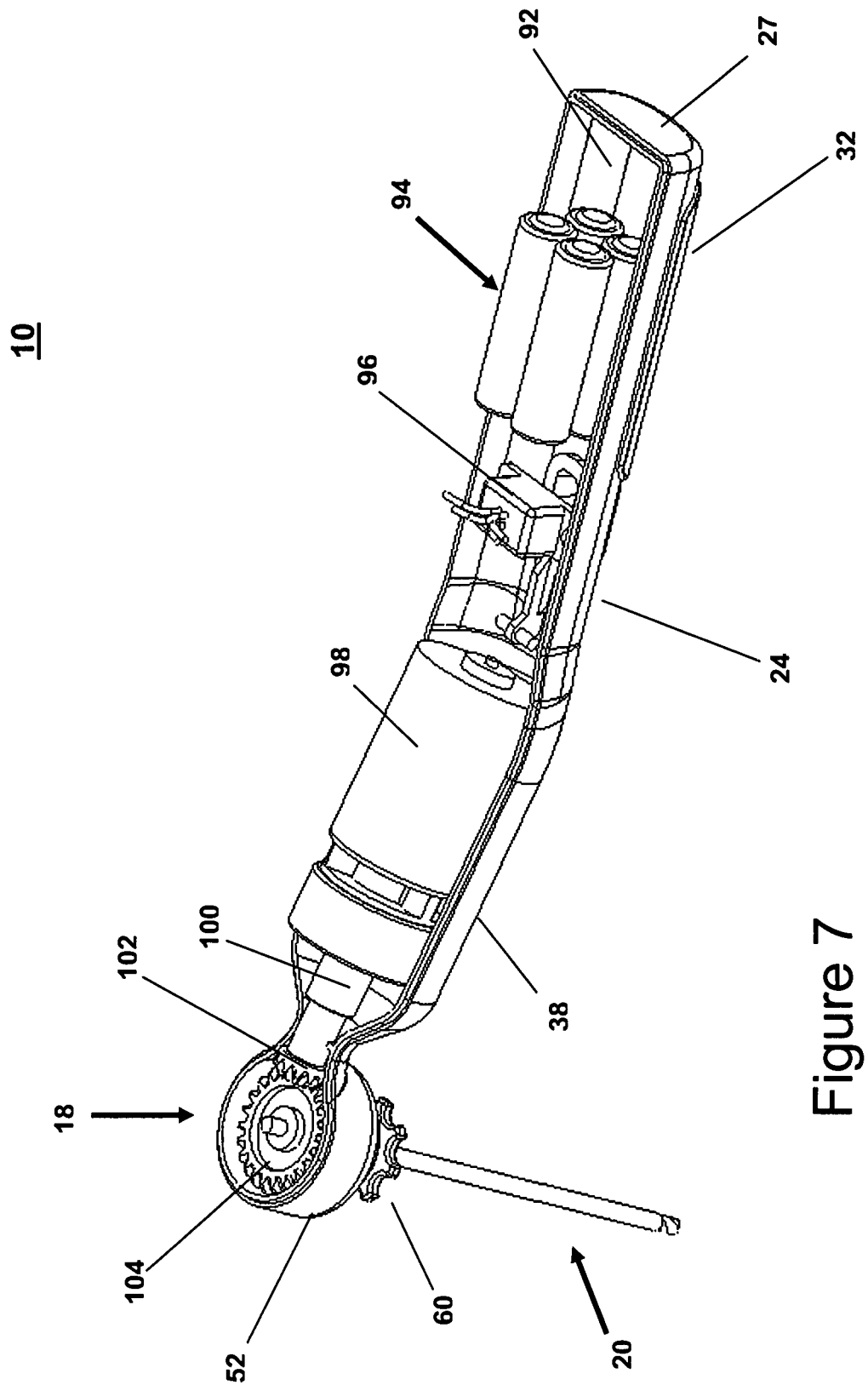
FIG. 7 is a perspective view of the bone drill shown in FIG. 1, with a body portion removed.
Figure 12:
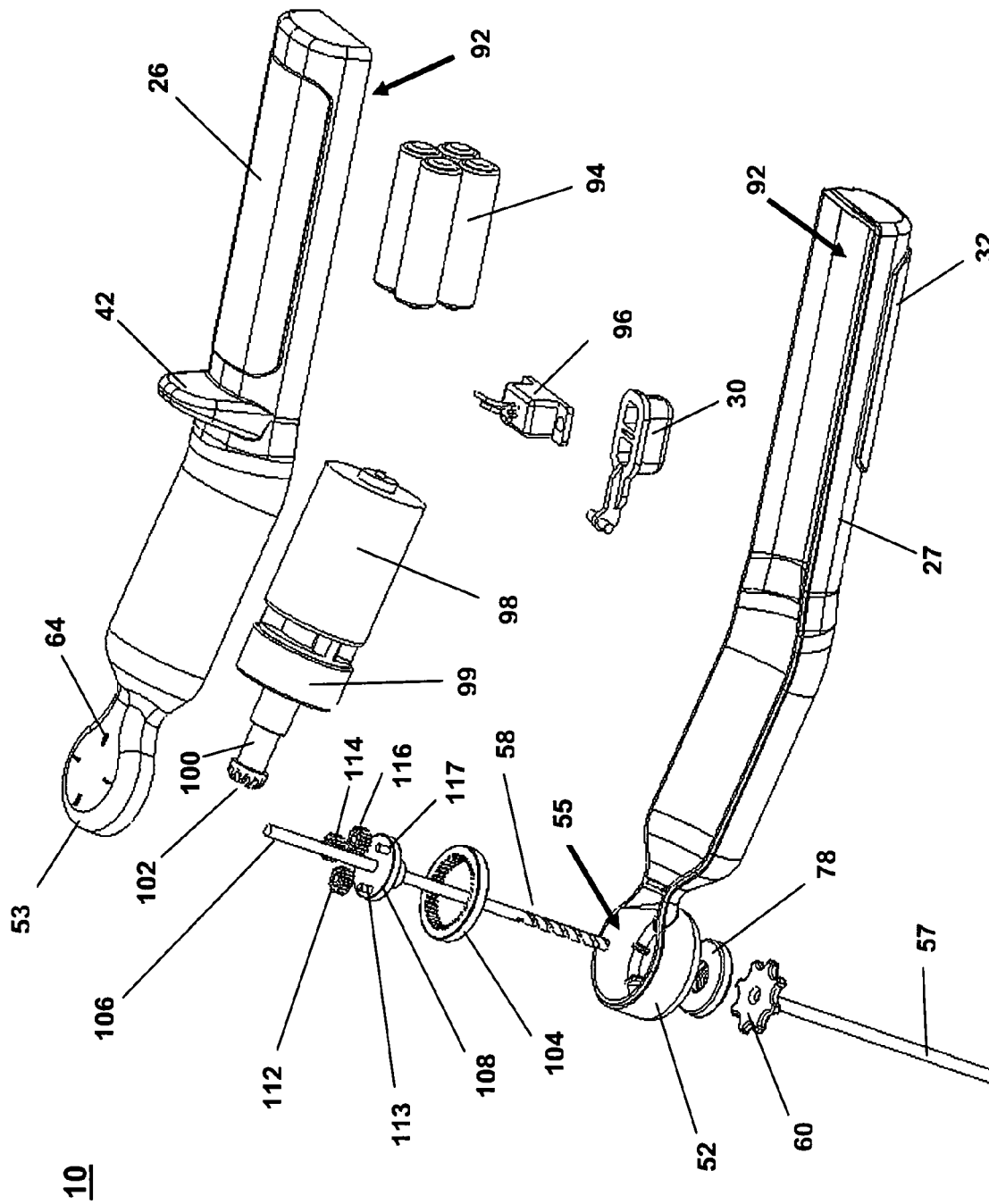
FIG. 12 is an exploded perspective view of the bone drill shown in FIG. 1.
Figure 13:
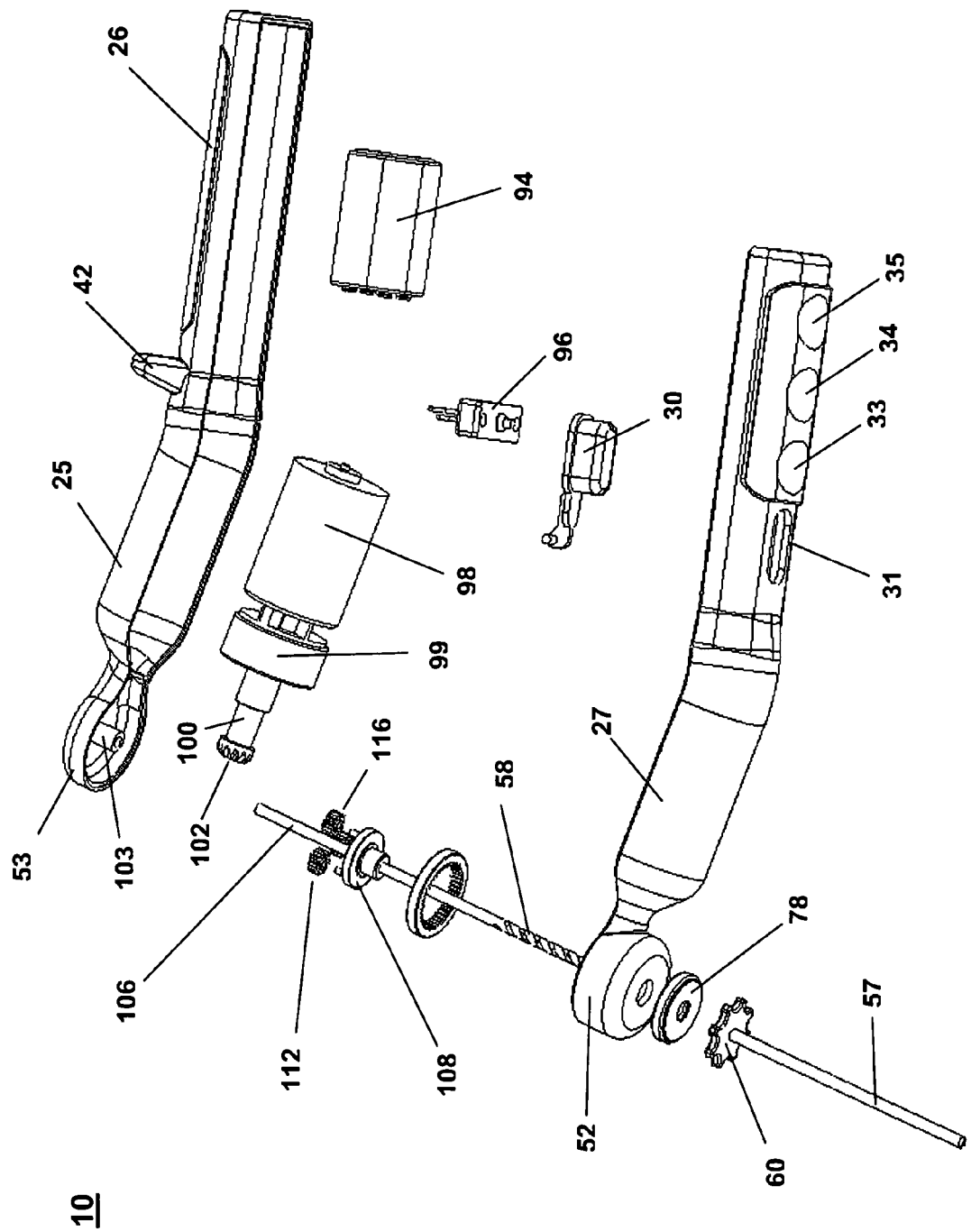
FIG. 13 is an exploded bottom perspective view of the bone drill shown in FIG. 1.

As shown in FIGS. 7, 12 and 13, button 30 pivots and is operatively coupled with and actuates speed controller 96 for bone drill 10. A finger grip area 28 is disposed adjacent to control button 30. As shown in FIG. 2, finger grip area 28 includes three finger indentions 33, 34, 35 that each accommodate a finger of a user's hand as the user is gripping handle portion 14. The two halves 25, 27 form an interior cavity or area 92, which houses a battery or battery pack 94.

Body 12 includes a projection 42 formed on connecting portion 40 and particularly upper half 25, that is adjacent handle portion 14. Projection 42 is generally arc-shaped and defines first and second sides 43, 44 that are generally perpendicular (to slightly angled inwardly toward an apex of projection 42) to the longitudinal axis of first portion 14. An operator or user of bone drill 10 may utilize projection 42 to position the operator's thumb onto bone drill 10.

Drive portion 16 is defined by a generally tubular body 38 defined from appropriate portions of upper and lower halves 25, 27. As shown, for example, in FIGS. 7, 10, 12 and 13, a motor 98 is disposed within tubular body 38. Motor 98 is appropriate for power supply 94 (e.g. batteries) and can be an AC or DC motor. Motor 98 is electrically coupled to batteries 94 and speed controller 96 such that depressing trigger 30 actuates controller 96. The more trigger 30 is depressed the greater the speed of the shaft of bone drill 10.

Figure 8:
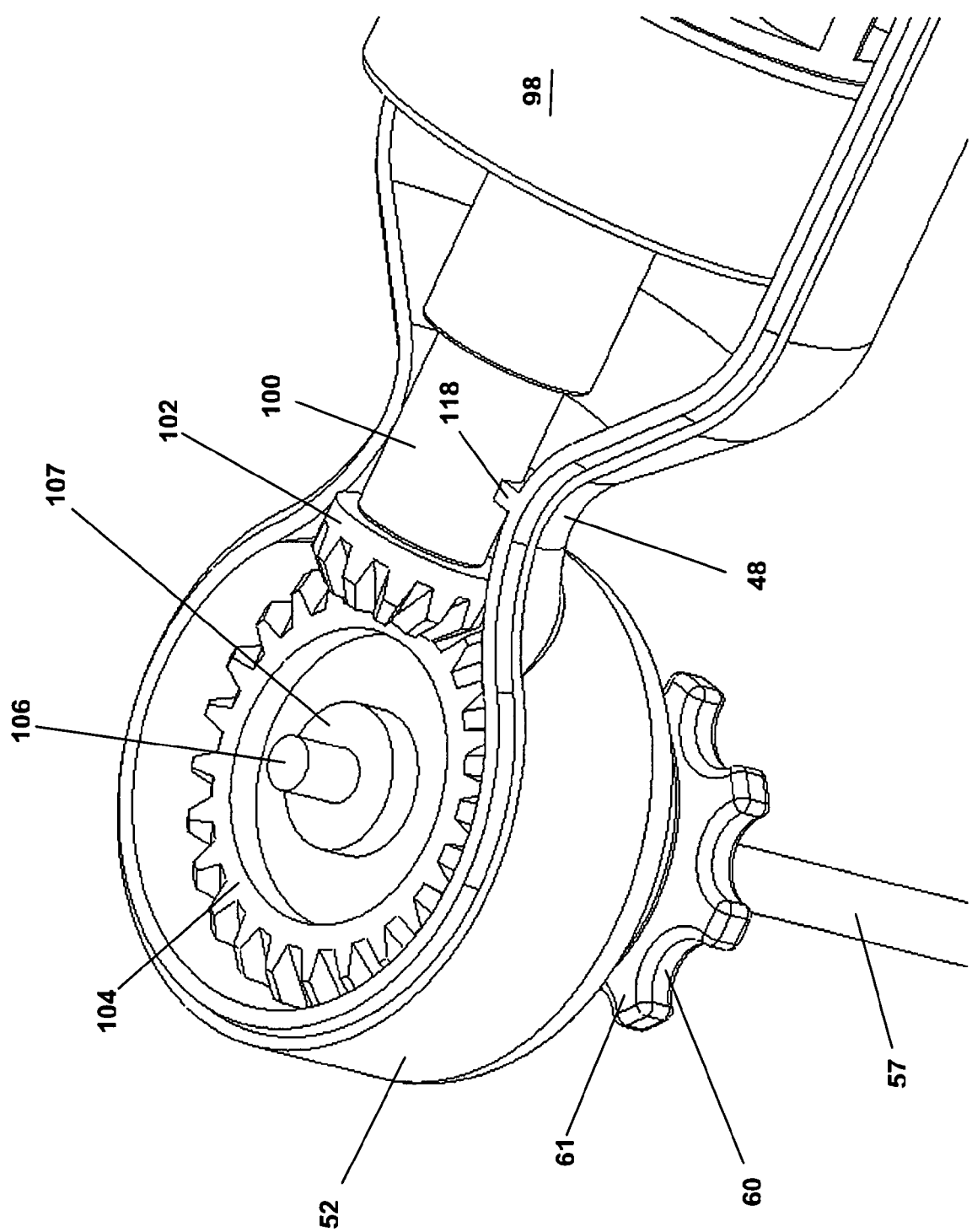
FIG. 8 is an enlarged perspective cutaway view of the head portion shown in FIG. 7.
Figure 9:
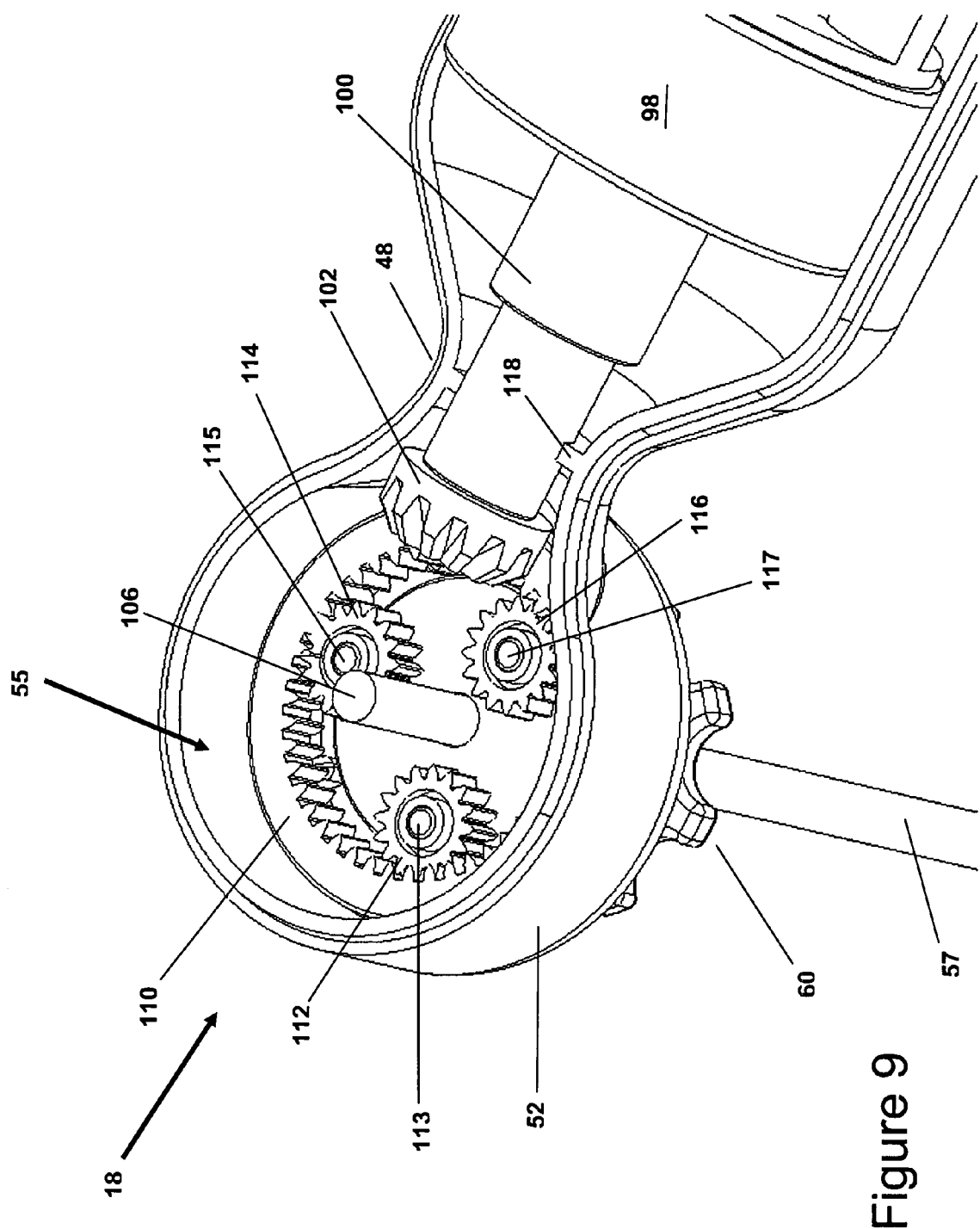
FIG. 9 is the enlarged perspective cutaway view of the head portion shown in FIG. 8 with a gear portion removed.
Figure 10:
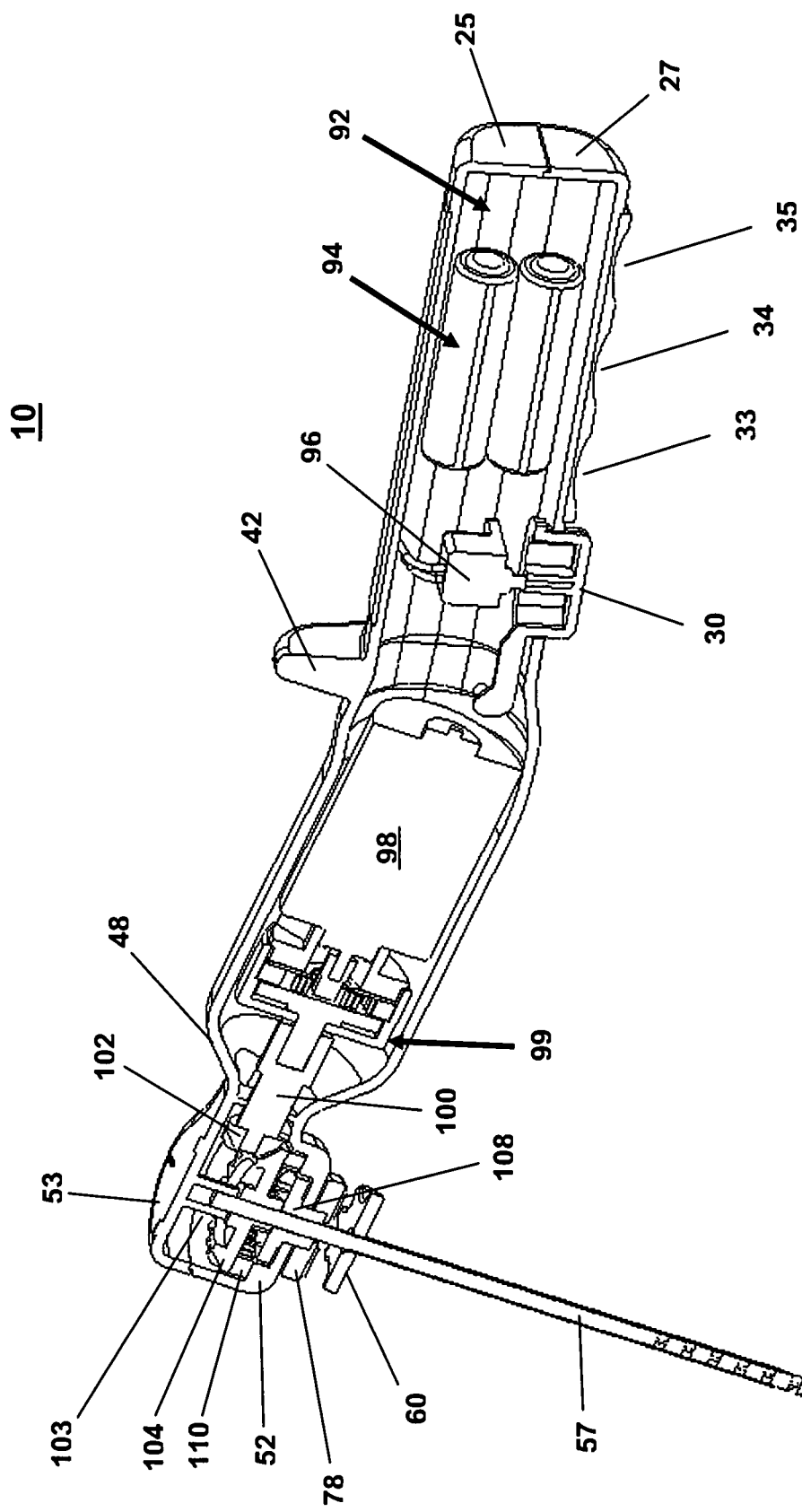
FIG. 10 is a side perspective view in cross section of the bone drill shown in FIG. 1.

The upper and lower halves 25, 27 define a neck or neck portion 48 that provides connection between the drive portion body 38 and head portion 18. Head portion 18 has a generally cylindrical/annular body 52 that is defined by a top head section 53 and a bottom head section 54. As shown in FIGS. 8 and 9, for example, body 52 defines an interior cavity 55 that houses the drilling assembly drive gearing.

Motor 98 includes gearing 99 (see, e.g., FIG. 11) that is operatively coupled to the motor and to an output assembly 101 such that rotation of the motor shaft via gearing 99 rotates output shaft 101. An output drive sleeve 100 is connected to output shaft 101 for rotation therewith. Output drive sleeve 100 is retained for rotation in a mount 118 formed on the inside of neck 48 (see, e.g. FIGS. 8 and 11). A bevel gear 102 is connected to the output drive sleeve for meshing/engaging with the drilling assembly gearing in head portion 18.

Figure 11:
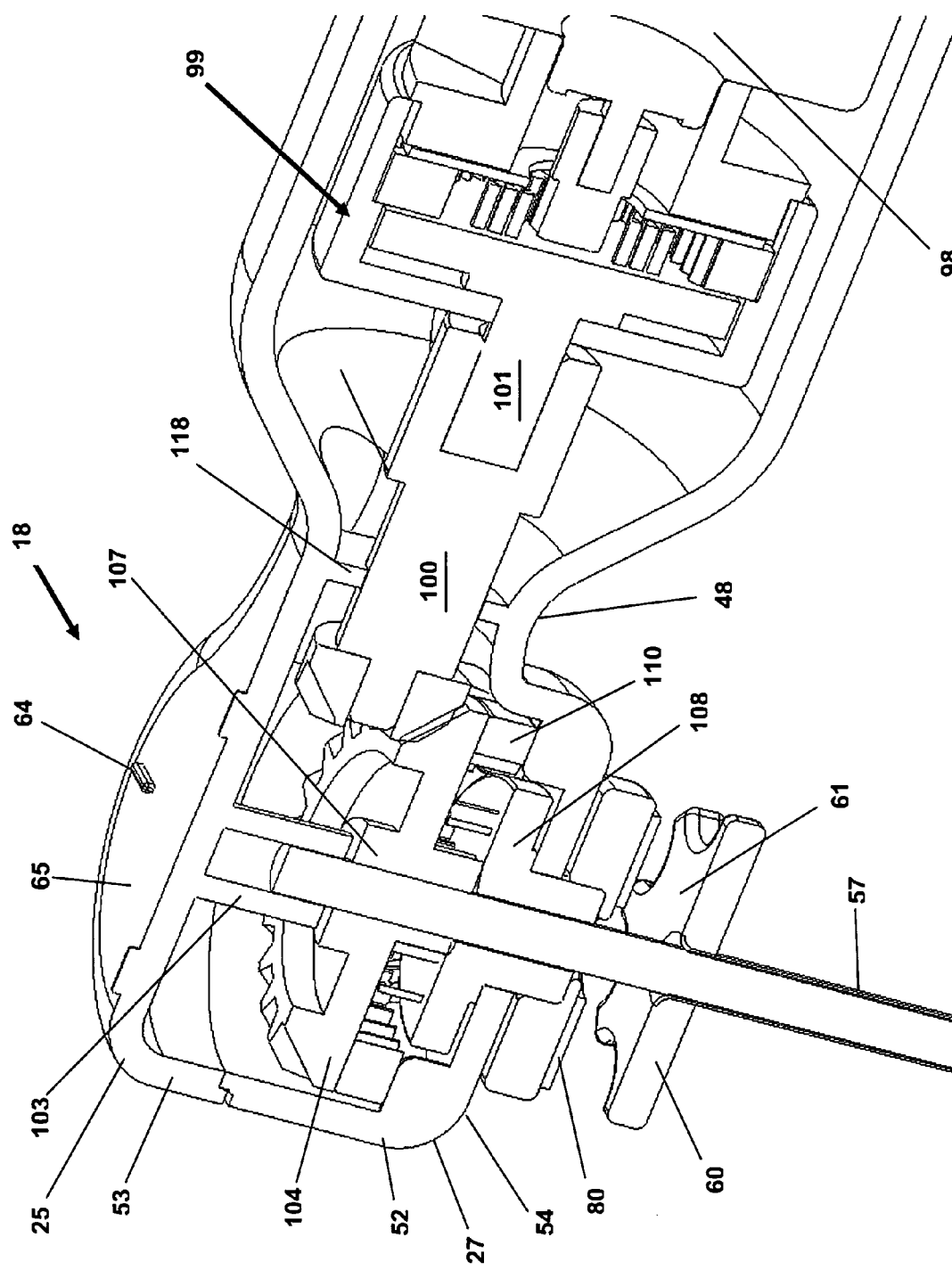
FIG. 11 is an enlarged perspective view of the head portion shown in FIG. 10.

As shown in FIG. 8, bevel gear 102 meshes with an input gear 104 of the drilling assembly gearing. Input gear 104 is retained on shaft end 106 of drill bit 58 via a retention washer 107 and includes teeth on an outer radial periphery thereof that meshes with the teeth of bevel gear 104. Thus, as bevel gear 102 rotates input gear 104, input gear 104, coupled to drill bit 58 via retention washer 107, rotates drill bit 58. As shown in FIGS. 9 and 11, input gear 104 consists of a larger bevel gear mated to a smaller spur gear. The spur gear meshes with the three planetary gears 112, 114, and 116 which in turn mesh with lower gear ring 110. Lower gear ring 110 is fixed against rotation and includes teeth on the radially inside periphery thereof. An annular plate 108 carrying three gears 112, 114 and 116 via respective gear shafts 113, 115 and 117 is situated radially inside input/lower gears 104/110. Gears 112, 114, 116 are rotated by input gear 104 and process along the lower gear ring 110. The procession of the planet gears along ring gear 110 rotates plate 108. A drive cylinder 78 is connected to the lower portion of plate 108 so as to rotate therewith. Drive cylinder 78 is adapted to engage and drive (rotate) sheath assembly 56 of drilling assembly 20 via the head.

It is envisioned that sheath 57 rotates at a first speed and drill bit 58 rotates at a second speed. The planetary gear drive (plastic and radiolucent portions of head portion 18) in head portion 18 meshes with the gear head of motor 98 to spin drill bit 58 at a first speed. The gear head on motor 98 reduces the speed, used to spin drill bit 58, to a second speed for rotating sheath 57. The planetary gear set in the drill head is used to drive the sheath at the second or reduced speed for better feed rate control. The drill bit spins at the first or faster speed to do the bulk of the bone removal while the slower sheath cutting speed keeps the drill bit from "digging in" and bogging down motor 98. It is contemplated that the first and second speeds may vary in range, may be equal and/or the first speed may be less than the second speed.

Optionally, if the ring gear of the planetary gear train in the gear head is left free to rotate (i.e. it is not fixed to the housing), the drive for the sheath will remain stationary. To then engage the sheath, a braking force is applied to the ring gear through a trigger on the handle. Slowing and/or stopping the ring gear will cause the sheath drive to rotate at a variable rate. This configuration is a feed rate or speed control for the sheath rotation giving the user a finer control on how fast the sheath/drill plunges into the bone.

It is envisioned that sheath 57 rotates in a first direction and drill bit 58 rotates in a second direction, such as clockwise and counter-clockwise. The sheath may be moved in a counter direction (counter rotation) to the drill bit. This is accomplished by holding the planetary gear plate 108 stationary and attaching the sheath drive plate to the ring gear, which is now free to rotate. The ring gear will spin in the opposite direction as the sun gear (drill bit), at a reduced speed.

Figure 5:
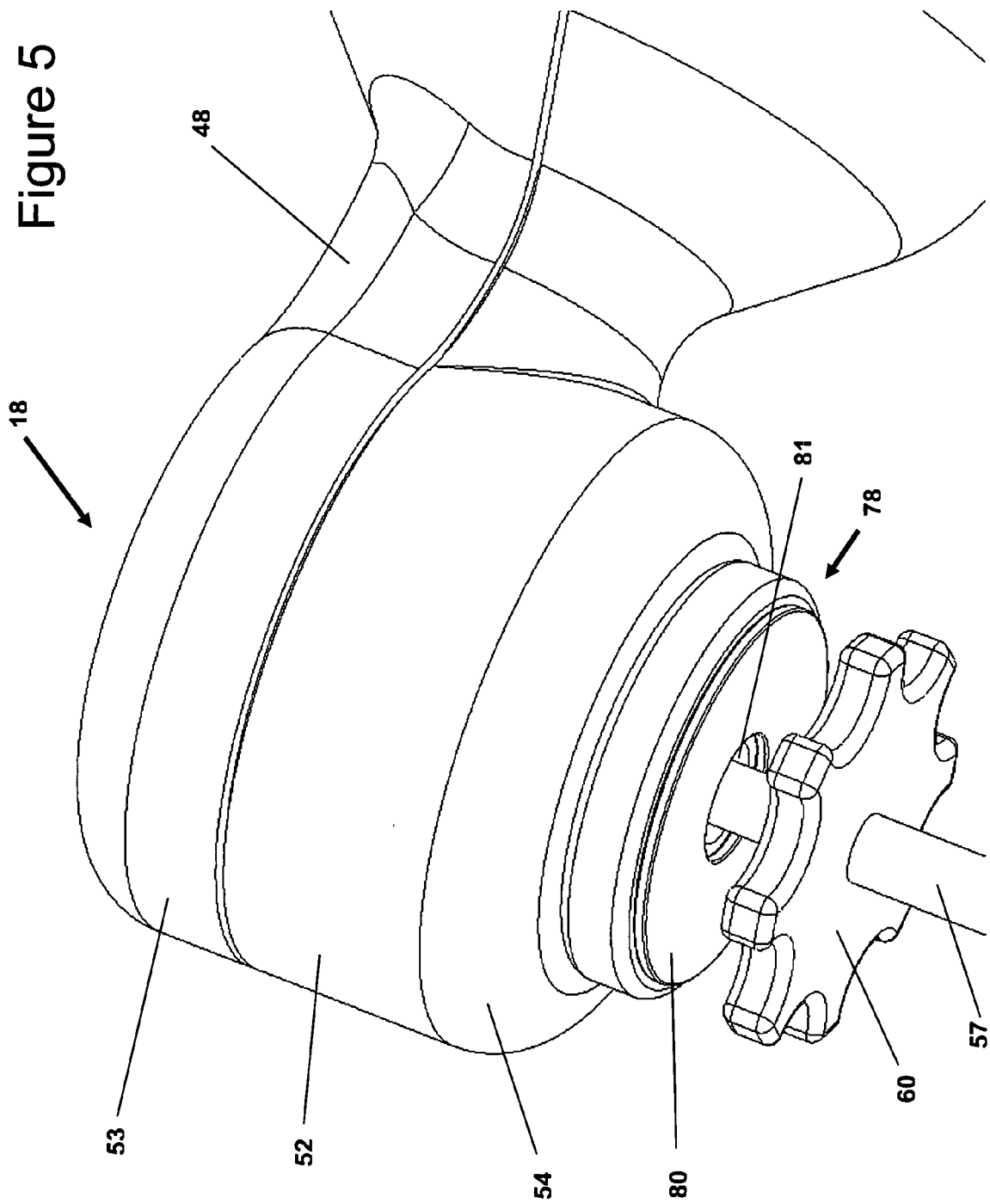
FIG. 5 is an enlarged bottom, side perspective cutaway view of the head portion shown in FIG. 1.
Figure 6:
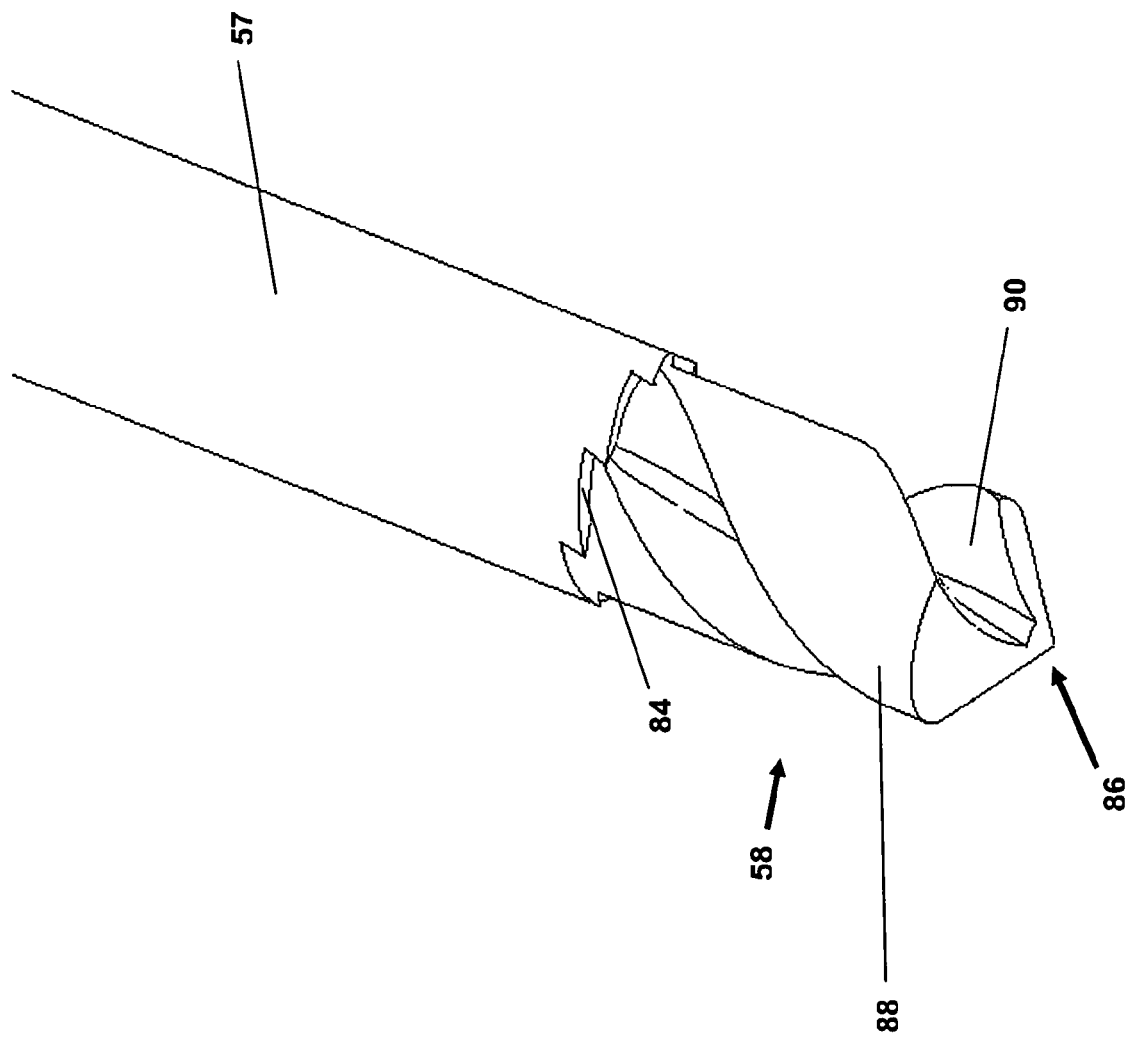
FIG. 6 is an enlarged bottom, side perspective cutaway view of a portion of a boring assembly of the bone drill shown in FIG. 1.

Referring to FIG. 5, end 80 of drive cylinder 78 of bone drill 10 is adapted to frictionally engage an upper surface 61 of drive head 60. Thus, when end 80 of drive cylinder 78 engages drive head 60 of sheath assembly 50, sheath 57 rotates to ream the bore started by and/or being cut by drill bit 58. Thus, a bore is created that allows sheath 57 to extend therein. Thus, one mode of driving sheath assembly 50 is by friction via a friction plate.

Cutting sheath 57 is, thus, not driven initially. It remains stationary to guide drill bit 58 when starting a hole. As drilling progresses, drive head 60 is frictionally engaged by drive cylinder 78 such that the sheath assembly is subsequently (after the start of drill bit rotation), rotated. This cuts a hole large enough for the sheath to follow the drill bit into the bone.

Figure 14:
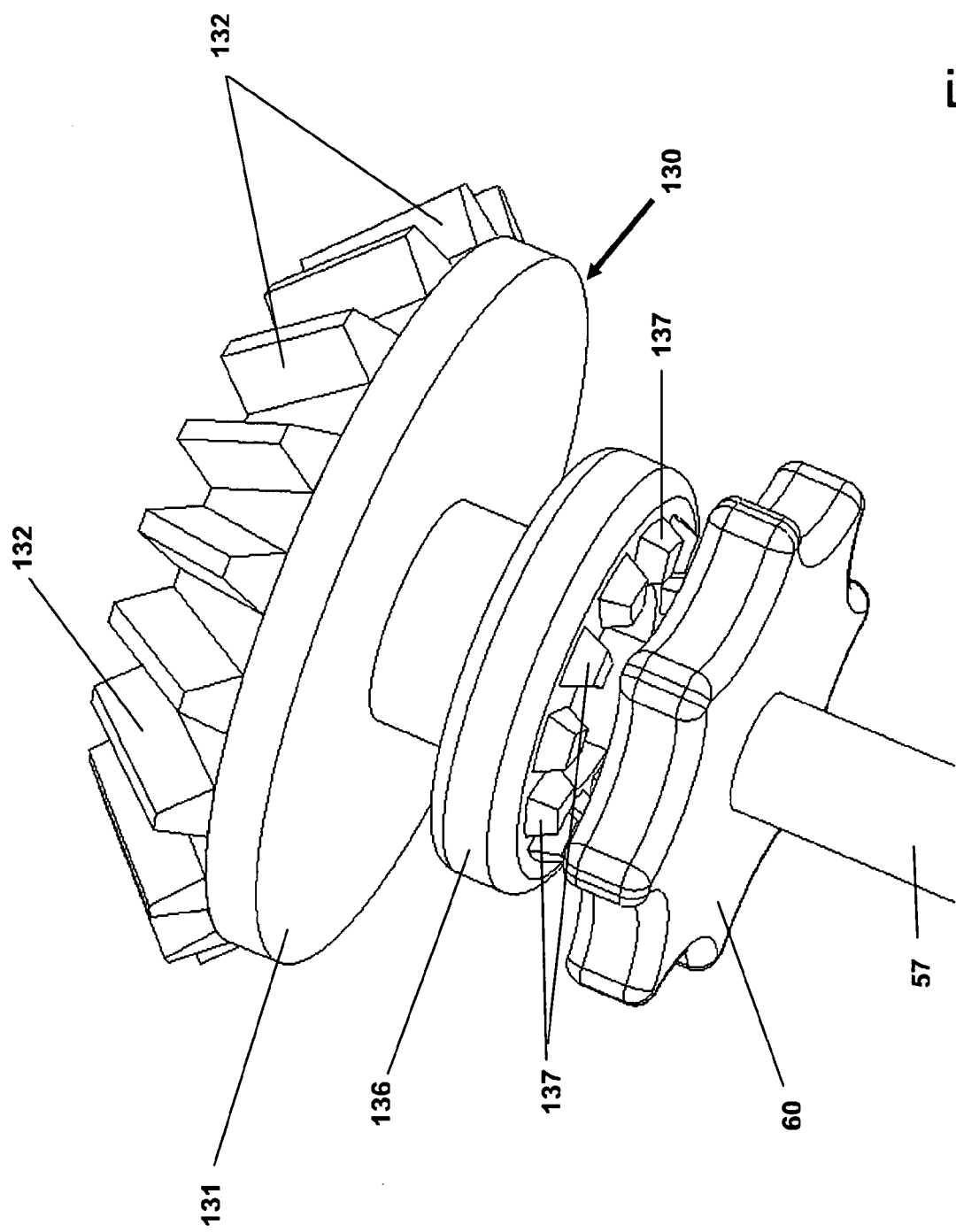
FIG. 14 is an enlarged perspective view of coupling portions of the drill bit assembly of the bone drill of FIG. 1.
Figure 15:
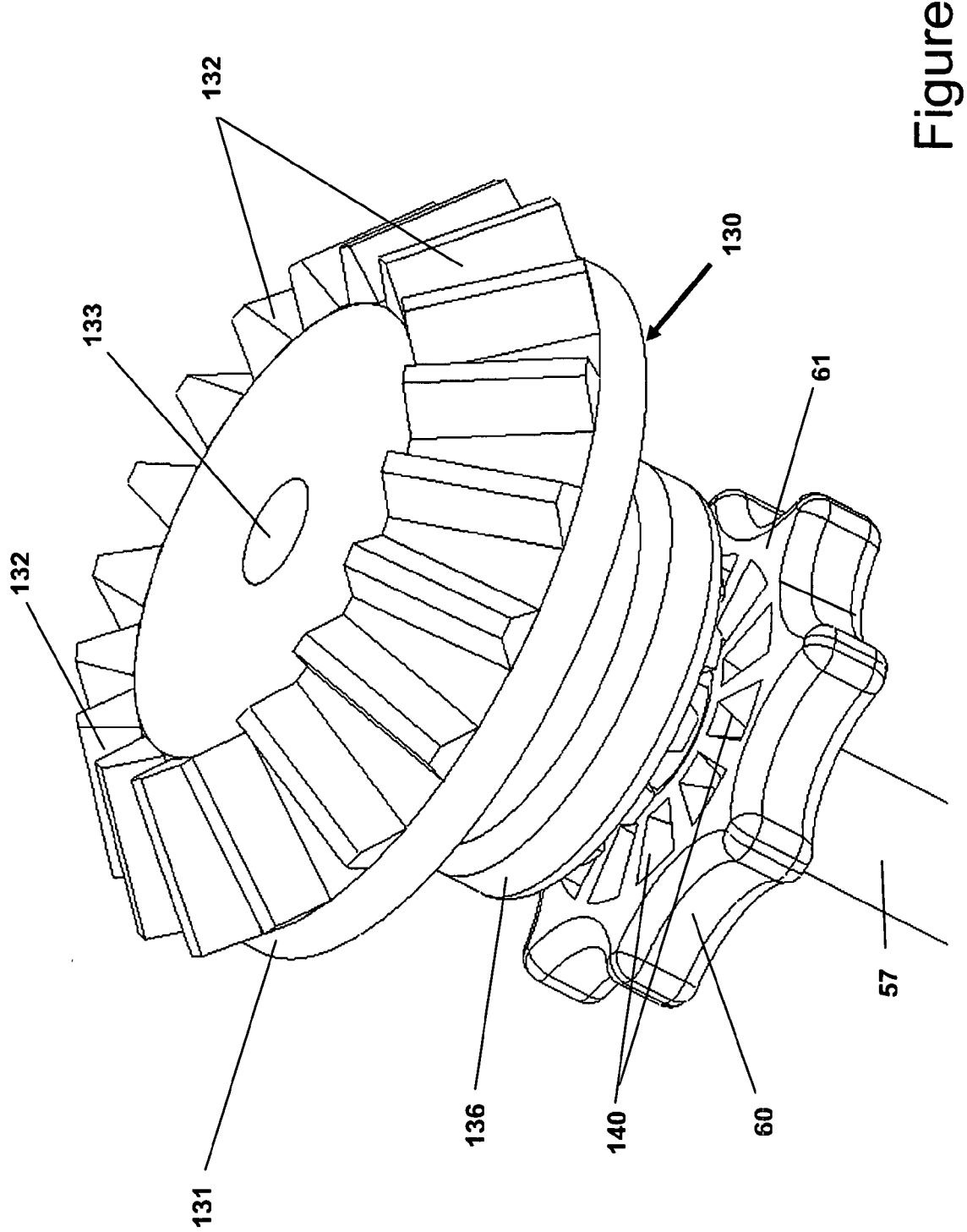
FIG. 15 is an enlarged perspective cutaway view of coupling portions of the drill bit assembly of the bone drill shown in FIG. 1.

Referring to FIGS. 14 and 15, an alternate mode of driving sheath assembly 20 by bone drill 10 is shown, illustrating an embodiment of a direct engagement manner of driving the sheath. Top surface 61 of drive head 60 includes a plurality of notches 140. Notches 140 are depicted as trapezoidal and radiating from a longitudinal axis of sheath 57. The drive gearing for head portion 18 includes an annular drive gear 130 with angled teeth for engaging bevel gear 104. A shaft 134 extends from an undersurface 131 of gear 130 and terminates in a drive wheel 136. Drive wheel 136 has a plurality of teeth 137 corresponding in number and configuration to notches 140 of the drive head. In this manner, once teeth 137 engage notches 140, rotation of drive wheel 37 will be imparted to the sheath assembly through direct engagement.

In this instance, cutting sheath 57 is, thus, not driven initially. It remains stationary to guide drill bit 58 when starting a hole. As drilling progresses, the sheath assembly is subsequently (after bit rotation) engaged to start rotating the sheath assembly.

As shown in FIG. 1, by the respective x-y coordinate arrows, handle portion 14 defines a longitudinal axis (x-axis), drive portion 16 defines a longitudinal axis (x-axis), and head portion 18 defines a longitudinal axis (x-axis). Head portion 18 defines a y-axis (which is co axial with drill bit 58). It can be appreciated from FIG. 1 that drive portion 16 is offset from handle portion 14, along with head portion 18. Head portion 18 may be offset from drive portion 16. It is envisioned that the longitudinal axis of drive portion 16 may be coaxial with the longitudinal axis of handle portion 14, and the longitudinal axis of head portion 18 offset from the drive/handle portions. These configurations allow a safe distance between a doctor's hand and radiation. A range of relative angular offset may be employed.

Figure 3:
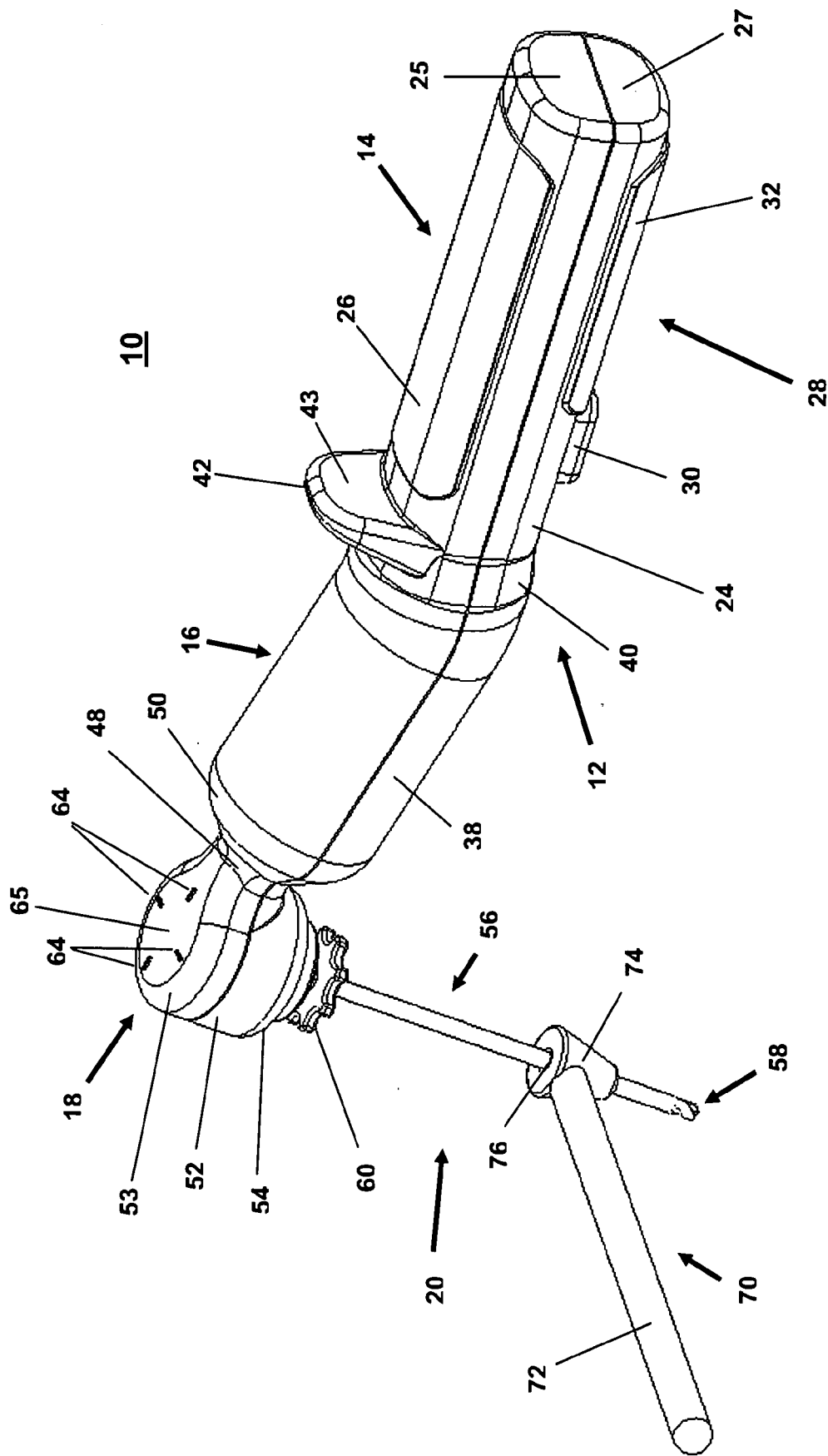
FIG. 3 is a perspective view of the bone drill shown in FIG. 1 having a guide/stabilizer.

In an alternate embodiment, FIG. 3 shows bone drill 10 with an optional drilling guide 70 that may be used to hold and/or stabilize drilling assembly 20 during use. Drilling guide 70 is preferably formed of a radiolucent material. Drilling guide 70 includes a frustoconical shaped body 74 having a central bore 76. A rod 72, in a handle configuration, extends generally perpendicular to the axis of bore 76. Bore 76 is sized to allow the sheath 76 to extend there through.

Figure 4:
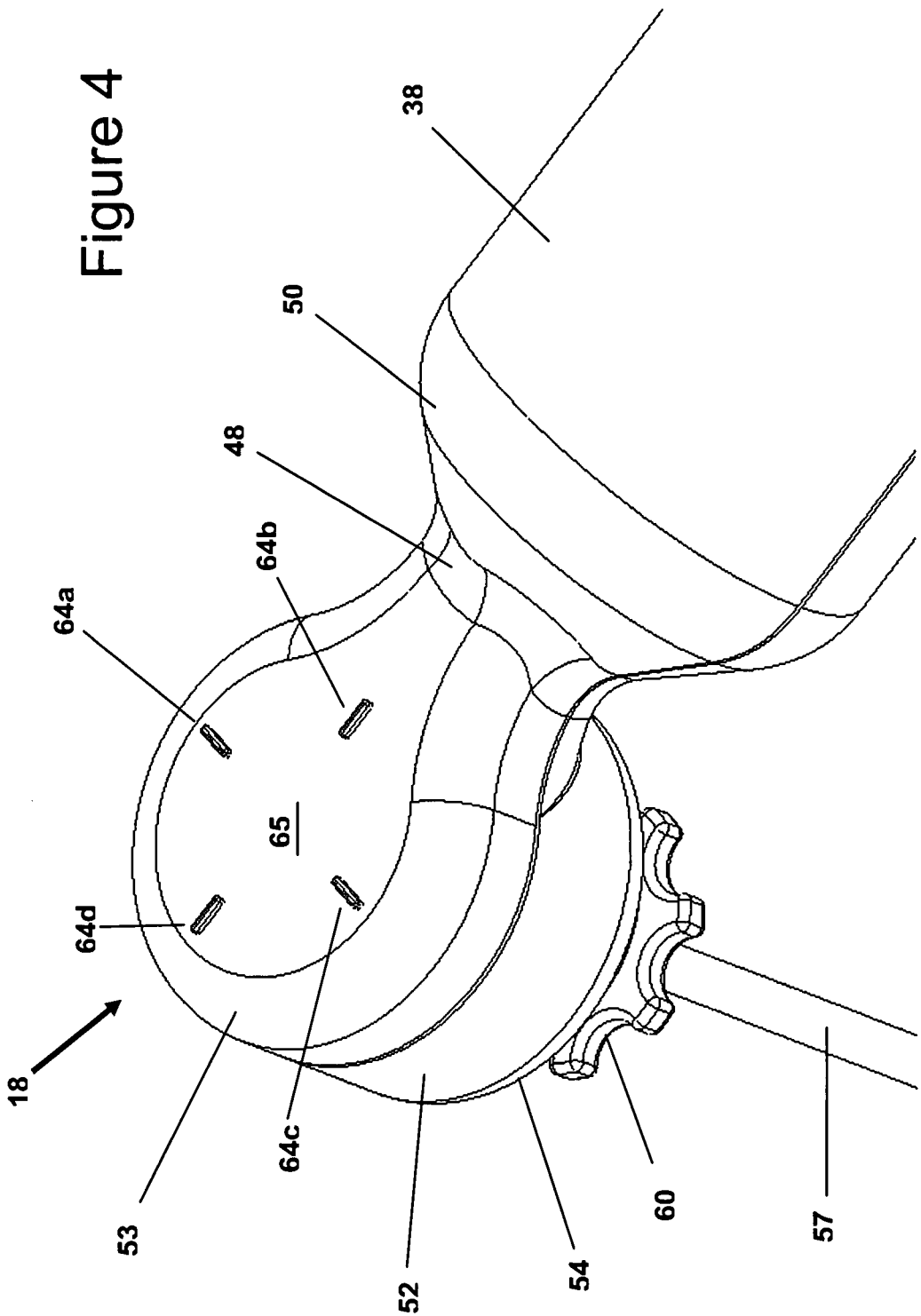
FIG. 4 is an enlarged top, side perspective cutaway view of a head portion of the bone drill shown in FIG. 1.

FIG. 4 provides a perspective view of head portion 18 showing four radio opaque markers 64 (i.e. 64a, 64b, 64c, 64d) radially surrounding the longitudinal axis of drill bit 58, the longitudinal axis thereof forming a center point for radio opaque markers 64. The four radio opaque markers provide reference points for aligning the drill bit. Other configurations and/or scales may be provided as radio opaque markers.

It should be appreciated that drilling assembly 20 (drill bit 58 and sheath 57) is sized to provide a full sized hole in a single pass. Moreover, drilling assembly 20 is sized such that drill bit 58 extends beyond end 84 of sheath 57 (see, e.g. FIGS. 1 and 2). Particularly, the length of sheath assembly 56 (sheath 57 and drive head 60) allows an end 86 of drill bit 58 to extend beyond end 84 of sheath 57 while drive head 60 does not abut or engage drive surface 80 of drive unit 78. It is contemplated that sheath 57 may include a plurality of cutting tines configured to engage and cut bone. It is further contemplated that the tines are moveable relative to the distal end of sheath 57.

Figure 16:
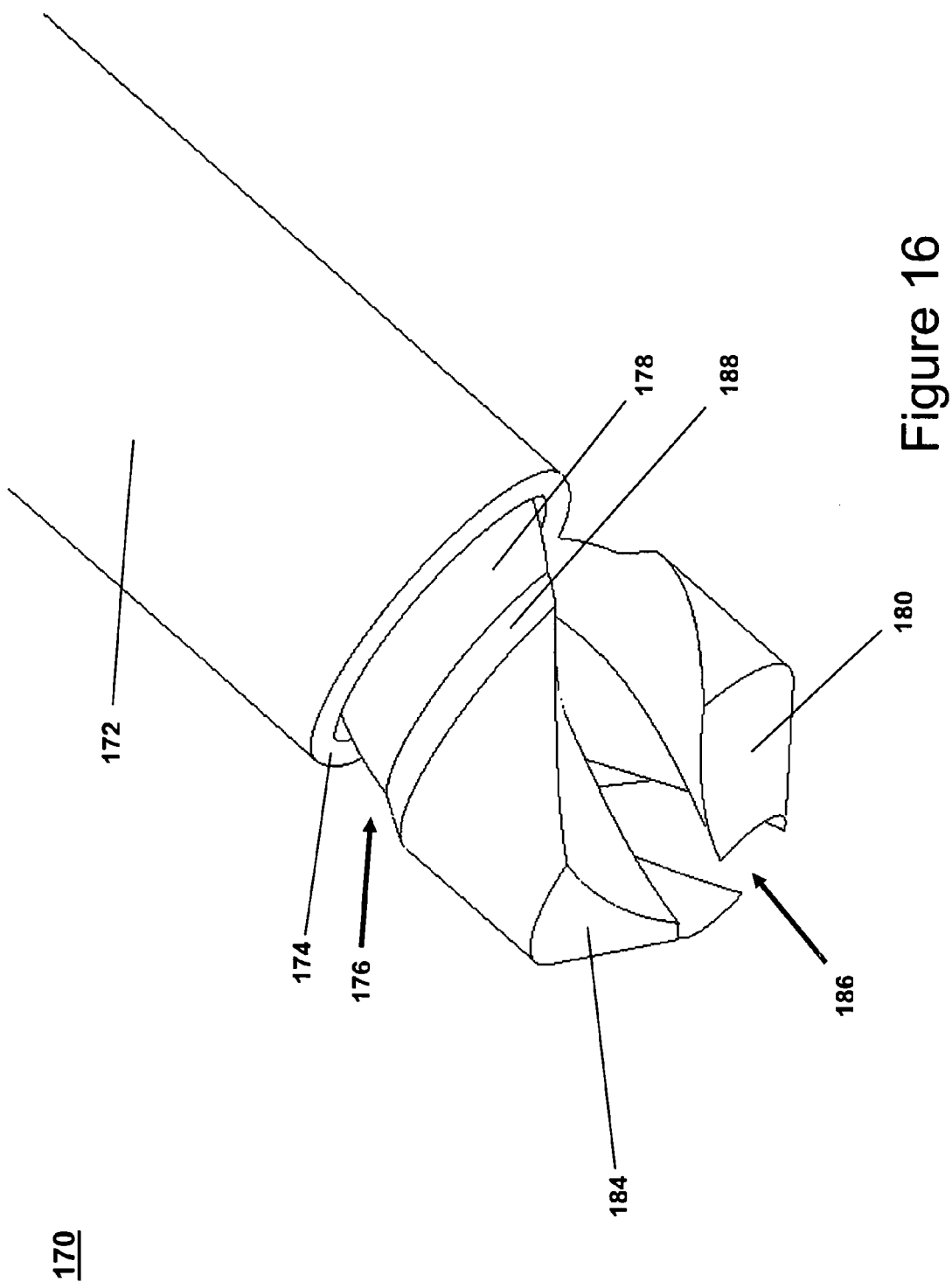
FIG. 16 is an enlarged perspective cutaway view of one embodiment of a boring end of the drill bit assembly shown in FIG. 1 with an inner bit retracted.
Figure 17:
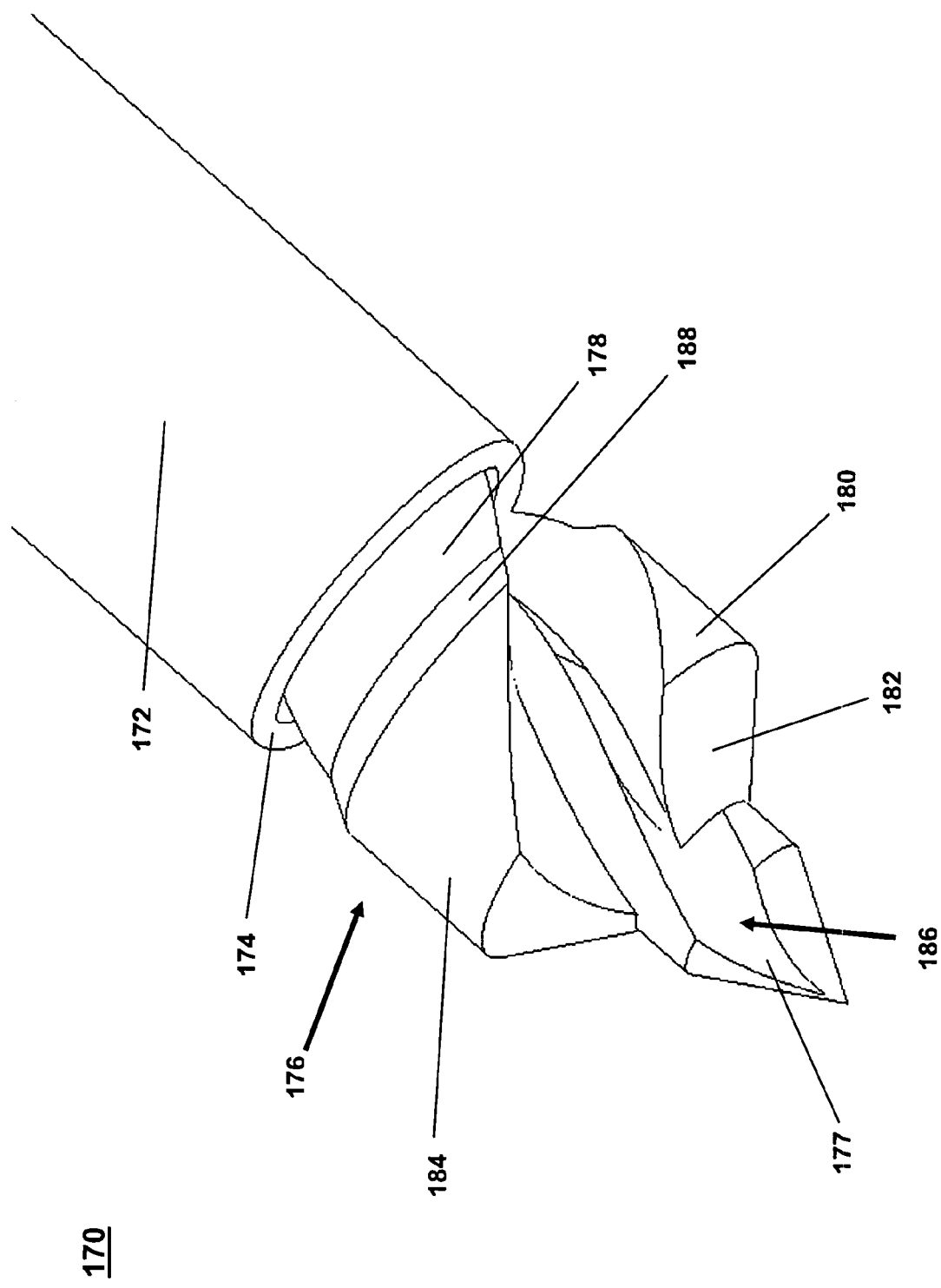
FIG. 17 is an enlarged perspective view of the boring end shown in FIG. 16 with the inner bit extended.

Referring to FIGS. 16 and 17, there is depicted another alternate embodiment of a bone drill bit assembly designated 170 for use with bone drill 10. Assembly 170 includes a non-rotating sheath 172 having a distal end 174, an oversized drill bit 176, and a small inner drill bit 177. Drill bit 176 includes a shank 178 that is sized for receipt in sheath 172, and a head 176 extending from shank 178. Shank 178 and, thus, head 176 are formed of two spiral cutting edges 180 and 184 with a central bore therein. Inner drill bit 177 is formed of 2 spiral cutting edges whose outside bore is sized to fit within the inside bore 186 of drill bit 176. It is inserted into 178 after 178 is inserted into sheath 172. During drilling, head section 184 cuts a larger bore allowing the sheath to follow it into the hole. Once the hole is complete, inner drill 177 is removed. Without the inner drill, head section 184 will collapse and pass through the inner bore of sheath 172 and can be completely withdrawn leaving the sheath in place.

Figure 18:
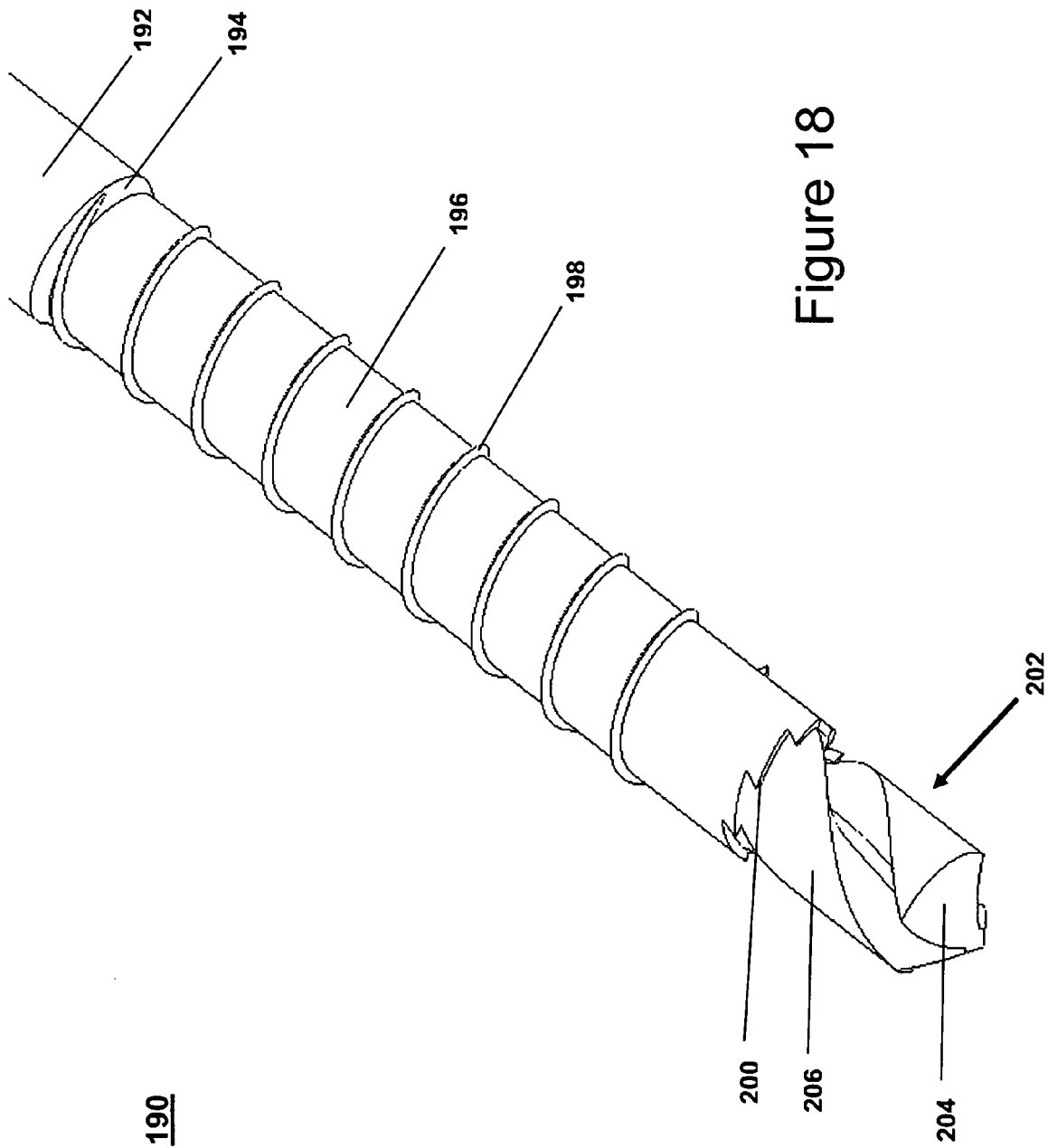
FIG. 18 is an enlarged perspective cutaway view of an alternate embodiment of the drill bit assembly shown in FIG. 1.

Referring to FIG. 18, there is depicted an alternative sheath embodiment 190 wherein sheath 192 has, beginning at an end 194 thereof, an upper shank portion 196 with external threads 198 thereon. End teeth or serrations 200 are provided on shank 198. A drill bit 202 includes cutting spirals 204, 206 configured to extend through sheath 196. This alternate design controls depth feed rate. By controlling the drill/sheath speed (e.g. variable speed control) or the sheath speed alone (e.g. ring gear brake), the user knows how fast the drill bit plunges into the bone based on the thread pitch of external threads 198.

Figure 19:
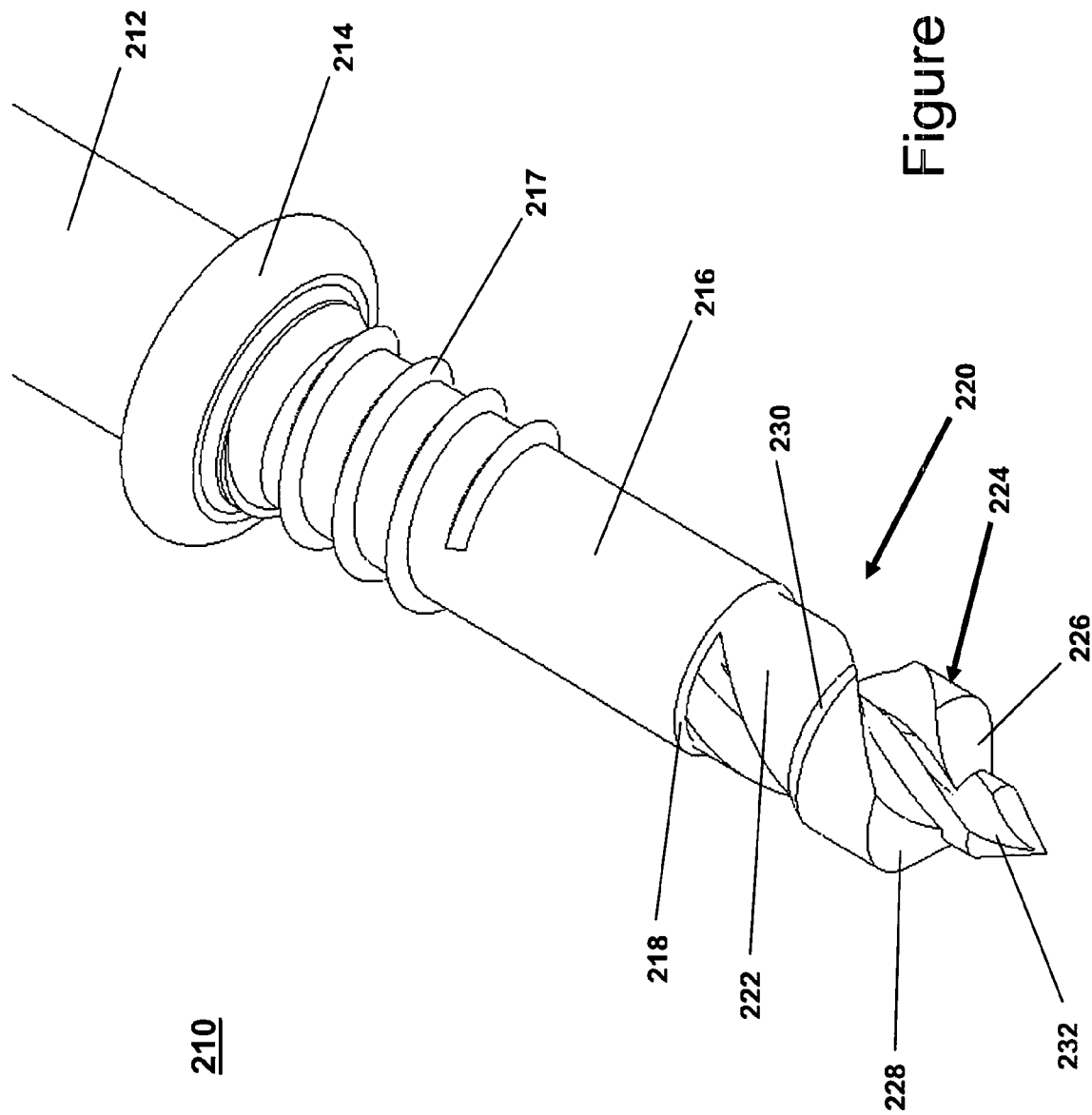
FIG. 19 is an enlarged perspective cutaway view of an alternate embodiment of the drill bit assembly shown in FIG. 1.

Referring to FIG. 19, there is depicted another alternative embodiment of a sheath assembly generally designated 210. In this embodiment, sheath assembly 210 includes a proximal tubular sheath portion 212 and a distal tubular sheath portion 216. An oversized drill bit 220 is shown extending from non-serrated end 218 of distal tubular sheath portion 216. Oversized drill bit 220 includes a shank 222 with a head 224 extending from shank 222 via a taper portion 230. First and second spiral cutting edges 226, 228 are oversized at head portion 224 and expand after exiting sheath 216. Cutting edges 226, 228 include a central bore that allows an inner drill bit 232 to extend therethrough.

Sheath 216 includes external threads 217 in like manner to external threads 198 of sheath 196 of sheath assembly 190 shown in FIG. 18. A radially extending stop 214, however, is provided between proximal and distal sheath portions 214, 216. Stop 214 is used as a depth control. Offset to the drill bit to sheath is a control mechanism on the drill head. Once the sheath's stop bottoms out on the outer surface on the bone, the drill will not be able to plunge any deeper. If it isn't deep enough, the doctor would back up the drill, adjust the depth setting, re-engage and finish drilling to the proper depth.

A bone curette/cavity drill may be used with a bone drill, particularly during the above described procedures wherein the drill has been removed and the access sheath/conduit remains in the bone. The curette can have a four-blade cutter that attaches and rotates with bone drill 10. It should be appreciated that the curette may have more or less blades as desired. Bone drill 10 is adapted to receive replaceable bits/tools. This may be accomplished by providing a releasable catch or the like.

Referring to FIGS. 20-28, in an alternate embodiment similar to that described with regard to FIGS. 1-13, a bone drill 410 is provided in accordance with the principles of the present disclosure. Bone drill 410 includes a drill body 412 and a drilling assembly 420. Bone drill 410 is configured for hole boring in bone, as described herein, and various components of bone drill 410, may be formed of a radiolucent material. It is envisioned that bone drill 410, or components thereof, are disposable after a vertebral body or sacral body procedure. Bone drill 410 and its components may also be reused. It is further envisioned that bone drill 410 is formed by radiolucent and radio opaque materials, similar to bone drill 10. Bone drill 410 may also include radio opaque markers for aligning the shaft, sheath and drill bit, similar to radio opaque markers 64 described with regard to bone drill 10.

Bone drill 410 is adapted to create or drill a bore in the bone, and to introduce and temporarily leave a tube, tubular sheath or the like of drilling assembly 420 in the bore. It is contemplated that the tubular sheath is configured to allow an instrument, component, tool or the like to pass therethrough and provide access to an area at or adjacent to the distal end of the tubular sheath.

Drilling assembly 420 includes a sheath assembly 456 having a sheath 457 and a proximal end terminating in a drive head 460. Drive head 460 includes multiple projections on an outer periphery thereof. Sheath 457 has a distal end. It is envisioned that the distal end of sheath assembly 456 may be serrated or include drilling teeth. Drilling assembly 420 includes a drill bit 458, similar to that described above. It is contemplated that sheath 457 is fabricated from metal.

Body 412 is formed of a first portion 425 and a second portion 427. It is contemplated that portions 425, 427 may be symmetric halves, offset, non-symmetric, etc. Body 412 defines a handle 414, a drive housing 416 and a head portion 418. A connecting portion 440 is defined between handle 414 and motor housing 416. A neck 448 is defined between motor housing 416 and head portion 418.

Handle 414 defines a tubular body 424, which has a palm area 426. Body 424 also includes an opening 431 (FIG. 25) in second portion 427 through which a switch 430 extends. It is contemplated that switch 430 may comprise a button configuration, which may include a trigger style for variably controlling the rotational speed of bone drill 410. It is further contemplated that switch 430 facilitates a reversing rotation.

Figure 25:
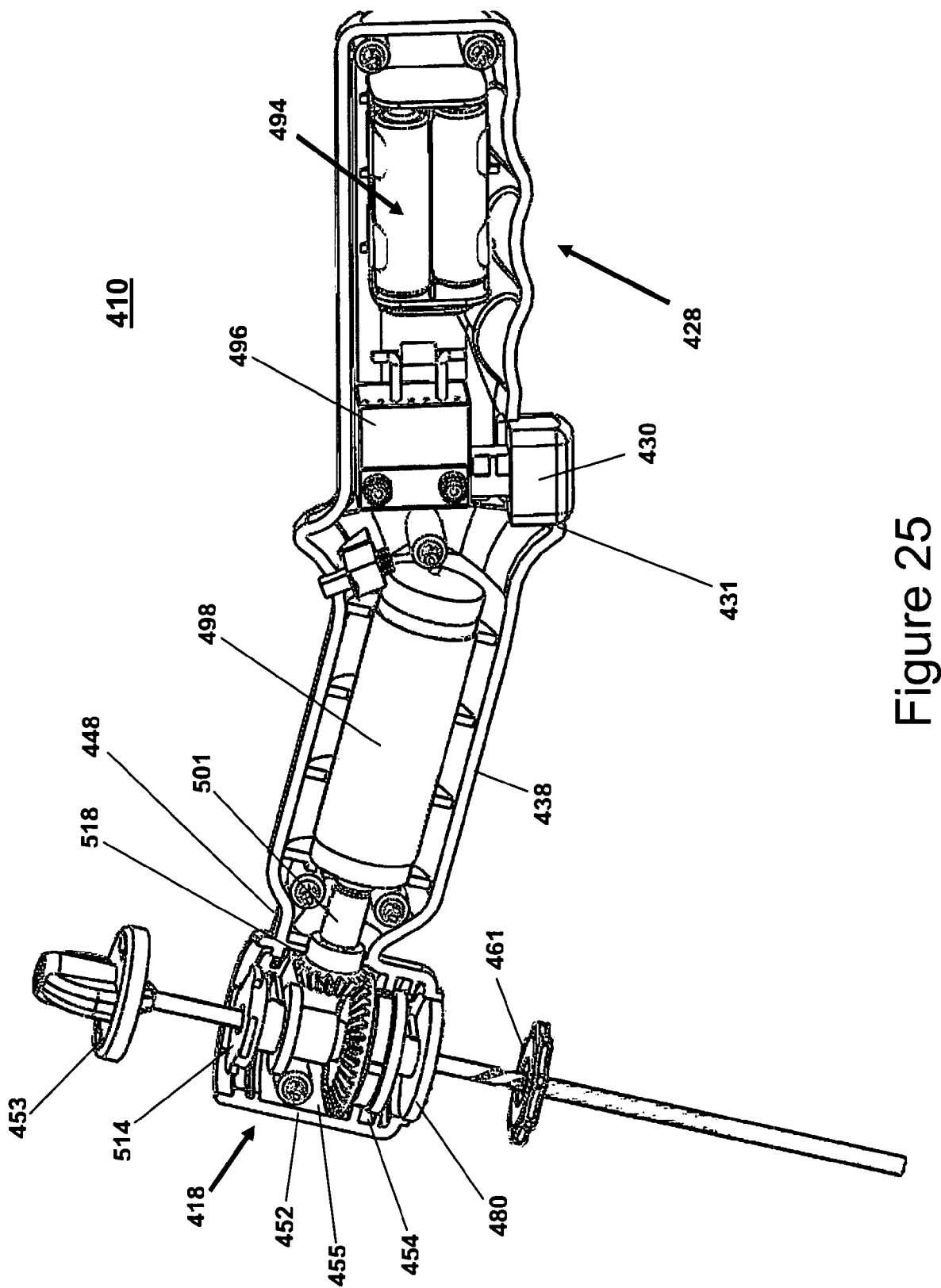
FIG. 25 is a side perspective view of the bone drill shown in FIG. 20 with a cover removed.
Figure 26:
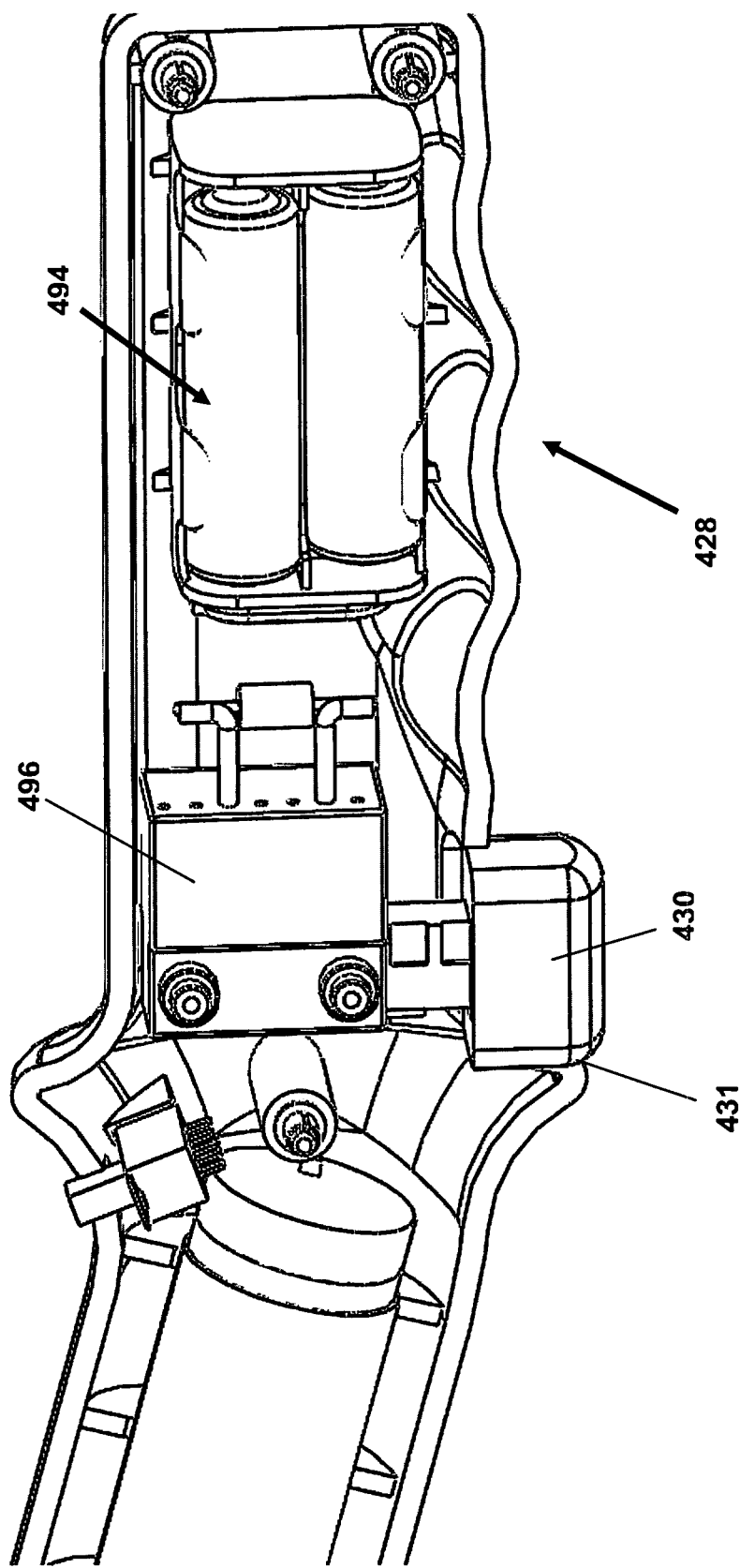
FIG. 26 is an enlarged cutaway view of a rear portion of the bone drill shown in FIG. 25.

As shown in FIGS. 25 and 26, button 430 is operatively coupled with a speed controller 496 for actuation of drill 410. A finger grip area 428 is disposed adjacent to button 430, which includes three finger indentions that accommodate fingers of a user's hand for gripping handle 414. Portions 425, 427 form an interior cavity 492 in which a battery 494 is housed. Body 412 also includes a projection 442, similar to that described.

Drive housing 416 includes a motor assembly 498 disposed within tubular body 438. Motor 498 is electrically coupled to batteries 494 and speed controller 496 such that depressing trigger 430 actuates controller 496. It is contemplated that button 430 may be variably depressed to increase drill speed.

Head portion 418 has a body 452 including a drill bit handle 453 and a bottom support 454. Body 452 defines an interior cavity 455 that supports the drilling assembly drive gearing.

Motor assembly 498 is operatively coupled to an output shaft 501 for rotation thereof via gearing. Output shaft 501 is retained for rotation in a mount 518 formed on the inside of neck 448 (see FIGS. 27 and 28). A bevel gear 502 is connected to the output shaft 501 for meshing/engaging with the drilling assembly gearing in head 418.

Figure 27:
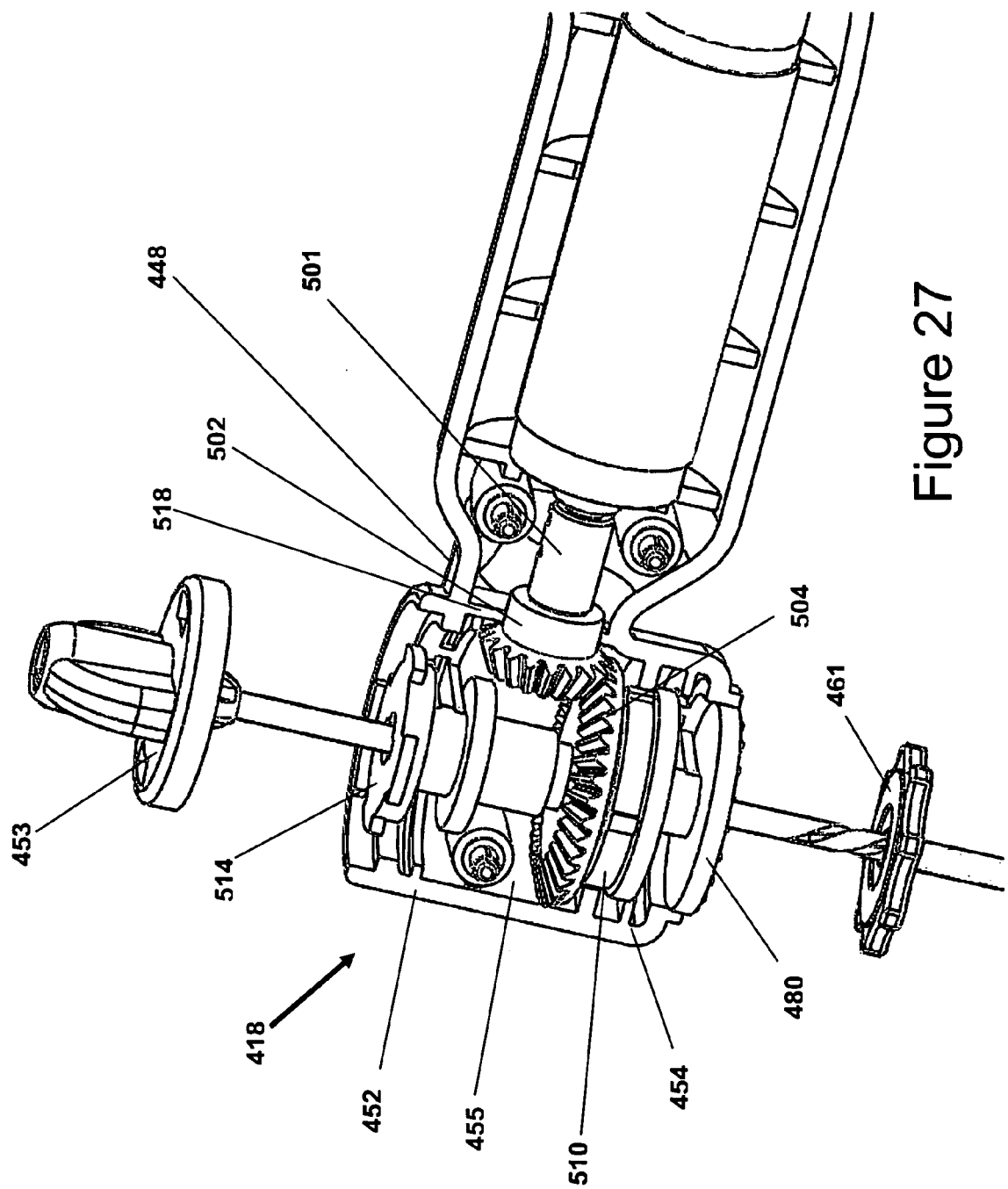
FIG. 27 is an enlarged cutaway view of the head portion shown in FIG. 25.
Figure 28:
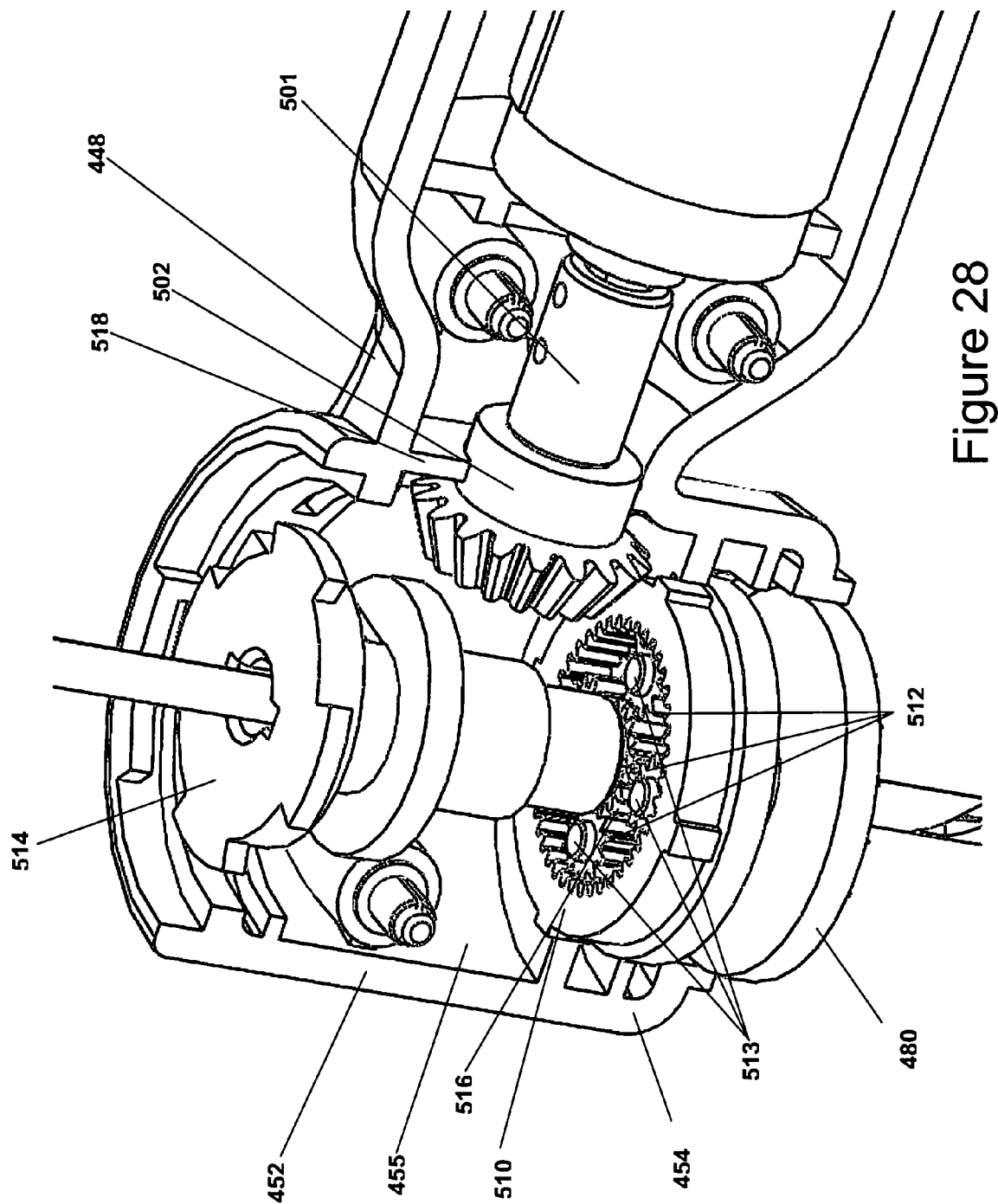
FIG. 28 is an enlarged cutaway view of the head portion shown in FIG. 27 with a gear removed.

As shown in FIGS. 27 and 28, bevel gear 502 meshes with an input gear 504 of the drilling assembly gearing. Input gear 504 is retained about a support cylinder 514, which is connected to drill bit 458. Input gear 504 includes teeth on an outer radial periphery thereof that meshes with the teeth of bevel gear 502. A gear 516 is mounted with support cylinder 514. Thus, as bevel gear 502 rotates input gear 504, input gear 504 rotates support cylinder 514 and gear 516, which rotates planetary gears 512. As shown in FIGS. 27 and 28, lower gear ring 510, which includes teeth on the radially inside periphery thereof, is held stationary inside head 418. A drive cylinder 508 carries gears 512 via respective gear shafts 513, which are situated radially inside lower gear ring 510. Gears 512 are rotated by the teeth of gear 516. As they rotate, they process around lower gear ring 510, which is held stationary, causing cylinder 508 to rotate. Gear 516 rotates drill bit 458. Drive cylinder 508 is adapted to engage and drive (rotate) sheath assembly 456 of drilling assembly 420.

An end 480 of drive cylinder 508 is adapted to frictionally engage a surface 461 of drive head 460. Surface 461 is formed of rubber or the like to facilitate frictional engagement with end 480. Thus, when end 480 is caused to rotate with drive cylinder 508, as described, end 480 engages surface 461 and sheath 457 rotates thereby effecting reaming the bore started by and/or being cut by drill bit 458. Thus, a bore is created that allows sheath 457 to extend therein. Thus, one mode of driving sheath assembly 420 is by friction via a friction plate or surface 461.

Drill bit handle 453 is affixed to drill bit 458 and is used to position the drill bit in the support cylinder 514 and lock it in place. Splines on the lower section of handle 453 are inserted into corresponding grooves in support cylinder 514 providing a radial interface the carries the rotational load from the drill bit to the support cylinder. Features on the handle 453 slide over and lock onto the 2 of the 4 tangs extending radially on the outside perimeter of the support cylinder 514 thus affixing drill bit 458 and drill bit handle 453 to support cylinder 514.

Figure 22:
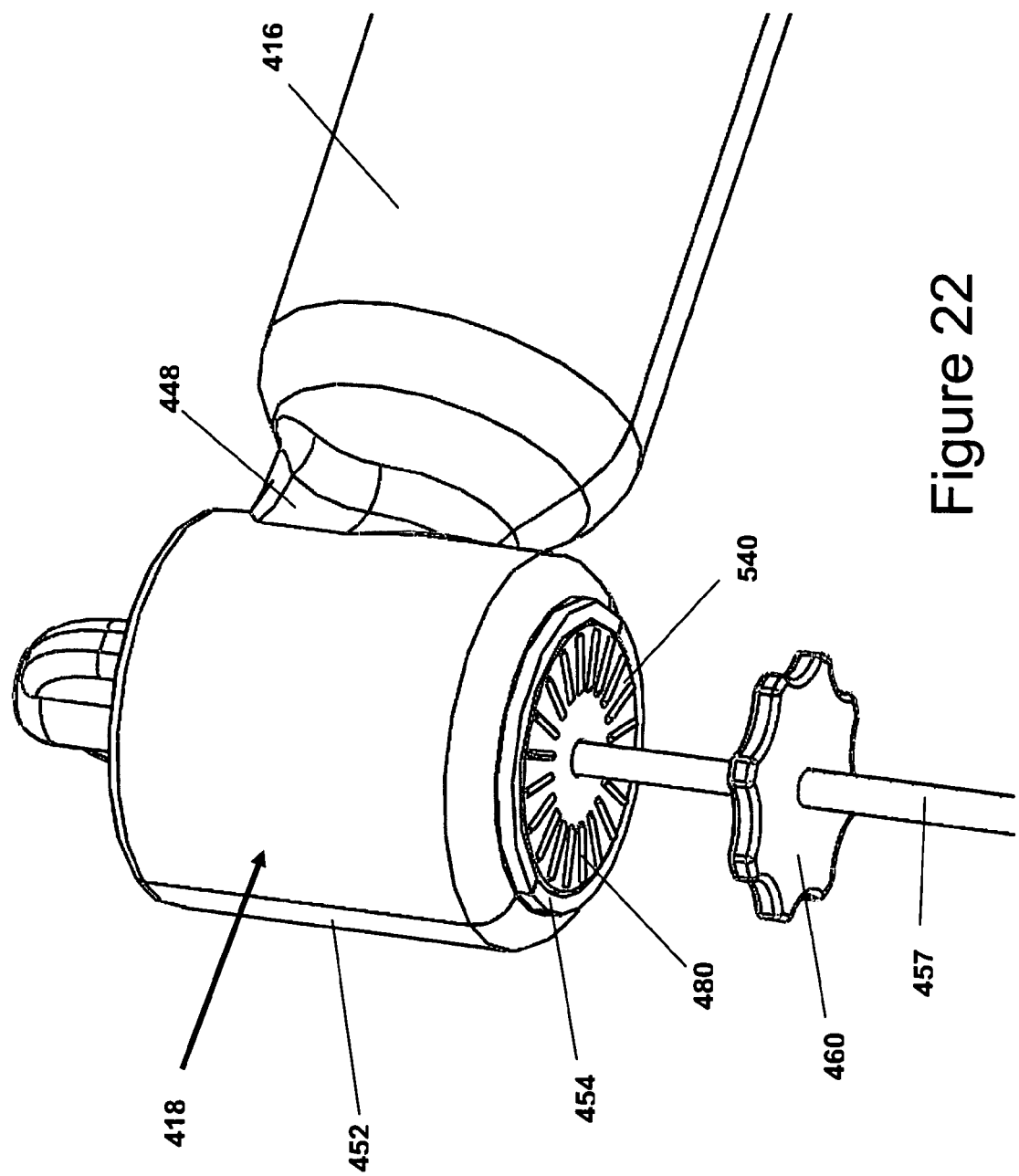
FIG. 22 is an enlarged bottom perspective cutaway view of a head portion of the bone drill shown in FIG. 20.

Cutting sheath 457 is, thus, not driven initially. It remains stationary to guide drill bit 458 when starting a hole. As drilling progresses, drive head 460 is frictionally engaged by drive cylinder 508 such that the sheath assembly is subsequently (after the start of drill bit rotation) rotated. This cuts a hole large enough for the sheath to follow the drill bit into the bone. To facilitate a robust frictional engagement between surface 461 and end 480, end 480 includes a plurality of notches 540 (FIG. 22). The configuration of bone drill 410 can advantageously provide a one step bone access device that positions a user's hand a greater distance away from a radiation source employed with bone drill 410, thereby increasing safety and minimizing injury to the user.

Figure 20:
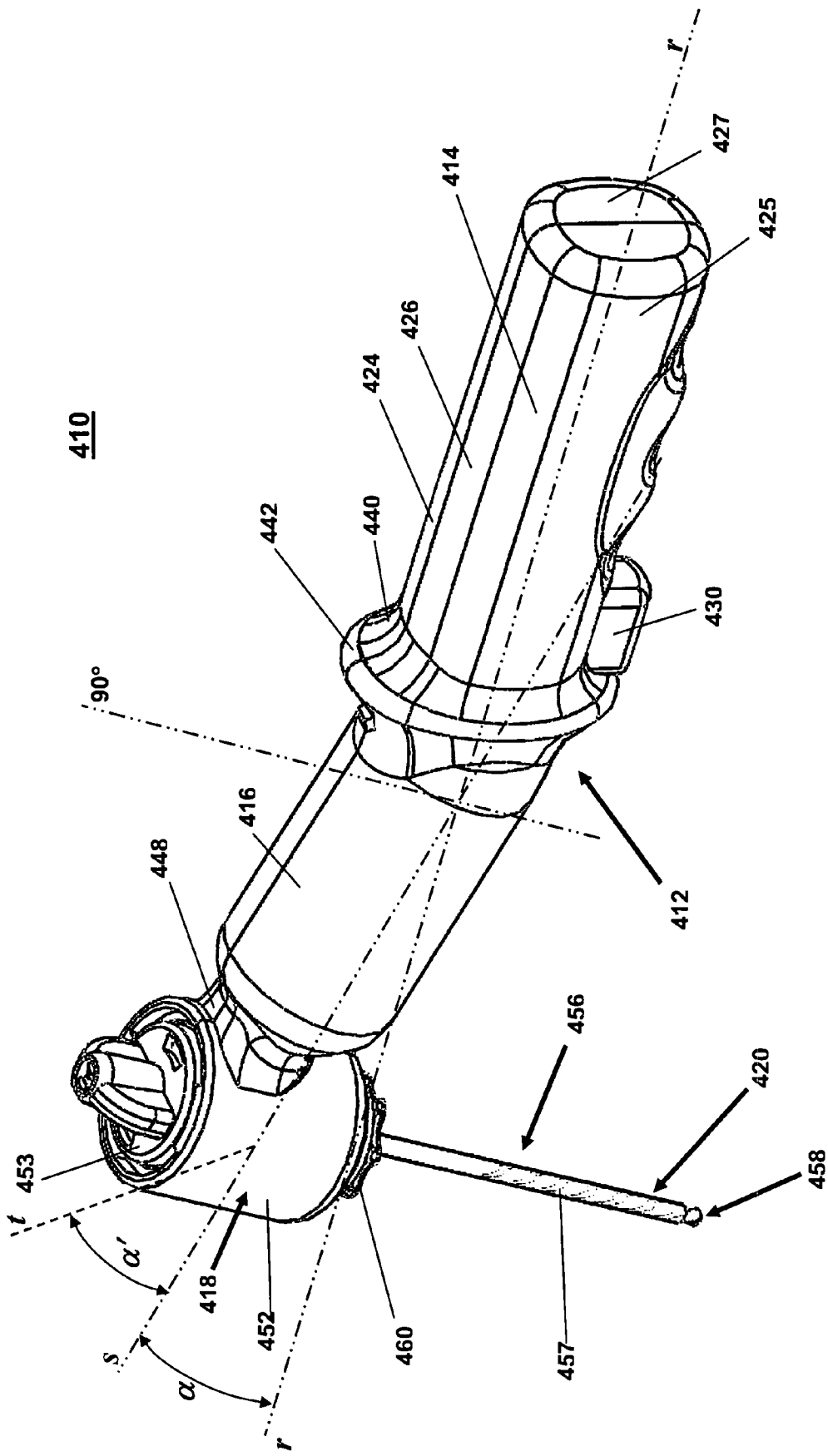
FIG. 20 is a perspective view of an alternate embodiment of the bone drill constructed in accordance with the principles of the present invention.
Figure 21:
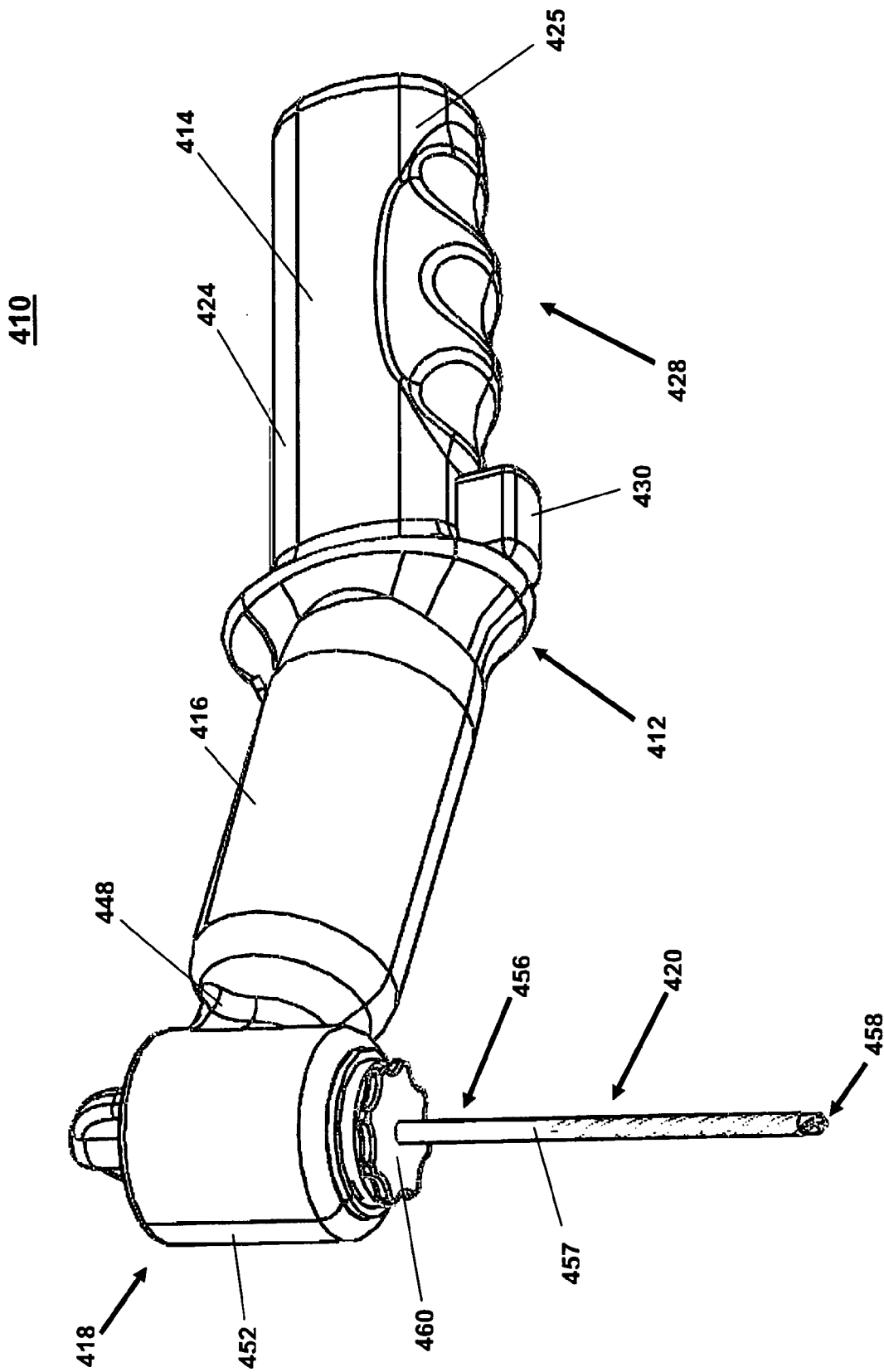
FIG. 21 is a bottom perspective view of the bone drill shown in FIG. 20.

As shown in FIG. 20, handle portion 414 defines a longitudinal axis r. Drive portion 416 defines a longitudinal axis s, which is co-axial with a longitudinal axis t defined by head portion 418. Longitudinal axes s, t, and correspondingly drive portion 416 and head portion 418, are offset from longitudinal axis r, corresponding to handle portion 414. Longitudinal axes s, t are disposed at an angular orientation a relative to longitudinal axis r. It is contemplated that a is in a range of 0 to 45 degrees. It is further contemplated that α is most desirably 15 degrees. This advantageous configuration provides a safe distance between a physician and radiation emitted during a procedure employing bone drill 410.

Longitudinal axis s of drive portion 16 may also be separately offset and disposed at angular orientation α from longitudinal axis r of handle portion 14, relative to longitudinal axis t of head portion 18, such as longitudinal axis t being disposed at angular orientation α' and shown in phantom. Longitudinal axis s of drive portion 16 may be coaxial with longitudinal axis r of handle portion 14, and longitudinal axis t of head portion 18 may be offset from the drive/handle portions, or co-axial with one and offset from the other axis. It is contemplated that the various and multiple offset and angular relative configurations of handle portion 14, drive portion 16 and head portion 18 are provided via fixed fabrication of the component parts, pivoting components, ratcheting components, etc. and various combinations of the same. It is further contemplated that these attachments are assembled as is known to one skilled in the art.

In operation, a bone drill, similar to bone drill 10 and bone drill 410 described herein, is employed with a method for treating bone of a vertebral body or a sacral body. The components of bone drill 410, for example, are fabricated, properly sterilized and otherwise prepared for use. Bone drill 410 is provided with handle portion 414, drive portion 416 and head portion 418 in a configuration that provides a safe distance between a physician and radiation emitted during the procedure, as described above.

Head portion 418 includes radiolucent markers disposed in a configuration to facilitate alignment of sheath 457 with bone (not shown) of the vertebral body. During fluoroscopy, an area is exposed to radiation, which includes bone drill 410 and the bone of the vertebral body. The exposure of radiation to bone drill 410 and the radiolucent markers allows the user to identify the location of sheath 457 and drill bit 458 relative to the targeted bone. This configuration facilitates alignment, via the radiolucent markers, for cutting the bone while protecting the user by maintaining the offset angular orientation of bone drill 410, discussed above. A guard 710, discussed herein, may also be used during the procedure.

Drill bit 458 engages the bone and rotates via motor 498 to bore a cavity in the bone. Sheath 457 is driven into engagement with the bone to further define the cavity in the bone. After a cavity is created, according to the requirements of a particular treatment procedure, the targeted bone area is treated. In one embodiment, the step of treating includes treating vertebral compression fractures, which employs bone drill 410. Bone drill 410 allows the operator to place an access conduit/sheath/needle into a fractured vertebral body in a single step. Once the access conduit/sheath/needle is positioned in the fractured vertebral body, various devices including the bone curettes described can be inserted through the access conduit/sheath/needle into the bone. The bone curette, which has been configured to be inserted into the drill, creates a cavity in the fractured bone. Next, a bone cement mixture is instilled through the access conduit/sheath/needle. Cavity creation with the curette decreases the risk of cement leakage and also allows the placement of a greater cement volume.

In another embodiment, the step of treating includes treating sacral fractures, which employs bone drill 410. Bone drill 410 allows the operator to place an access conduit/sheath/ needle into the fractured sacrum in a single step. Once the access conduit/sheath/needle is positioned in the fractured sacrum, various devices including the bone curettes described can be inserted through the access conduit/sheath/needle into the sacrum. The bone curette, which as been configured to be inserted into the drill, creates a cavity in the fractured bone. Next, a bone cement mixture is instilled through the access conduit/sheath/needle. Cavity creation with the curette decreases the risk of cement leakage and also allows the placement of a greater cement volume.

In another embodiment, the step of treating includes treating lytic tumor deposits in the bone, which employs bone drill 410. Bone drill 410 allows the operator to place an access conduit/sheath/needle into the lytic bone tumor deposit in a single step. At that point a biopsy can be obtained. Once the access conduit/sheath/needle is positioned in the lytic tumor, various devices including the bone curettes described are configured to be inserted into the drill and can be inserted through the access conduit/sheath/needle into the tumor deposit. The curette can be used to create a cavity in the lytic tumor deposit. Next, a bone cement mixture is inserted through the access conduit/sheath/needle into the lytic tumor deposit. Cavity creation with the curette decreases the risk of cement leakage and also allows placement of a greater cement volume.

In another embodiment, the step of treating allows the operator to place an access conduit/sheath/needle into bone in order to obtain bone biopsy specimens or to obtain access for bone infusions. In another embodiment, the step of treating includes bone drill 410, which can be used with different bits (such as various screwdriver bits) to facilitate/perform various surgical procedures requiring such tools that need to be used with fluoroscopic guidance.

In another embodiment, the step of treating may include the step of irrigating the cavity, suctioning the cavity and/or inflating the cavity with appropriate medical instrumentation as is known to one skilled in the art. A fluid-transfer device may be provided and used as a one-step device for simultaneously irrigating and aspirating material from the cavity. The fluid-transfer device may also be used for instilling bone cement into the cavity. The fluid-transfer device allows a greater and more uniform cement distribution by simultaneously instilling cement and aspirating the cavity. This configuration creates a preferred pathway that allows the cement to follow the path of least resistance resulting in more even cement distribution within the bone. Also, the step of treating may include various devices used for inflating the cavity.

Figure 29:
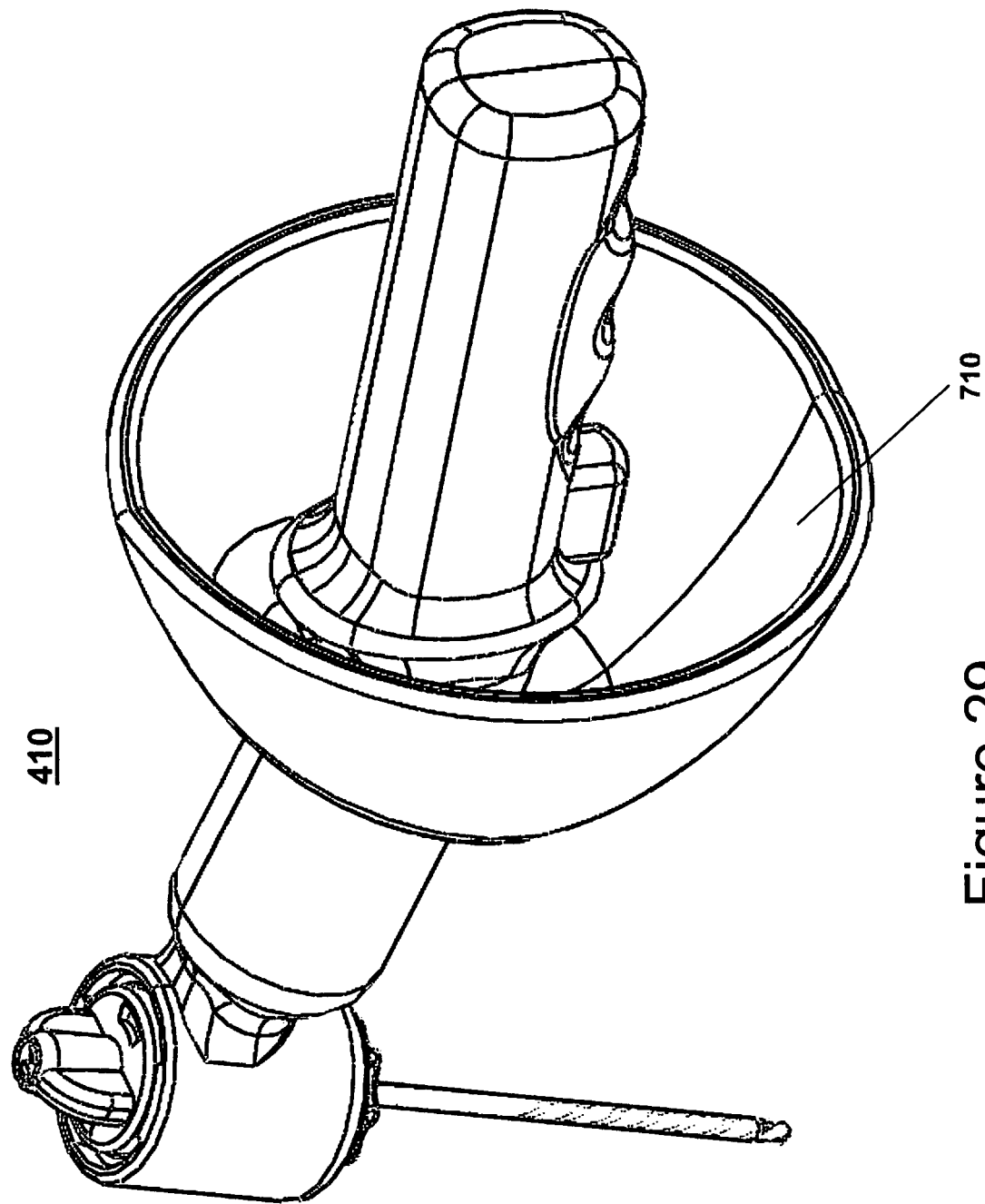
FIG. 29 is a perspective view of an alternate embodiment of the bone drill shown in FIG. 20.
Figure 30:
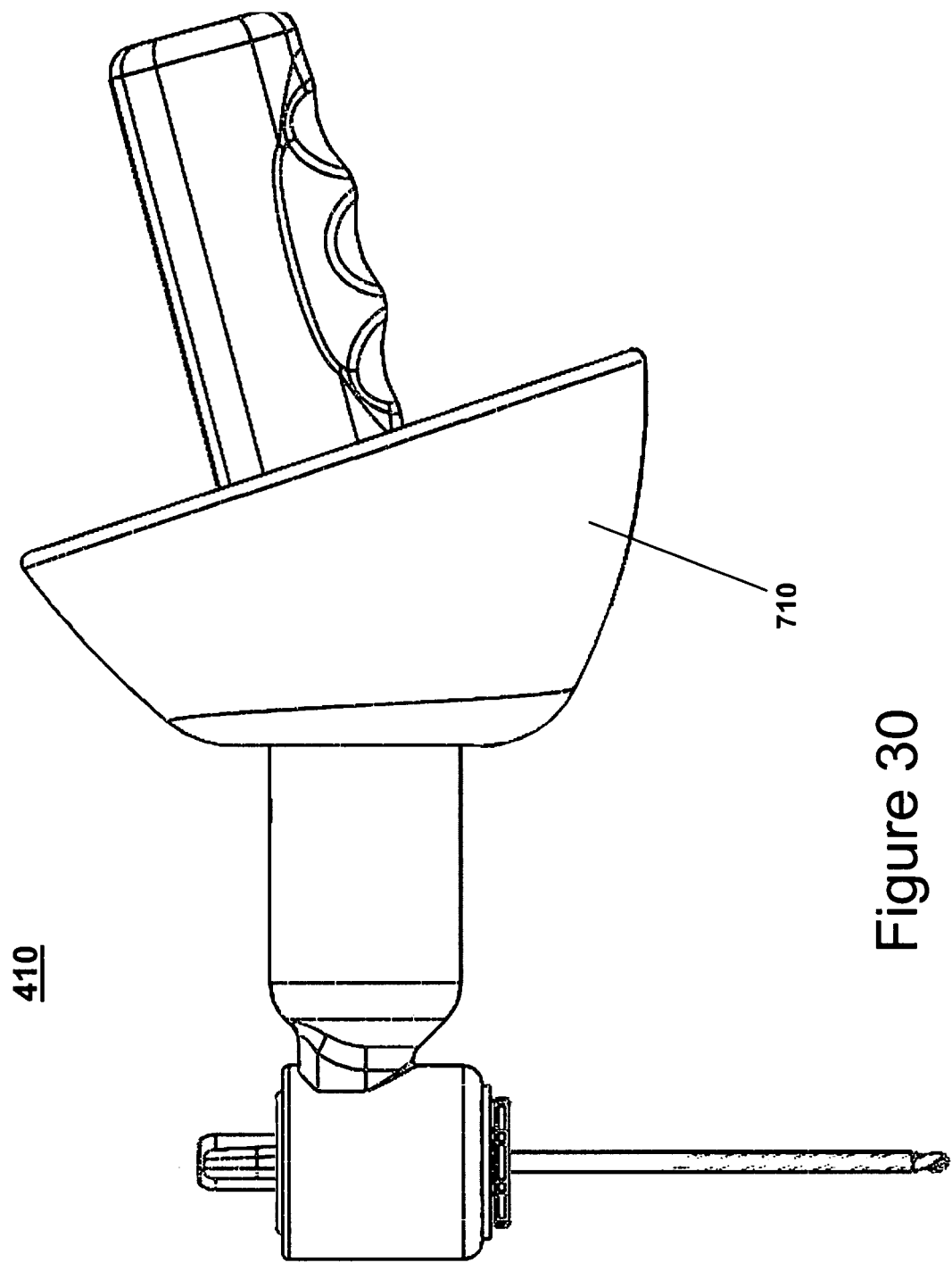
FIG. 30 is a side view of the bone drill shown in FIG. 29.
Figure 31:
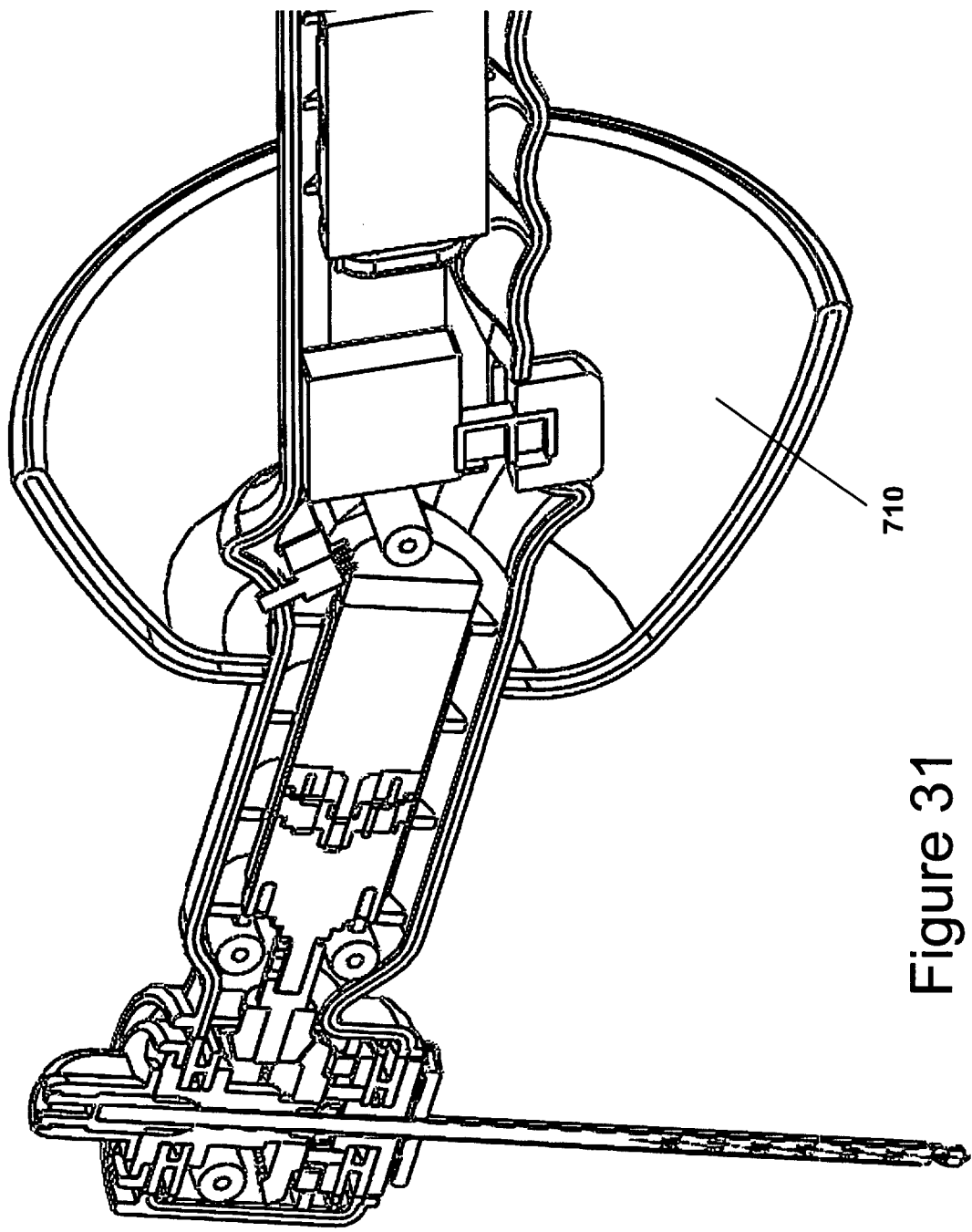
FIG. 31 is a perspective view, in cross section of the bone drill shown in FIG. 29.

Referring to FIGS. 29-31, an alternate embodiment of bone drill 410, similar to that described above, includes a guard 710. Guard 710 is configured to protect a user's hand from radiation. It is contemplated that guard 710 is integral to bone drill 410 or alternatively detachable. Guard 710 is designed to protect the user's hand from both primary beam and scatter radiation by centering inferiorly and laterally. Guard 710 may fabricated from flexible or rigid radio-protective materials, such as lead, tin, etc.

Bone drill 410 is relatively rotatable to guard 710 so that the user can rotate guard 710 to different positions, depending on the concentration of the primary beam and scatter radiation, and the origination of radiation. Guard 710 can be separate and permanently affixed to the bone drill 410. Alternatively, guard 710 could be snapped in place, slidably mounted in a flexible arrangement of thin shielding material such as lead, tin, etc., or in a boot or sleeve, wrapped in a fabric such as nylon, etc., and mounted with Velcro fasteners in a configuration that allows the user to wrap it around the hand and drill 410.

Figure 37:
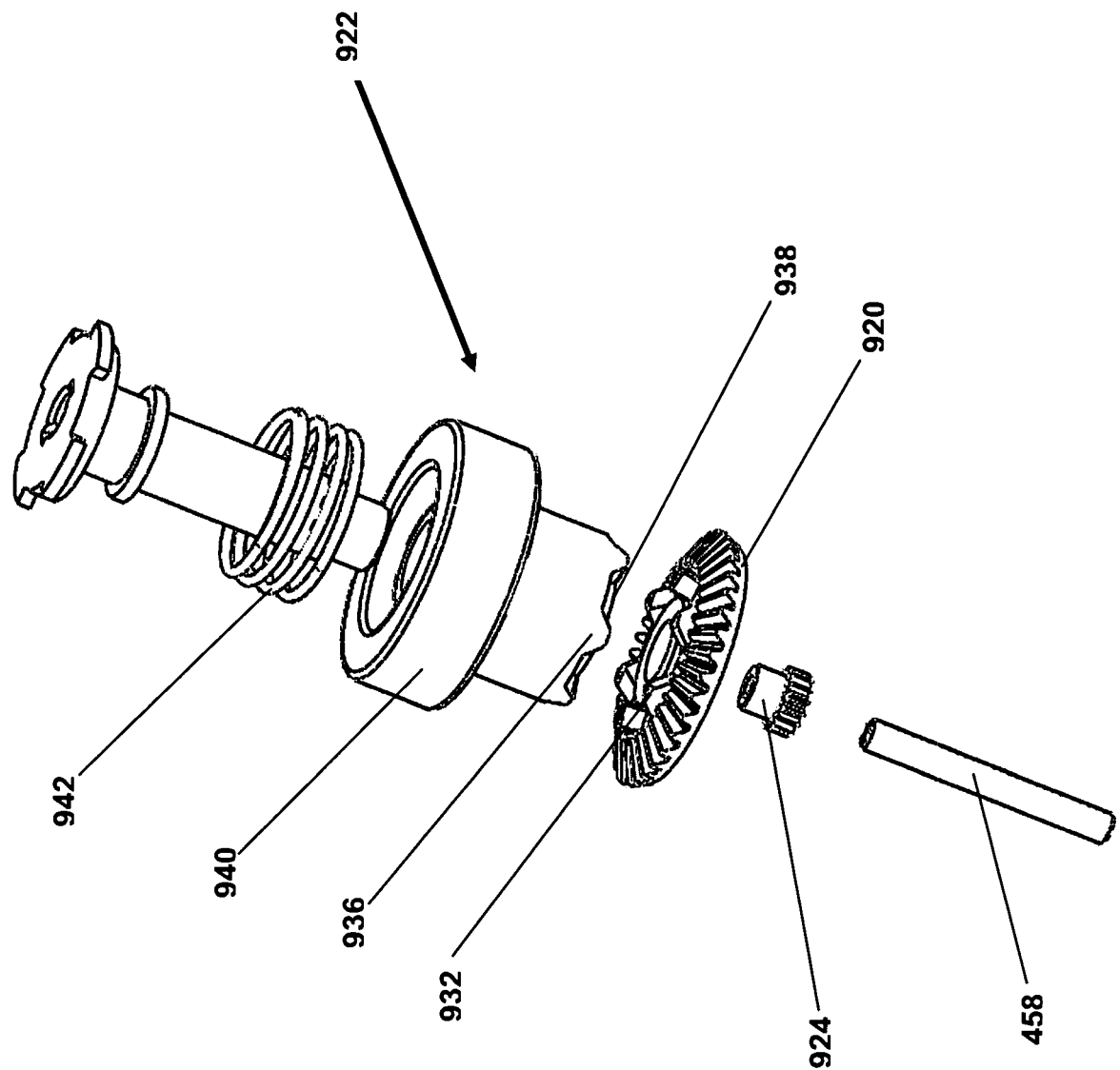
FIG. 37 is an enlarged perspective exploded view of separated components of the head portion shown in FIG. 35.
Figure 38:
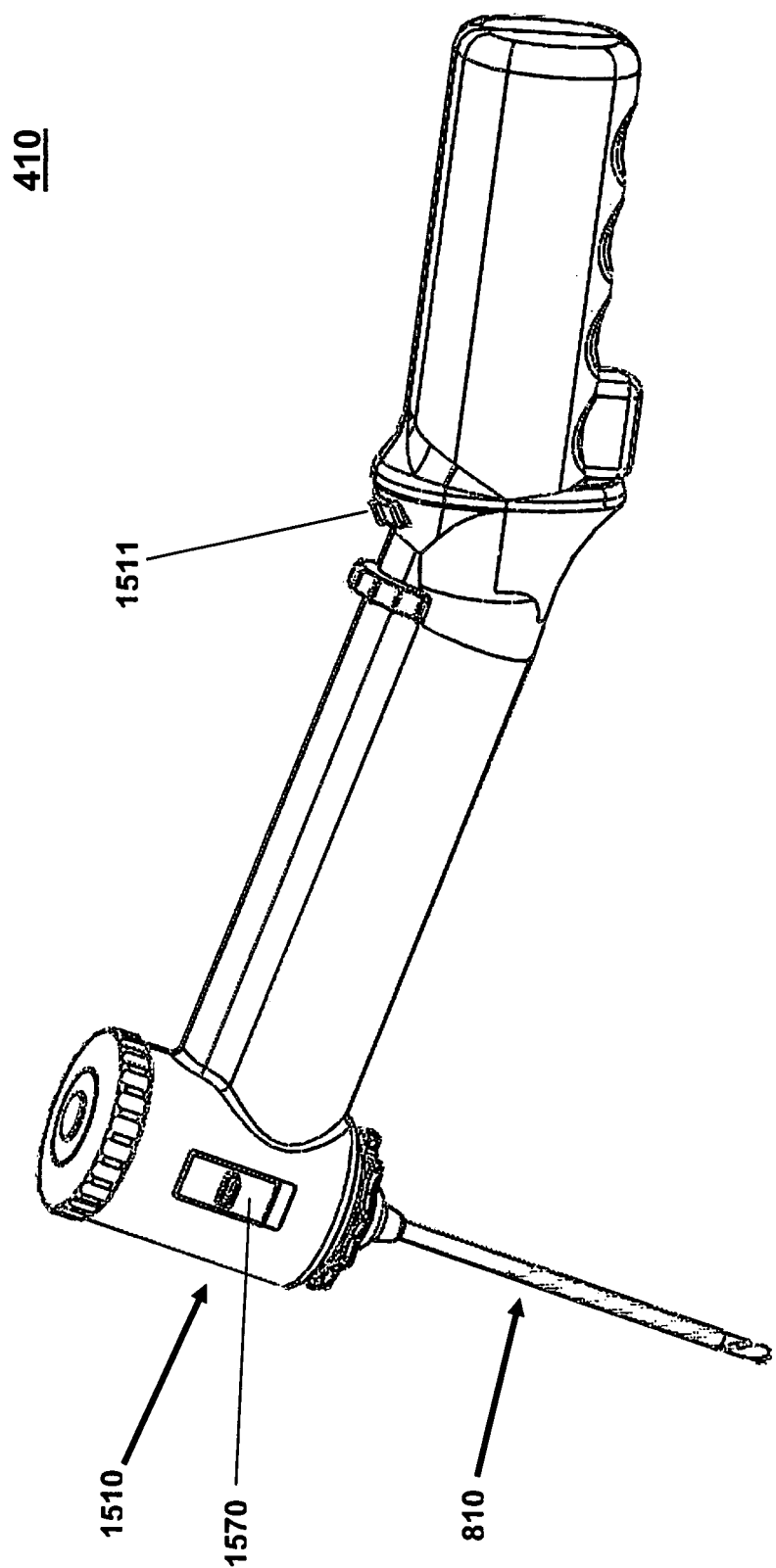
FIG. 38 is a side perspective view of an alternate embodiment of the bone drill shown in FIG. 20 constructed in accordance with the principles of the present invention.
Figure 39:
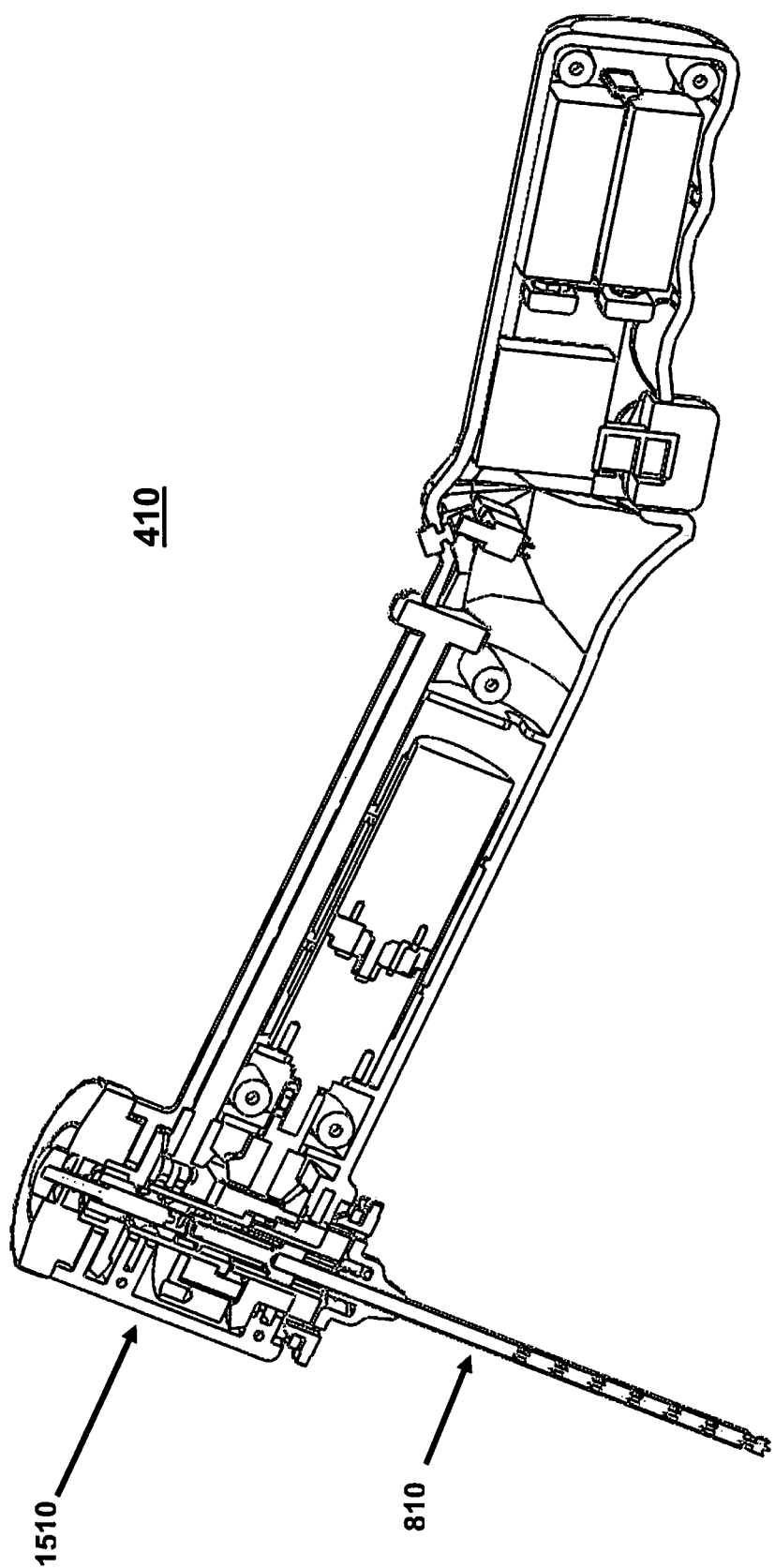
FIG. 39 is a side perspective sectional view with cover removed of the bone drill shown in FIG. 38.
Figure 40:
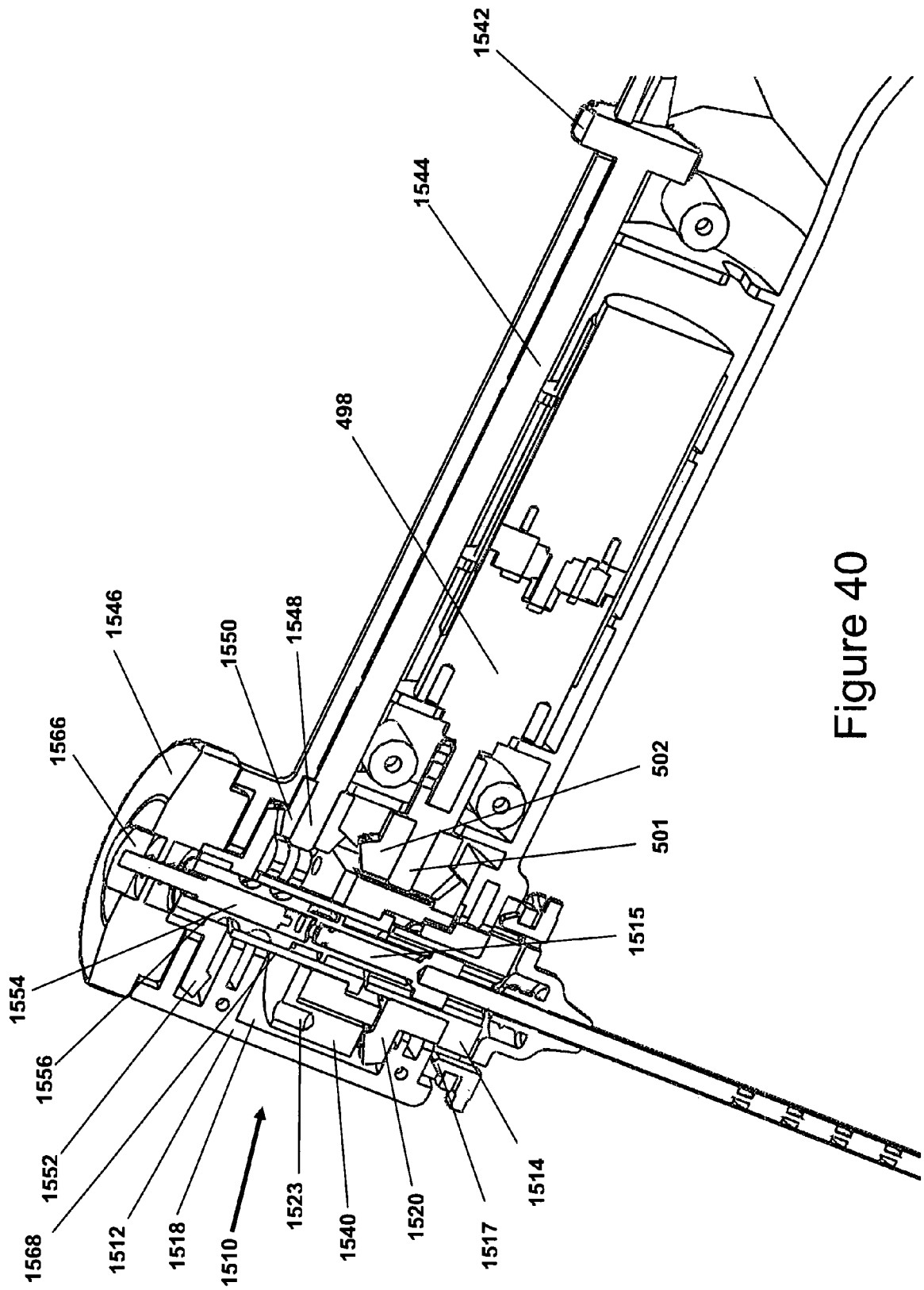
FIG. 40 is an enlarged side perspective view, in cross section of the head portion shown in FIG. 38.
Figure 41:
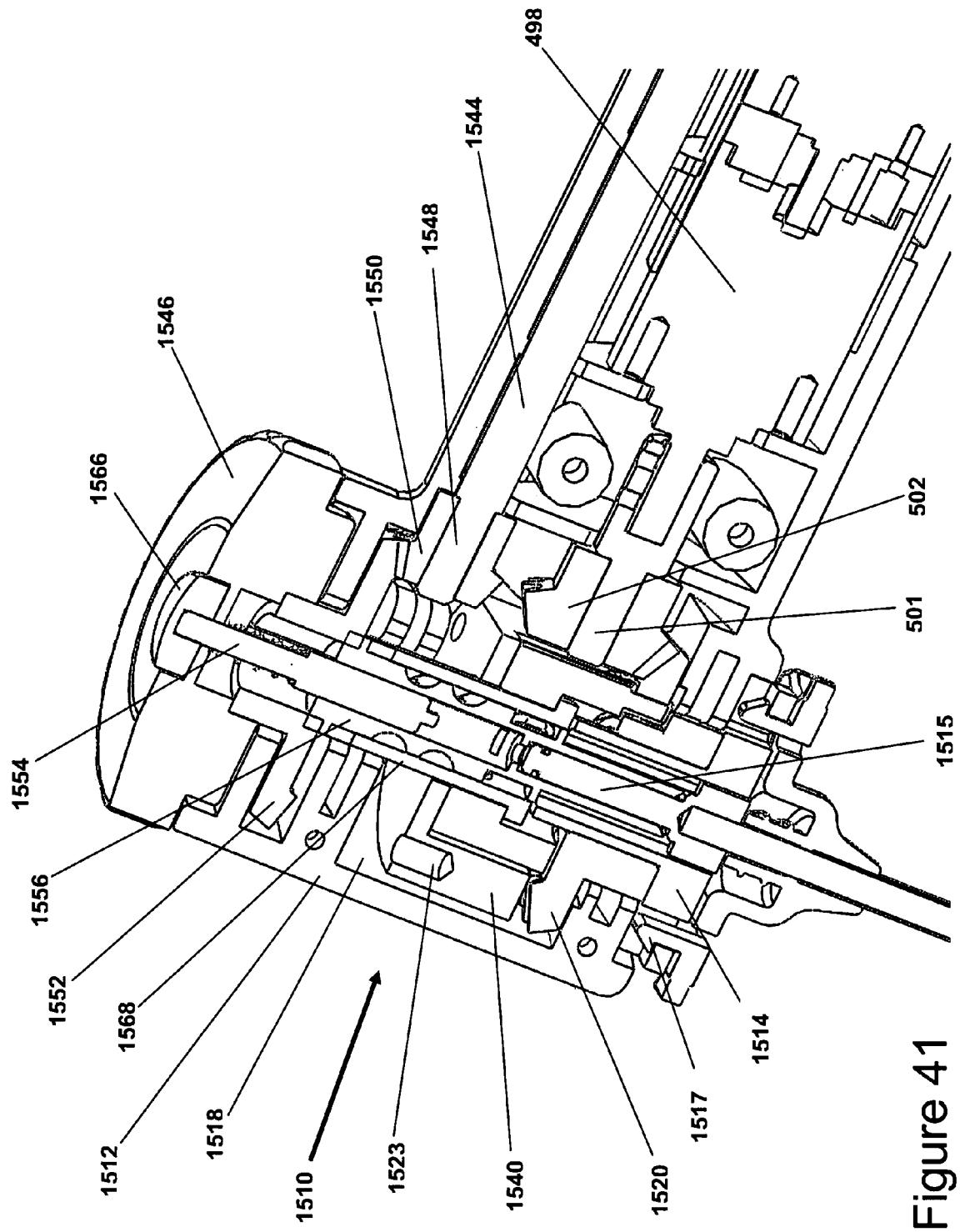
FIG. 41 is an enlarged side perspective view, in cross section of the head portion shown in FIG. 38.
Figure 42:
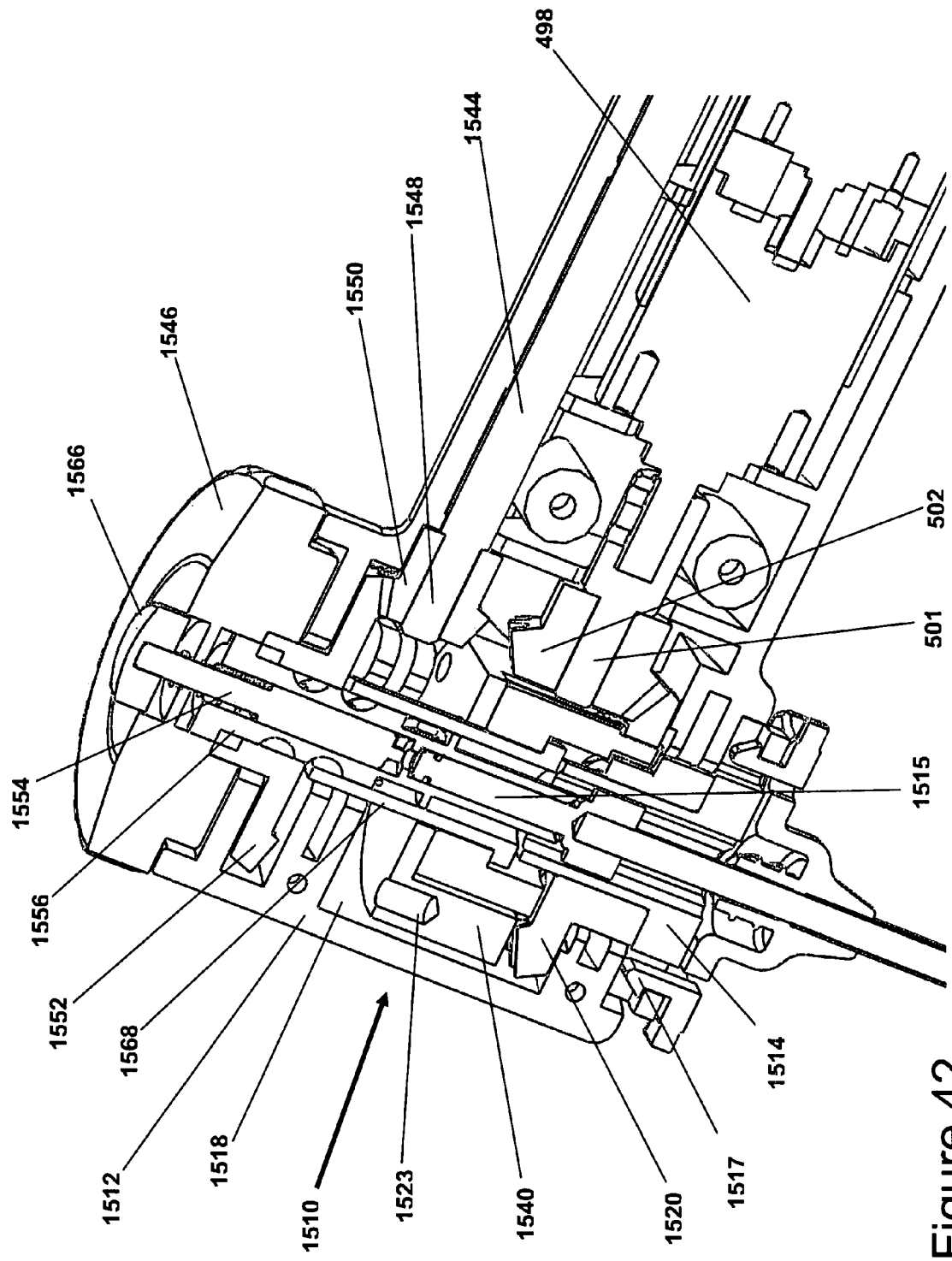
FIG. 42 is an enlarged side perspective view, in cross section of the head portion shown in FIG. 38.
Figure 43:
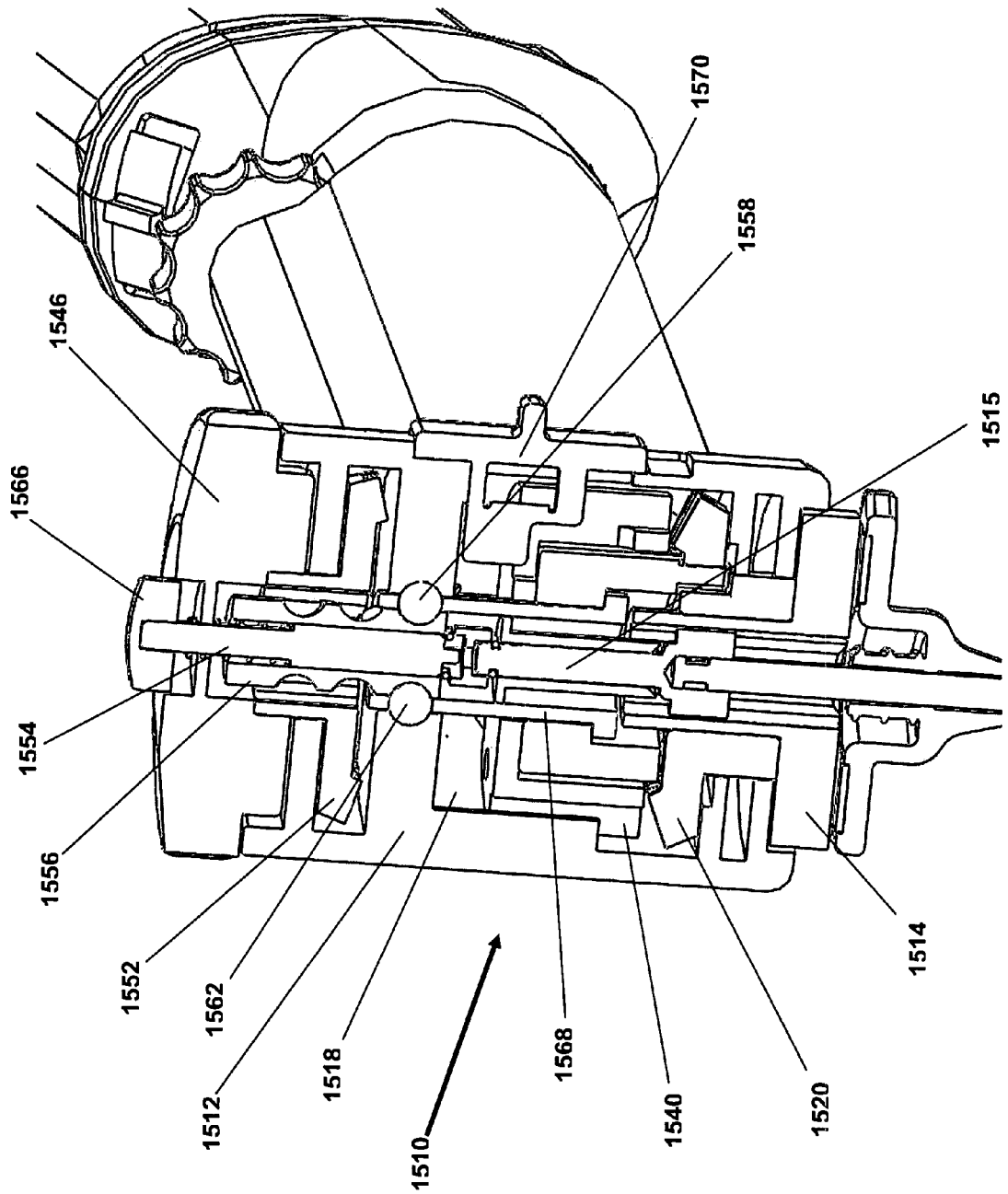
FIG. 43 is an enlarged front perspective view, in cross section of the head portion shown in FIG. 38.

Referring to FIGS. 37-39, an alternate embodiment of bone drill 410 is shown, which includes a sheath 810, similar to that described with regard to FIGS. 25-33. Sheath 810 has a proximal end including a drive head 812 and a distal end (not shown). Drive head 812 includes multiple projections on an outer periphery thereof. A drive cylinder 814 of head portion 418, similar to drive cylinder 508 described above, has an end 816, which includes openings 818. Openings 818 are configured to receive flexibly resilient projections 820 to mount sheath 810 with drive cylinder 814. As shown in FIG. 38, tabs 822, mounted with drive head 812 and connected with projections 820, are manipulated inwardly such that the clasp portion of projection 820 can pass through opening 818. As drive head 812 engages end 816, tabs 822 are released such that sheath 810 is fixed with head portion 818 in a locking configuration. Such a locking configuration is releasable, and sheath 810 can be released from end 816 by depressing tab 822 so that the clasp portion of projections 820 can pass through and withdraw from opening 818. It is envisioned that sheath 810 may be permanently affixed to head portion 818, or integrally formed therewith. This snap configuration of sheath 810 facilitates continuous rotation with the drill bit and allows the user to flex projections 820 and detach sheath 810 from bone drill 410, once in a desired location during a procedure.

Figure 34:
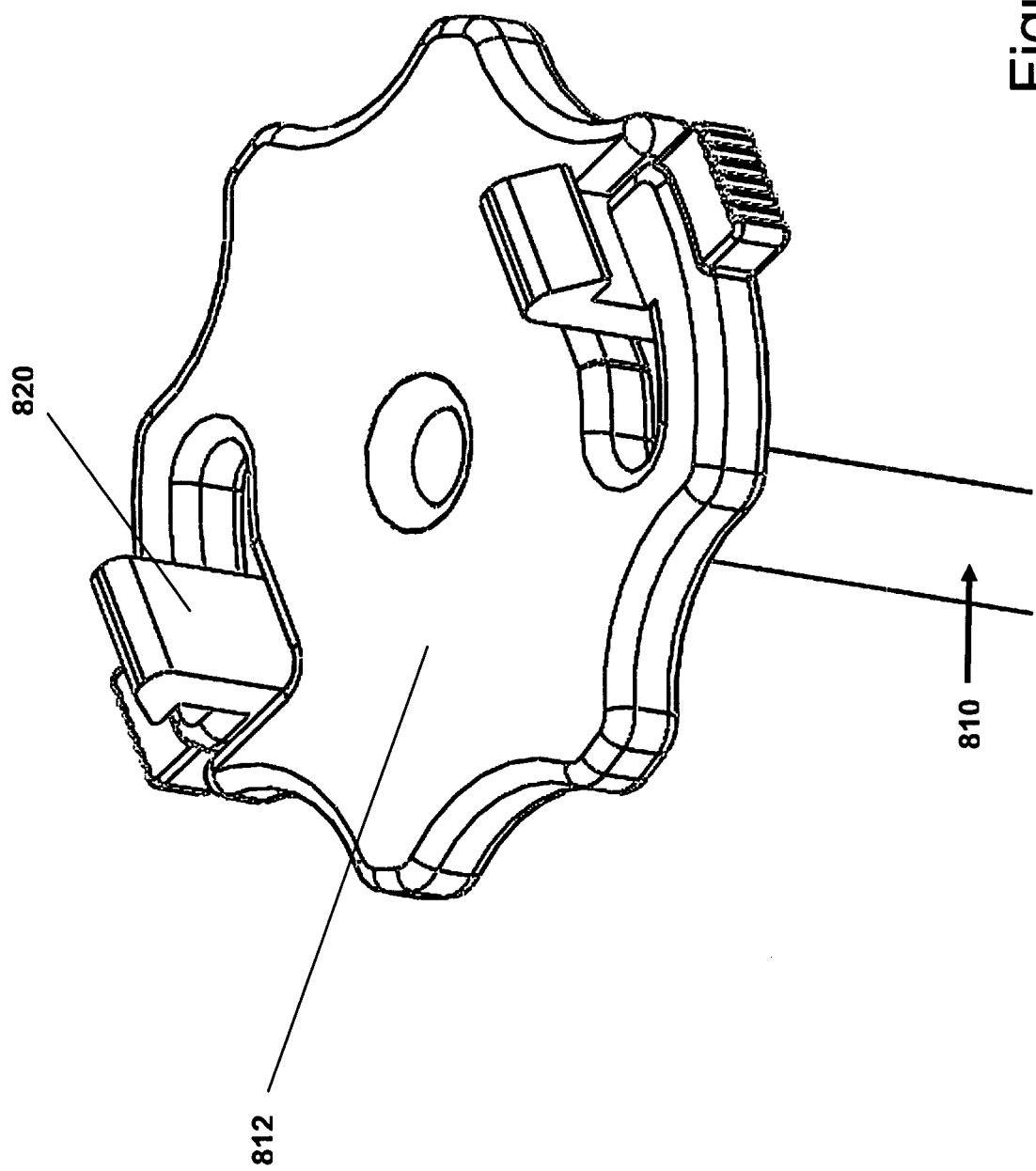
FIG. 34 is a perspective cutaway view of a sheath shown in FIG. 32.
Figure 35:
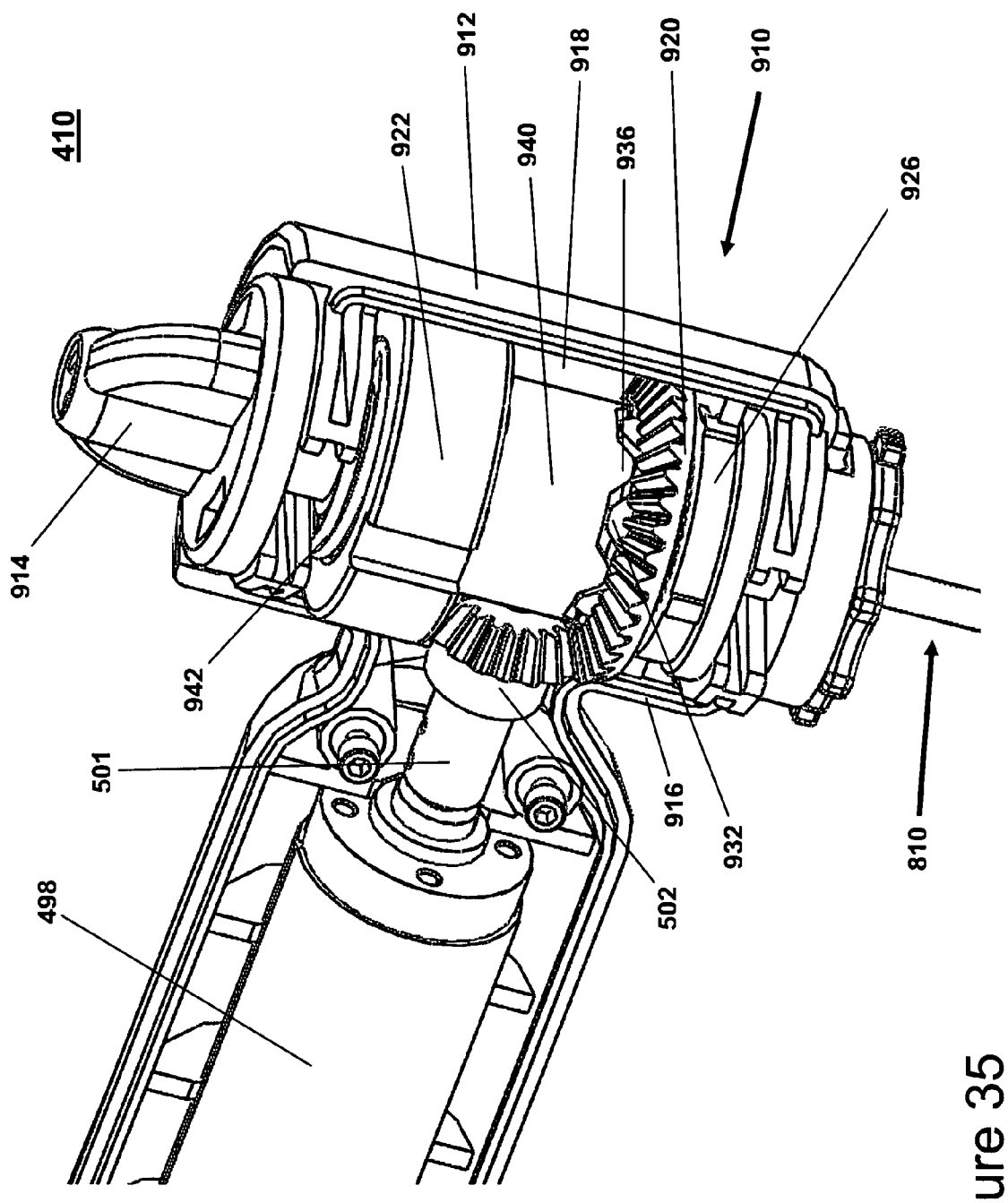
FIG. 35 is an enlarged side perspective sectional view with cover removed, of an alternate embodiment of the head portion shown in FIG. 20 constructed in accordance with the principles of the present invention.
Figure 36:
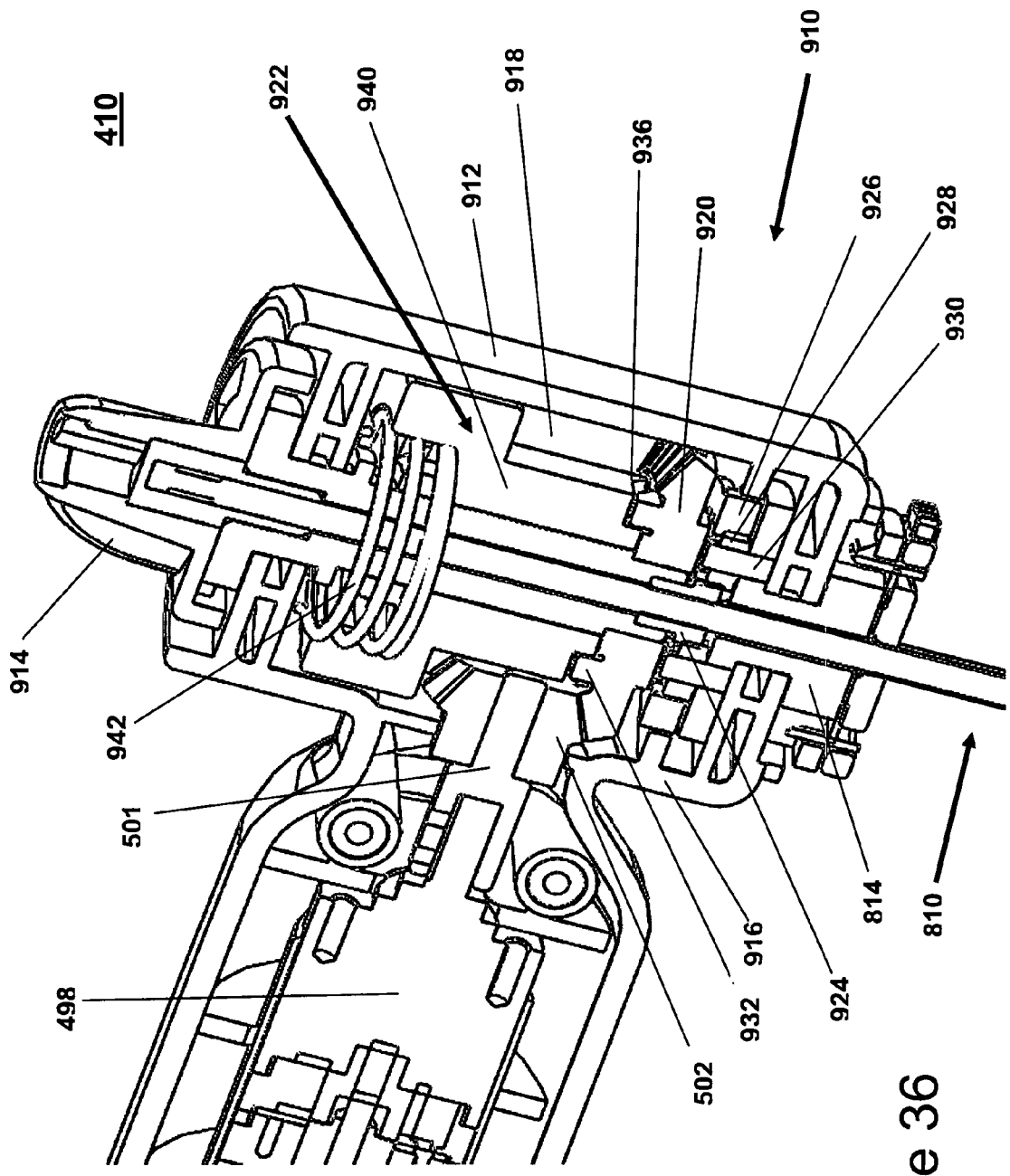
FIG. 36 is an enlarged side perspective view, in cross section of the head portion shown in FIG. 35.

Referring to FIGS. 35-37, an alternate embodiment of bone drill 410 is shown, similar to that described above, which includes a head portion 910 and sheath 810, described above with regard to FIGS. 32-34.

Head portion 910 has a body 912 that defines an interior cavity 918 that supports the drilling assembly drive gearing. Motor assembly 498 is operatively coupled to an output shaft 501, described above with regard to FIGS. 20-28, for rotation thereof via associated gearing. A bevel gear 502 is connected to output shaft 501 for meshing/engaging with the drilling assembly gearing in head portion 910.

Bevel gear 502 meshes with an input gear 920 of the drilling assembly gearing. Input gear 920 is retained with a support cylinder 514 (see FIG. 28), which is connected to drill bit 458 through drill bit handle 914. Input gear 920 includes teeth on an outer radial periphery thereof that meshes with the teeth of bevel gear 502. A gear 924 is mounted with support cylinder 514 which is turn drives the planetary gear system used to rotate sheath 810 as described in the previous embodiment. Thus, as bevel gear 502 rotates input gear 920, input gear 920 rotates support cylinder 922 and gear 924, causing the planet gears 928 to rotate and process along the fixed lower gear ring 926.

Figure 23:
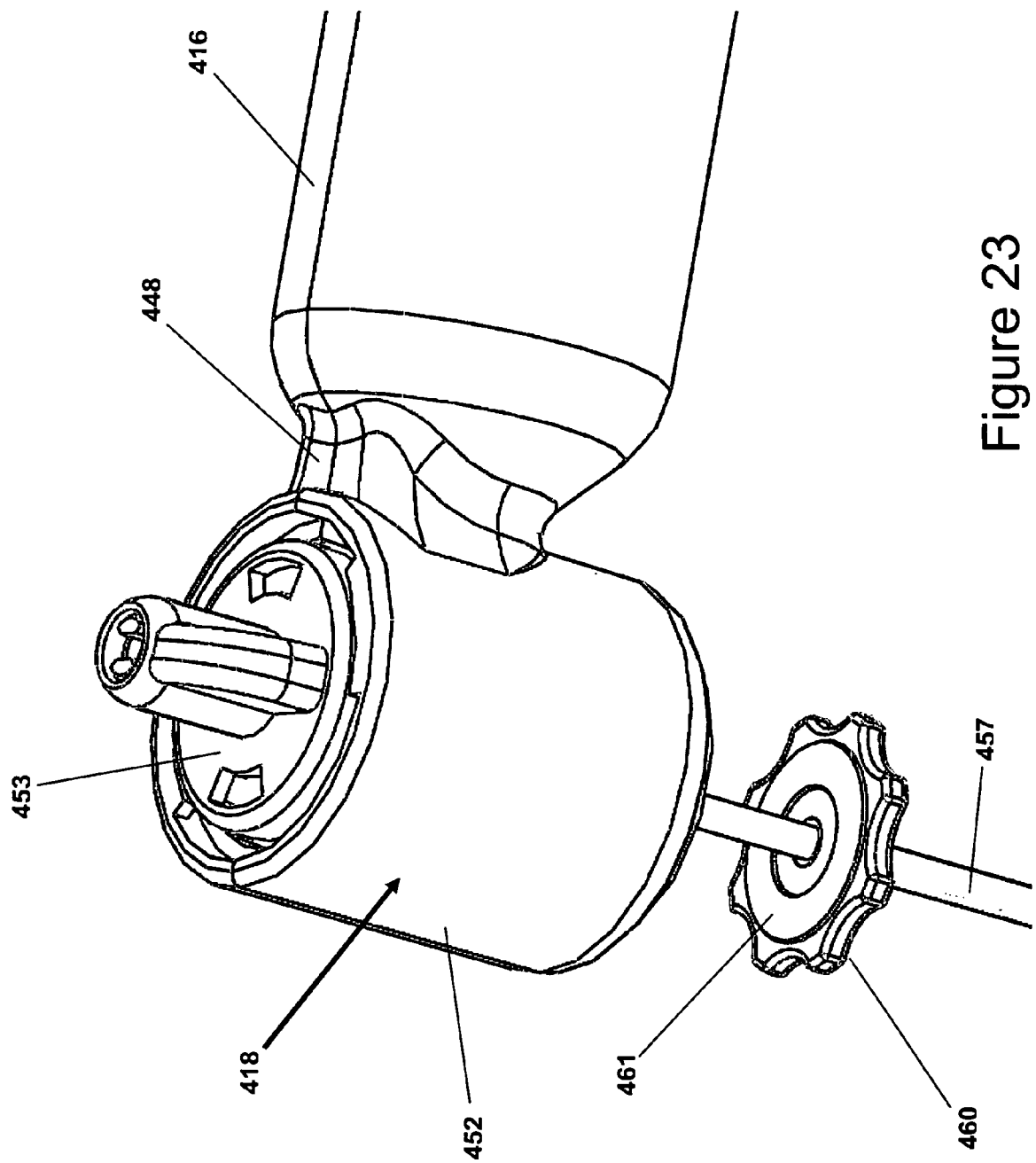
FIG. 23 is an enlarged top perspective cutaway view of the head portion shown in FIG. 20.
Figure 24:
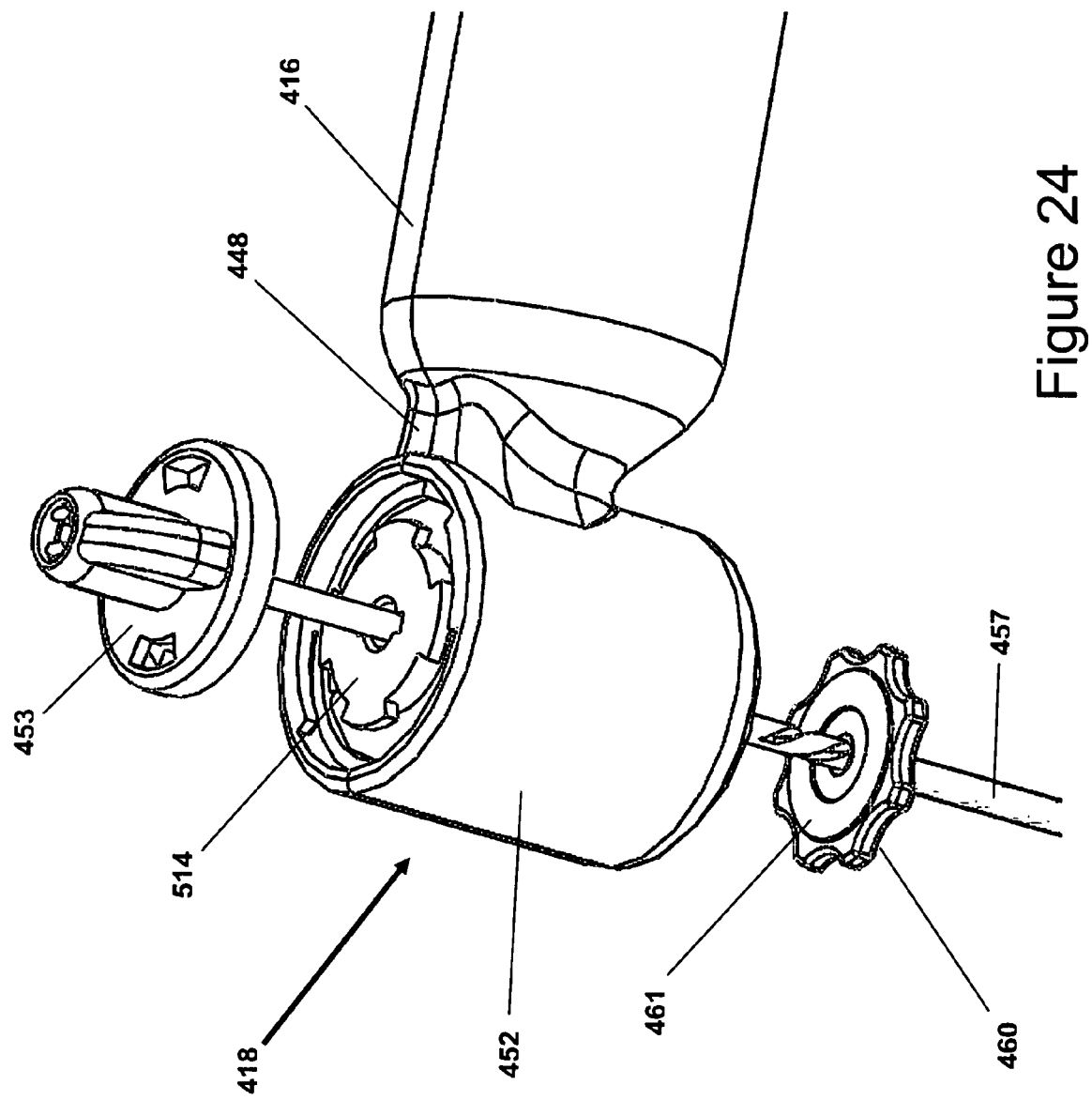
FIG. 24 is an enlarged top perspective view of the head portion shown in FIG. 20 with parts separated.
Figure 32:
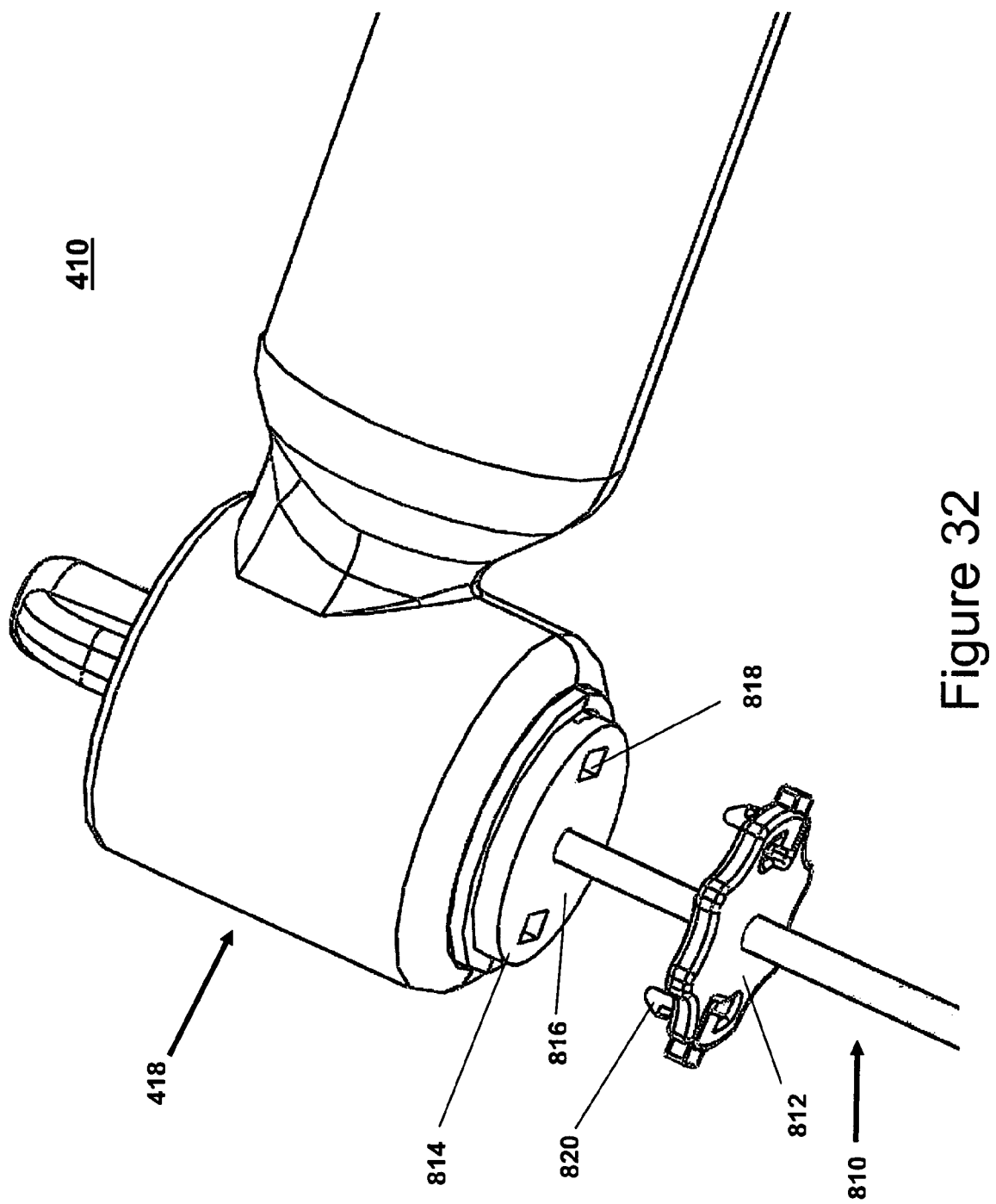
FIG. 32 is a bottom perspective cutaway view of an alternate embodiment of the head portion of the bone drill shown in FIG. 20.
Figure 33:
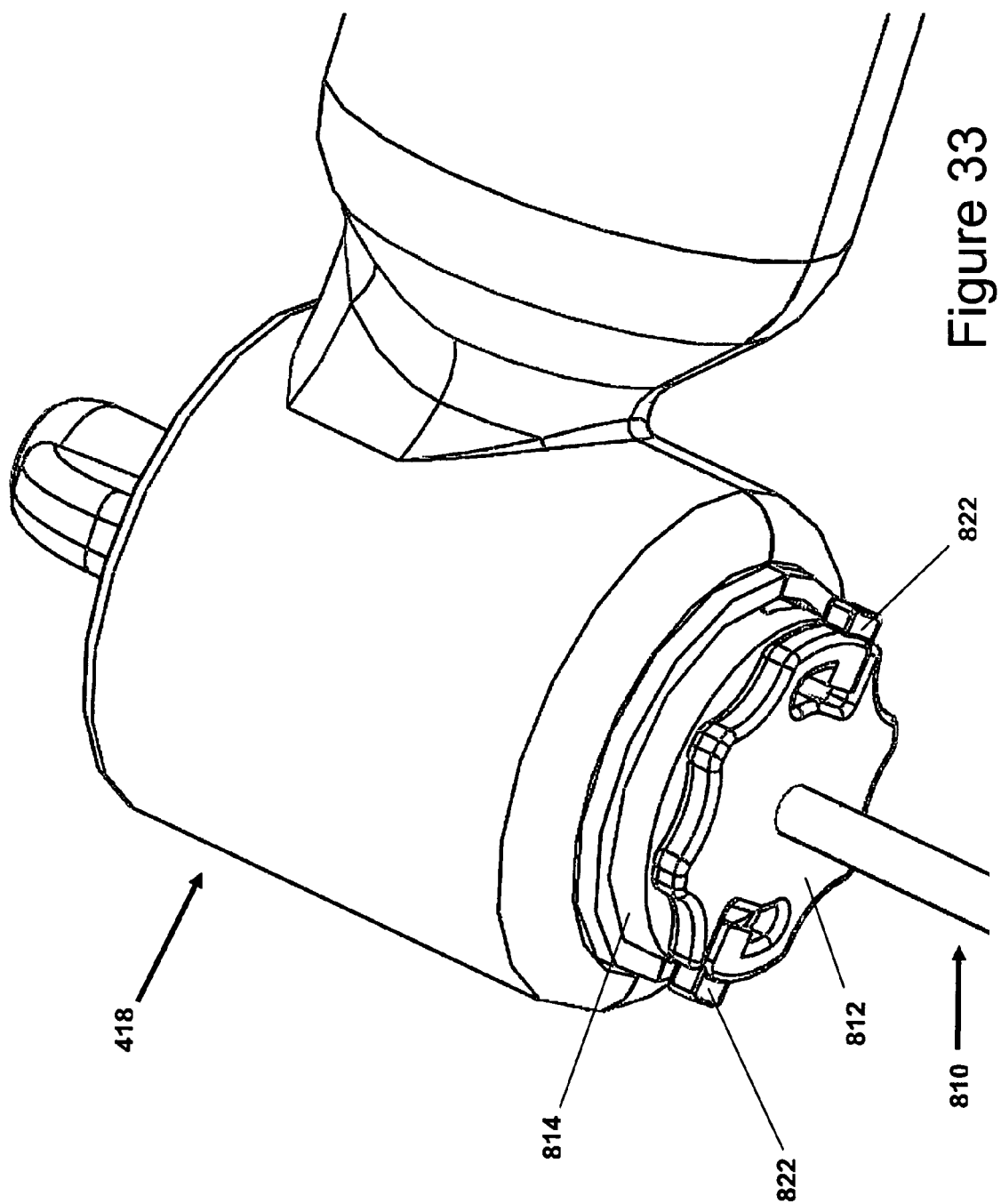
FIG. 33 is an enlarged bottom perspective view of the head portion shown in FIG. 32.

Drive cylinder 814, described with regard to FIGS. 32-34, carries gears 928 via respective gear shafts 930 disposed radially inside lower gear ring 926. Gears 928 are rotated by the teeth of gear 924 Support cylinder 514 rotates drill bit 458 by coupling through drill bit handle 914. Drive cylinder 814 is mounted with drive head 812 of sheath 810, as described above with regard to FIGS. 32-34. Thus, when drive head 812 is caused to rotate with drive cylinder 814, as described, sheath 810 rotates thereby effecting reaming the bore started by and/or being cut by drill bit 458. A bore is created that allows sheath 810 to extend therein via a friction plate or surface 461 (FIG. 23).

Input gear 920 has radially disposed cams 932 on an upper surface 934, which are correspondingly configured to engage radially disposed followers 936. Followers 936 are disposed on a lower surface 938 of an impact ram 940/922. Each cam 932 projecting from surface 934 has a constant slope to a crest or amplitude, and then a downward slope to a baseline, which begins the upward slope for the adjacent cam 932. Each follower 936, in a cooperative configuration with cams 932, has a constant downward slope to a baseline, which begins the downward slope for the adjacent follower 936.

A fixed rib 937 prevents rotation of impact ram 940 as input gear 920 rotates. Cams 932 and followers 936 are disposed in moveable engagement relative to each other. Input gear 920 may be rotated in both clockwise and counter-clockwise directions relative to ram 940. These alternative rotations are facilitated by the upward and downward slope portion on each of cams 932 and followers 936.

In operation, as input gear 920 rotates, cams 932 similarly rotate and engage followers 936. Such rotation and engagement cause followers 936 to displace about cams 932, causing impact ram 940 to move up and down according to the contact points of cam 932 and follower 936. As the crests or amplitude of the engaging cam 932 and follower 936 contact, ram 940 compresses a spring 942, mounted with support cylinder 922 of impact ram 940, within head portion 910, as shown in FIGS. 36.

Upon continued rotation past the crest contact point, the spring energy of spring 942 is released such that the force applied to spring 942 drives 940, as shown in FIG. 37, which is connected to drill bit 458. Accordingly, drill bit 458 (FIG. 21) is driven into bone during a procedure. The upward and downward slope for each of cams 932 and followers 936 are of a steep ascent/descent. This configuration facilitates a greater force or impact being applied to drill bit 458 in that the slope of the cam 932/follower 936 does not slow impact ram 940 travel as compared to a gradual slope. It is contemplated, however, that the slope or incline of cam 932/follower 936 may be variously angled according to the requirements of a particular procedure.

It is further contemplated that, alternative to the configuration of impact ram 940 discussed, impact ram 940 may be disposed 90 degrees from the drill bit axis and redirect the impact energy down and through the drill. It is envisioned that alternative to fixed rib 937, a sliding pin may be used. Such a configuration initiates and terminates the hammer/impact actions by retracting the pin back out of the slot in ram 940. This allows ram 940 to rotate with the bevel gear instead of being forced up against the spring pressure. When the pin is released, it will engage the slot in ram 940 causing it to cease rotation and begin repetitively moving axially against the spring pressure and releasing to impart impact energy into the drill bit.

Figure 44:
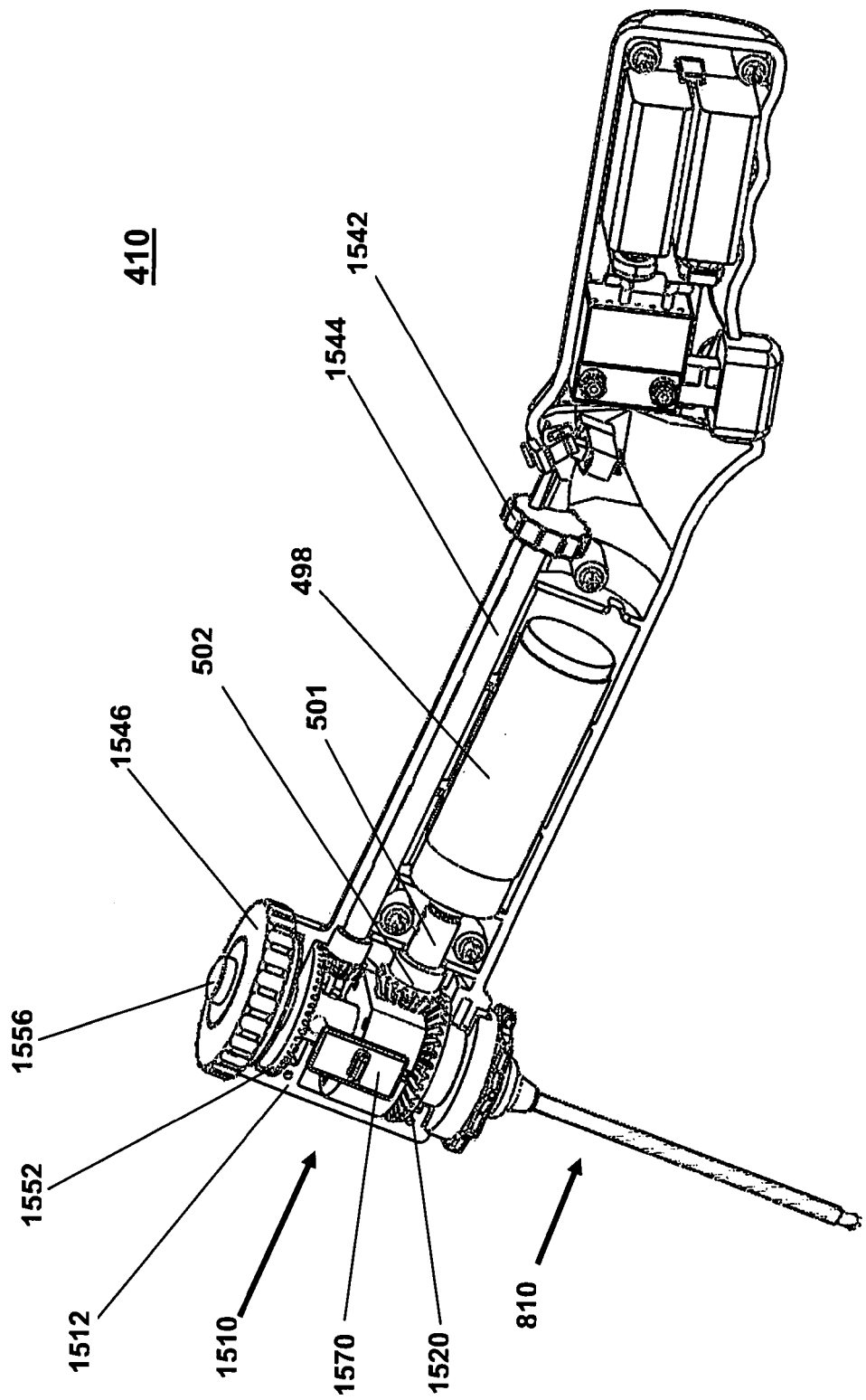
FIG. 44 is a side perspective sectional view with cover removed of the bone drill shown in FIG. 38.
Figure 45:
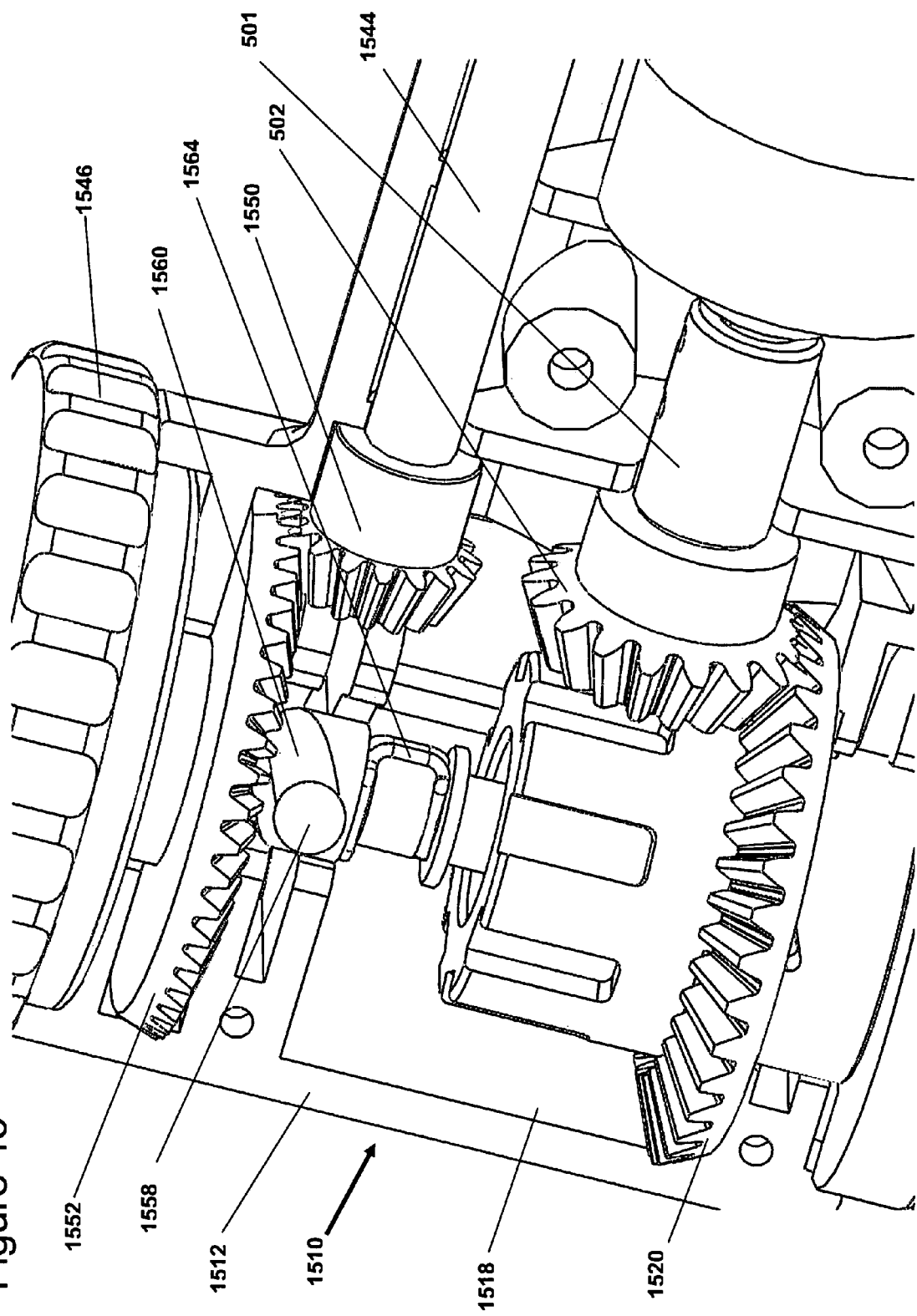
FIG. 45 is a side perspective sectional view with cover removed of the head portion of bone drill shown in FIG. 38.

Referring to FIGS. 38-45, an alternate embodiment of bone drill 410 is shown, similar to that described above, which includes a head portion 1510 and sheath 810, described above with regard to FIGS. 20-28. Bone drill 410 includes a forward/reverse switch 1511, which is connected to the power supply, the variable speed trigger switch, and the motor. It is contemplated that bone drill 410 may employ nine volt batteries as a power source, as shown in FIG. 44. It is further contemplated that bone drill 410 may employ various battery or portable power arrangements, AC or DC power sources, etc.

Head portion 1510 has a body 1512 that defines an interior cavity 1518, which supports the drilling assembly drive gearing. Motor assembly 498 is operatively coupled to an output shaft 501, described above with regard to FIGS. 20-28, for rotation thereof via associated gearing. A bevel gear 502 is connected to output shaft 501 for meshing/engaging with the drilling assembly gearing in head portion 1510.

Bevel gear 502 meshes with an input gear 1520 of the drilling assembly gearing. Input gear 1520 is retained with a sheath drive plate 1514 (see FIG. 45). The inner bore of sheath drive plate 1514 has axial spline grooves that slidably mate with drill bit lock 1515. Drill bit 458, with drill bit lock 1515, is inserted into the sheath drive plate, with the splines sliding in the grooves, until the groove on the end of the drill bit lock is captured by the spring wire catch 1564. The rotation of bevel gear 502 induces rotation in drill bit 458 through sheath drive plate 1514 and drill bit lock 1515. After locking the drill bit in place, sheath 810 is inserted over drill bit 458 until it locks onto sheath drive plate 1514 by two locking tabs 1517. In this particular embodiment, the sheath and the drill bit rotate at the same speed.

Input gear 1520 has radially disposed cams, which are correspondingly configured to engage radially disposed followers of an impact ram 1540, similar to input gear 920 and impact ram 940 described above with regard to FIGS. 35-37 and operate in a similar manner.

Impact ram 1540 rotates with input gear 1520. Alternatively, an impact switch 1570 is moved to provide a stop for impact ram 1540 to stop rotation and cause impact ram 1540 to move up and down. Impact ram 1540 includes a ram weight 1523 to increase impact force. Ram weight 1523 has 3 holes configured for supporting compression springs that provides return force.

A knob 1542 extends laterally from body 1512 via a shaft 1544. Knob 1542 is configured to facilitate remote manipulation of a knob 1546 from a distance that allows the users hands to remain away from the radiation beam while adjusting the sheath extension. Knob 1542 is knurled to facilitate manipulation thereof. Rotating knob 1546 directly or remotely using knob 1542, causes the components of drill bit 458 to extend or retract relative to sheath 810 for creating a cavity in targeted bone.

Shaft 1544 includes an output shaft 1548, mounted with a bevel gear 1550, which translates rotation of knob 1542 and shaft 1544 to the gearing of body 1512. Bevel gear 1550 meshes with an input gear 1552 of the gearing of body 1512. Input gear 1552 is mated to knob 1546 through the upper housing of body 1512. Input gear 1552 includes teeth radially disposed thereabout that mesh with teeth of bevel gear 1550. As bevel gear 1550 rotates, as caused by rotation of shaft 1544 described above, input gear 1552 is caused to rotate, which in turn rotates knob 1546.

Knob 1546 is knurled to facilitate manipulation thereof. Knob 1546 is disposed for extension and retraction of the components of drill bit 458. Knob 1546 is slidably mounted to push rod 1554. As knob 1546 rotates, a shuttle 1556 rotates, via splines that threadably engage input gear 1552. The sliding splines allow the shuttle 1556 to translate axially relative to gear 1552 as it rotates. Shuttle 1556 is fixed in position along the drive axis of body 1512 by guide balls 1558 that ride in helical grooves 1560 of shuttle 1556. Guide balls 1558 are fixed in position with recesses 1562 of housing 1512. Thus, rotation of shuttle 1556 causes shuttle 1556 to translate up or down due to the threaded engagement of helical grooves 1560 with the fixed guide balls 1558.

Shuttle 1556 locks the proximal end of drill bit lock 1515 via a spring wire form 1564 that springs out and then back into a groove on the proximal end of drill bit 1515. To remove drill bit 1515, drill bit 1515 is retracted completely so that push rod 1554 engages spring wire form 1564. An eject button 1566, connected to push rod 1554, is depressed such that push rod 1554 engages and spring wire form 1564 opens, releasing the proximal end of drill bit 1515.

A slide 1568 translates impact energy from impact ram 1540 to shuttle 1556. Slide 1568 translates the impact energy through guide balls 1558. As impact ram 1540 moves downward, impact ram 1540 engages the flange on slide 1568. Slide 1568 moves downward, pulling guide balls 1558 in the same direction. Guide balls 1558 in turn cause shuttle 1556 to move downward, transferring the impact energy through drill bit 1515 into the bone. If impact switch 1570 is slid vertically toward knob 1546, it removes the rotational stop from impact ram 1540 allowing it to preferentially rotate with bevel gear 502 instead of translating axially against the spring forces. This stops the impact function allowing pure rotation of the drill bit.

An alternate embodiment for a body of a bone drill fashioned in accordance with the present principles separates the handle portion from the drive or motor portion. Thus, the drive portion would extend from one radial side of the head portion while the handle portion would extend from another radial side of the head portion, preferably, but not necessarily at 180° therefrom to provide a balance in weight about the drill bit or weight distribution relative to the drill bit. This reduces any torque or moments that cause twisting and thus possible bone damage.

While the inventions have been illustrated and described in detail in the drawings and foregoing description, the same is to be considered as illustrative and not restrictive in character, it being understood that embodiments have been shown and described and that all changes and modifications that come within the spirit of these inventions are desired to be protected.

What is claimed is:

1. A bone drill comprising:
an elongate tubular handle member defining a first longitudinal axis and having a proximal end and a distal end,
an elongate tubular drive member defining a second longitudinal axis and having a proximal end and a distal end, the proximal end of the elongate tubular drive member being connected to the distal end of the elongate tubular handle member such that the second longitudinal axis is disposed at an angle offset from the first longitudinal axis, the offset angle ranging from 5 to 45 degrees relative to the first longitudinal axis;
a cylindrical head portion connected to the distal end of the elongate tubular drive member, the cylindrical head portion defining a third longitudinal axis that is disposed at an angle offset from the first longitudinal axis, or at an angle offset from both the first and second longitudinal axes;
a tubular sheath extending from the cylindrical head portion along a transverse axis relative to the first, second and third longitudinal axes, the tubular sheath including a distal end configured to engage bone; and
a drill bit axially disposed within and extending along the length of the tubular sheath, the drill bit comprising a distal tip that extends past the distal end of the tubular sheath.

2. A bone drill as recited in claim 1, further comprising radio opaque markers configured for alignment of the bone drill during a fluoroscopy procedure.

3. A bone drill as recited in claim 1, wherein the cylindrical head portion is formed of the radiolucent material and the tubular sheath is formed of radiolucent and radio opaque materials.

4. A bone drill as recited in claim 1, wherein the tubular sheath is configured to rotate independent of the drill bit and subsequent to drilling of a hole to a partial depth in a bone by the drill bit.

5. A bone drill as recited in claim 1, wherein the tubular sheath is configured to rotate relative to the cylindrical head portion.

6. A bone drill as recited in claim 1, wherein the tubular sheath is configured to rotate in an oscillating configuration such that the distal end rotates in a clockwise direction and a counterclockwise direction.

7. A bone drill as recited in claim 1, wherein the tubular sheath is configured for axial movement relative to the cylindrical head portion.

8. A bone drill as recited in claim 7, wherein the axial movement is spring driven to facilitate an impact engagement of the distal end and the bone.

9. A bone drill as recited in claim 1, further comprising a radiation protection guard mounted to the elongate tubular handle member.

10. The bone drill as recited in claim 1, further comprising a gearing assembly disposed within the cylindrical head, the gearing assembly configured to rotate the drill bit independently of the tubular sheath at a first speed, and rotate the tubular sheath independently of the drill bit at a second speed that is slower than the first speed.

11. A bone drill as recited in claim 10, further comprising a brake configured to control rotation of the tubular sheath.

12. A bone drill as recited in claim 1, wherein the tubular sheath includes external threads that are configured to control feed rate of the drill bit into bone.

13. A bone drill as recited in claim 12, wherein the tubular sheath includes a radially extending stop.

14. A bone drill as recited in claim 1, wherein the drill bit has an outer cutting sheath and an inner drill bit.

15. A bone drill as recited in claim 14, wherein the outer cutting sheath is removable from the tubular sheath for implanting with bone.

16. A bone drill as recited in claim 1, wherein the distal end of the tubular sheath includes a plurality of cutting tines.

17. A bone drill as recited in claim 1, wherein the tubular sheath and the drill bit are independently axially movable relative to the cylindrical head portion.

18. A bone drill comprising:
an elongate tubular handle member defining a first longitudinal axis and having a proximal end and a distal end,
an elongate tubular drive member defining a second longitudinal axis and having a proximal end and a distal end, the proximal end of the elongate tubular drive member being connected to the distal end of the elongate tubular handle member such that the second longitudinal axis is disposed at an angle ranging from 0 to 45 degrees relative to the first longitudinal axis;
a cylindrical head portion connected to the distal end of the elongate tubular drive member, the cylindrical head portion defining a third longitudinal axis that is disposed at an angle relative to the first longitudinal axis, or at an angle offset from both the first and second longitudinal axes;
a tubular sheath extending from the cylindrical head portion and configured for axial movement relative to the cylindrical head portion, the tubular sheath including a distal end configured to engage bone, the axial movement being spring driven to facilitate an impact engagement of the distal end and the bone; and
a drill bit axially disposed within and extending along the length of the tubular sheath, the drill bit comprising a distal tip that extends past the distal end of the tubular sheath.

19. A bone drill comprising:
an elongate tubular handle member defining a first longitudinal axis and having a proximal end and a distal end,
an elongate tubular drive member defining a second longitudinal axis and having a proximal end and a distal end, the proximal end of the elongate tubular drive member being connected to the distal end of the elongate tubular handle member such that the second longitudinal axis is disposed at an angle ranging from 0 to 45 degrees relative to the first longitudinal axis;
a cylindrical head portion connected to the distal end of the elongate tubular drive member, the cylindrical head portion defining a third longitudinal axis that is disposed at an angle relative to the first longitudinal axis, or at an angle offset from both the first and second longitudinal axes;
a tubular sheath extending from the cylindrical head portion, the tubular sheath including a distal end configured to engage bone; and
a drill bit axially disposed within and extending along the length of the tubular sheath, the drill bit comprising an outer cutting sheath, an inner drill bit and a distal tip that extends past the distal end of the tubular sheath.

* * * * *